United States Patent
Crich et al.

(10) Patent No.: US 11,466,044 B2
(45) Date of Patent: Oct. 11, 2022

(54) NEOMYCIN AND PAROMOMYCIN DERIVATIVES

(71) Applicants: WAYNE STATE UNIVERSITY, Detroit, MI (US); UNIVERSITAT ZURICH, Zurich (CH)

(72) Inventors: David Crich, Detroit, MI (US); Girish Sati, Detroit, MI (US); Amr Sonousi, Detroit, MI (US); Guanyu Yang, Detroit, MI (US); Appi Reddy Mandhapati, Detroit, MI (US); Michael G. Pirrone, Detroit, MI (US); Takayuki Kato, Detroit, MI (US); Vikram Sarpe, Detroit, MI (US); Andrea Vasella, Zurich (CH); Erik C. Bottger, Zurich (CH); Sven N. Hobbie, Zurich (CH)

(73) Assignees: WAYNE STATE UNIVERSITY, Detroit, MI (US); UNIVERSITAT ZURICH, Zurich (CH)

( * ) Notice: Subject to any disclaimer, the term of this patent is extended or adjusted under 35 U.S.C. 154(b) by 229 days.

(21) Appl. No.: 16/603,230

(22) PCT Filed: Apr. 6, 2018

(86) PCT No.: PCT/US2018/026547
§ 371 (c)(1),
(2) Date: Oct. 6, 2019

(87) PCT Pub. No.: WO2018/187738
PCT Pub. Date: Oct. 11, 2018

(65) Prior Publication Data
US 2021/0107932 A1 Apr. 15, 2021

Related U.S. Application Data

(60) Provisional application No. 62/501,535, filed on May 4, 2017, provisional application No. 62/501,586, filed on May 4, 2017, provisional application No. 62/501,589, filed on May 4, 2017.

(30) Foreign Application Priority Data

Apr. 7, 2017 (EP) .................................... 17165612
Apr. 7, 2017 (EP) .................................... 17165620
Apr. 7, 2017 (EP) .................................... 17165623

(51) Int. Cl.
*C07H 15/232* (2006.01)
*C07H 15/224* (2006.01)
*A61P 31/04* (2006.01)
*C07H 19/01* (2006.01)

(52) U.S. Cl.
CPC ............ *C07H 15/232* (2013.01); *A61P 31/04* (2018.01); *C07H 15/224* (2013.01); *C07H 19/01* (2013.01)

(58) Field of Classification Search
None
See application file for complete search history.

(56) References Cited

U.S. PATENT DOCUMENTS 4,021,601 A 5/1977 Arcamone et al.
4,170,643 A 10/1979 Cier et al.

FOREIGN PATENT DOCUMENTS

DE 2411504 9/1974
WO 2008092690 8/2008
WO 2010004433 1/2010

OTHER PUBLICATIONS

Kiyoshi Nara et al: "Chemical modification of aminoglycoside antibiotics. Some N-alkyl derivatives of sorbistin A1 (P-2563) and butirosin A", Chemical & Pharmaceutical Bulletin, vol. 27, No. 1, Jul. 1, 1979, pp. 65-75.
Hiroshi Fukase et al: "A new method for 3'-deoxygenation of butirosins A and B", Carbohydrate Research, vol. 60, No. 2, Feb. 1, 1978, pp. 289-302.
Takayuki Kato et al: "Synthesis and Antiribosomal Activities of 4'-0, 6'-0-, 4' '-0-, 4', 6'-0 and 4' ', 6' '-0-Derivatives in the Kanamycin Series indicate Differing Target Selectivity Patterns between the 4, 5- and 4,6, -Series of Disubstituted 2-Deoxystreptamine Aminoglycoside Antibiotics", ACS Infectious Diseases, vol. 1, No. 10, Aug. 6, 2015, pp. 479-486.
Kudyba et al: "Synthesis of paromomycin derivatives modified at C(5' ') to selectively target bacterial rRNA", Carbohydrate Res, Pergamon, GB, vol. 342, No. 3-4, Jan. 30, 2007, pp. 499-519.
Martin Giera et al: "Structural elucidation of biologically active neomycin N- octyl derivatives in a regioisomeric mixture by means of liquid chromatography/ion trap time-of-flight mass spectrometry", Rapid Communications in Mass Spectrometry, vol. 24, No. 10, May 30, 2010, pp. 1439-1446.

*Primary Examiner* — Traviss C McIntosh, III
(74) *Attorney, Agent, or Firm* — JMB Davis Ben-David

(57) ABSTRACT

The present disclosure relates to derivatives of neamine-based aminoglycoside antibacterial drugs modified in position C6', C2' and/or C5". The modifications impart favorable properties regarding activity against ESKAPE pathogens, evasion of resistance traits and increased selectivity, enabling systemic use of the compounds.

18 Claims, 21 Drawing Sheets

6'- and 5''-Amino and Formamido Modifcations of 4'-deoxy-4'-C-propyl series

6'-C-Methyl-6'-N-(2-hydroxyethyl)neomycin

6' and 5''-Hydroxyethylamino-4'-deoxy-4'-C-propyl-1-N-LHABA parom

6'-C-Methyl Lividomycin B

5"-Deoxy-5"-formamido-1-N-LHABA paromomycin

5"-Deoxy-5"-formamido-6'-N-(2-hydroxyethyl)-1-N-LHABA neomycin

2'-N-Alkyl-4'-deoxy-4'-propyl paromomycin Derivatives

NEOMYCIN AND PAROMOMYCIN DERIVATIVES

CROSS-REFERENCE TO RELATED APPLICATIONS

This is the U.S. National Stage of International Patent Application No. PCT/US2018/026547 filed on Apr. 6, 2018, which claims priority to European Patent Application No. EP17165620.0 filed on Apr. 7, 2017, European Patent Application No. EP17165623.4 filed on Apr. 7, 2017, European Patent Application No. EP17165612.7 filed on Apr. 7, 2017, U.S. Provisional Patent Application No. 62/501,535 filed on May 4, 2017, U.S. Provisional Patent Application No. 62/501,586 filed on May 4, 2017, and U.S. Provisional Patent Application No. 62/501,589 filed on May 4, 2017, the entire contents of each of which are incorporated by reference herein in their entirety.

STATEMENT REGARDING FEDERALLY SPONSORED RESEARCH OR DEVELOPMENT

This invention was made with government support under grant 1R01AI123352-01 awarded by the National Institutes of Health. The government has certain rights in the invention.

FIELD OF THE DISCLOSURE

Provided are aminoglycoside compounds based on the neomycin scaffold having improved antibacterial properties. The present disclosure further relates to use of the compounds in the treatment of infections by pathogens carrying certain resistance genes rendering such pathogens refractive to classical aminoglycoside antibacterial drugs.

BACKGROUND

Aminoglycoside antibiotics are among the most potent and successful antibacterial therapeutics in medical history. The emergence and widespread dissemination of antimicrobial resistance poses a global health threat of continuously increasing magnitude. Two mechanisms account for the resistance to aminoglycoside antibiotics: methylation of N7-G1405 in the 16S-rRNA binding site, and inactivation of the drug by aminoglycoside modifying enzymes. The development of next-generation aminoglycoside antibiotics will therefore need to rely on 4,5-disubstituted deoxystreptamines, which retain binding to and activity against G1405-methylated ribosomes. Furthermore, next-generation aminoglycoside antibiotics need to be designed to circumvent the clinically most relevant aminoglycoside-modifying enzymes without compromising antibacterial potency or drug safety.

Important examples are paromomycin (PAR) and Neomycin B (NEO_B). These consist of four rings, the numbering of which is given below for reference.

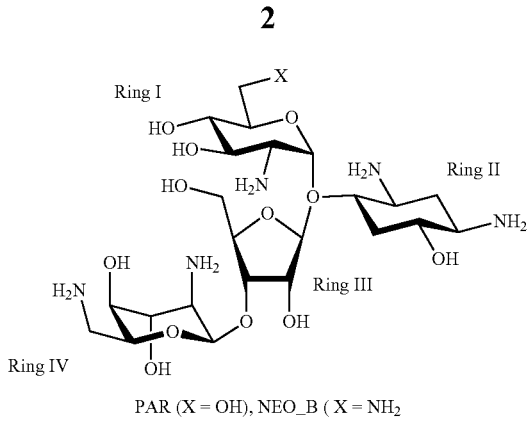

PAR (X = OH), NEO_B (X = NH$_2$)

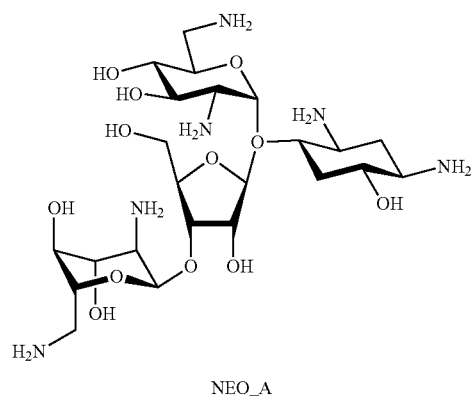

NEO_A

Two classes of AGA are distinguished by the connection of carbocycles to the deoxystreptamine moiety (ring II): paromomycin and neomycin are the examples of the (4,5) class, other related compounds include the (4,5) AGA lividomycin (LIV) and ribostamycin (RIB). Xylostacin (XYL, CAS number 50474-67-4) is the 3"-isomer of ribostamycin.

Kanamycin (KAN; Kanamycin A: $K^2$=OH, $K^6$=NH$_2$; Kanamycin B: $K^6$=NH$_2$; Kanamycin C: $K^2$=NH$_2$, $K^6$=OH, Tobramycin: 3"-deoxy), geneticin (GEN; A=(R)CH(OH)CH$_3$) and amikacine (AMI) are examples of the (4,6) AGA class.

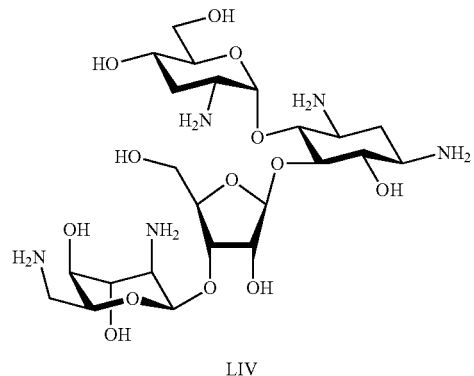

LIV

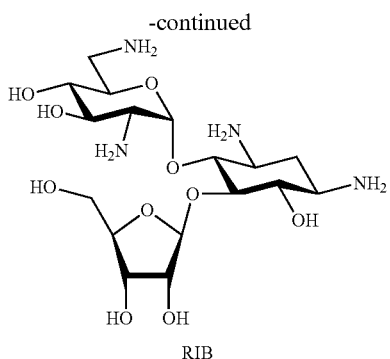
RIB

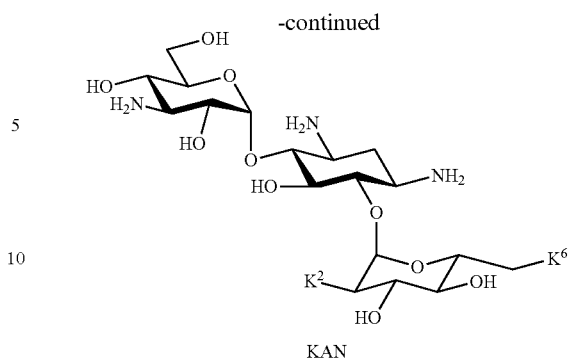
KAN

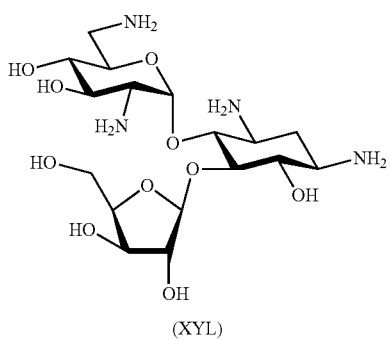
(XYL)

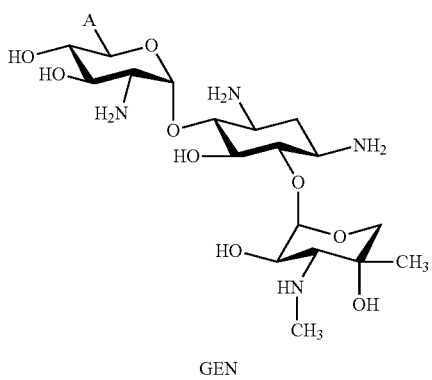
GEN

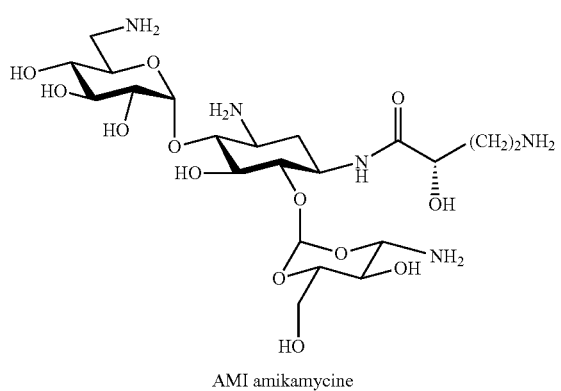
AMI amikamycine

Many AGA drug candidates based on the above scaffolds have been developed over more than 50 years, and a vast number of synthetic approaches are known to the skilled artisan. A comprehensive review of modern aminoglycoside chemistry, particularly as it pertains to the compounds disclosed herein, is available in Wang and Chang, Aminoglycoside Antibiotics: From Chemical Biology to Drug Discovery, $2^{nd}$ Ed. (Editor: D. Arya), Wiley 2007.

The most important mechanism by which bacteria evade the action of existing AGAs is by the action of aminoglycoside modifying enzymes (AMEs) on the drug. While AMEs vary between different bacteria, only a limited number of positions on the AGA framework are modified across the complete spectrum of bacteria.

One of the more widespread classes of AME is the class of 3'-aminoglycoside phosphotransferases APH(3') whose various isoforms phosphorylate at the AGA 3'-position (ring I) in an ATP-dependent manner. APH(3') has been found in a large variety of pathogens including E. coli, S. enterica, K. pneumoniae, A. baumannii, S. marcescens, Corynebacterium, Photobacterium, Citrobacter, P. aeruginosa, S. maltophilia, S. aureus, Enterococcus, B. circulans, C. jejuni, and others (reviewed in Drug Resistance Updates 13:151 and other reports). Importantly, P. aeruginosa has a chromosomal APH(3') gene that makes it intrinsically resistant to most aminoglycoside antibiotics.

Modification of the AGAs by deoxygenation at the 3'-position, as in tobramycin and lividomycin, overcomes resistance due to 3'-phosphorylation by APH(3'). However, numerous isoforms of the APH(3') have the ability also to phosphorylate at the 5"-position (ring III) of the 4,5-AGA, making them formally APH(3',5") AMEs. Thus, for example, APH(3')-IIIa AME phosphorylates the 3'-deoxy 4,5-AGA lividomycin at the 5"-position leading to resistance in bacteria that carry this AME. Indeed, the present inventors have determined that certain APH(3',5") isoforms are more effective at phosphorylation of the 5"-position than of the 3'-position. Attempts to circumvent the ability of APH(3',5") AMEs to phosphorylate at the 5"-position described in the literature have involved the removal of the 5"-hydroxy group by deoxygenation and its replacement by halogen atoms, but these modifications result in a substantial loss of antibacterial activity. Modifications involving oxidation of the 5"-alcohol to the corresponding aldehyde or carboxylic acid followed by the formation of oximes or amides also result in the loss of antibacterial activity. The replacement of the 5"-hydroxy group by an amino group gives compounds that retain the antibiotic activity of the parent, in manner dependent on the amine substituent, but which, because of the presence of additional basic amino group, lead to enhanced binding to eukaryotic ribosomes which reduces the therapeutic index as a consequence of increased toxicity.

The AAC(2') class of AMEs promote bacterial resistance by acetylation of the 2'-amino group of the AGAs giving the 2'-acetamido derivatives, which have lower affinity for the bacterial ribosome. Accordingly, an authentic sample of the 2'-N-acetamide of neomycin B (compound 183 of the present specification) has very significantly reduced activity against MRSA and *E coli* (see Tables 1 and 2 of example 3) as compared to the parent neomycin B. The action of AAC(2') may be blocked by removal of the 2'-amino group, by replacement of the 2'-amino group by a hydroxyl group or by a halogen atom, by alkylation of the 2'-amino group, or by acylation of the 2'-amino group with an acyl residue different from the acetyl group installed by the enzyme. However, the influence of such modifications on antibacterial activity and ribosomal activity (hence on ototoxicity) is not entirely predictable.

The AAC(2') resistance mechanism has been described for various gram-negative clinical pathogens; one aspect of clinical relevance is its occurrence as inherent resistance mechanism encoded on the chromosomes of Mycobacteria (see Drug Resistance Updates 13:151).

It has been demonstrated, on the basis of genetic studies of aminoglycoside interactions with eukaryotic ribosomal 12S rRNA, that AGAs inhibit mitochondrial protein synthesis which enhances the cochlear toxicity associated with aminoglycosides. Crystallographic analyses of rRNA hybrids of human wild-type, the human 12S rRNA A1555G mutant, and bacterial decoding A-sites, strongly support the hypothesis that AGA induced deafness is affected by genetic factors. Ototoxicity occurs in ways including: i) a random dose dependent manner in the common patient population, and ii) in an aggravated type in genetically susceptible individuals, with the latter linked to mutations in mitochondrial rRNA, in particular, the transition mutations A1555G and C1494U in the A-site of the mitochondrial ribosomal RNA subunit.

It is known that the 2'-N-ethyl derivative of paromomcyin (127) and the 2'-hydroxy-2'-deamino derivative of neomycin B (119) show comparable antibiotic potency to the parent compounds (Casinelli et al., J Antibiotics 1978, 31, 378 and ibid., 382). However, neither the effect on antibiotic activity of 2'-N-alkylation in neomycin B nor that of replacement of the 2'-amino group by a hydroxyl group in paromomycin was known previously.

Deamination in the 4,6-class of aminoglycosides has been shown to result in the formation of compounds that retain most of the antibacterial activity of the parent compounds, but the effect of such modifications on toxicity was not described. Moreover, as the present inventors have shown elsewhere (Salian et al., Antimicrob. Agents Chemother. 2012, 56, 6104; Kato et al., ACS Infect. Dis. 2015, 1, 479), modifications to ring I of the 2-deoxystreptamine class of aminoglycosides do not have the same influence in the 4,5-series as in the 4,6-series.

2'-N-Formylation is known to be an acceptable (natural) modification of the 4,6-aminoglycoside sisomicin. It is not known as an acceptable modification in the 4,5-series.

SUMMARY

Provided are aminoglycoside compounds based on the neomycin scaffold having improved antibacterial properties. The disclosure further relates to use of the compounds of the disclosure in the treatment of infections by pathogens carrying certain resistance genes rendering such pathogens refractive to classical aminoglycoside antibacterial drugs.

Based on the above-mentioned state of the art, the objective of the present disclosure is to provide improved aminoglycoside derivatives that allow treatment of infections by pathogens carrying resistance determinants, and which are show less ototoxicity and nephrotoxicity in human patients. This objective is attained by the claims of the present specification.

Most literature work on the deaminated aminoglycosides was conducted on the only modestly active pseudodisaccharide neamine and is of questionable relevance to the considerably more active pseudotetrasaccharides paromomycin and neomycin B. Indeed, as the data reveal, conclusions drawn on the effect of 2'-deamination on neamine microbiology and susceptibility to resistance mechanism by Mobashery (JACS 1995, 117, 11060) do not extrapolate to neomycin B or to paromomycin.

One aspect of the present disclosure teaches that forcing the ring I 6' carbon into a particular conformation or set of conformations, which increase affinity for the ribosome and increase antibacterial activity. In addition, these novel modifications of the AGA ring I overcome the action of at least two common aminoglycoside modifying enzymes and so, in addition to increased activity against wild-type bacteria, afford the possibility of use against resistant bacteria endowed with those AMEs.

DETAILED DESCRIPTION

Figure 1:
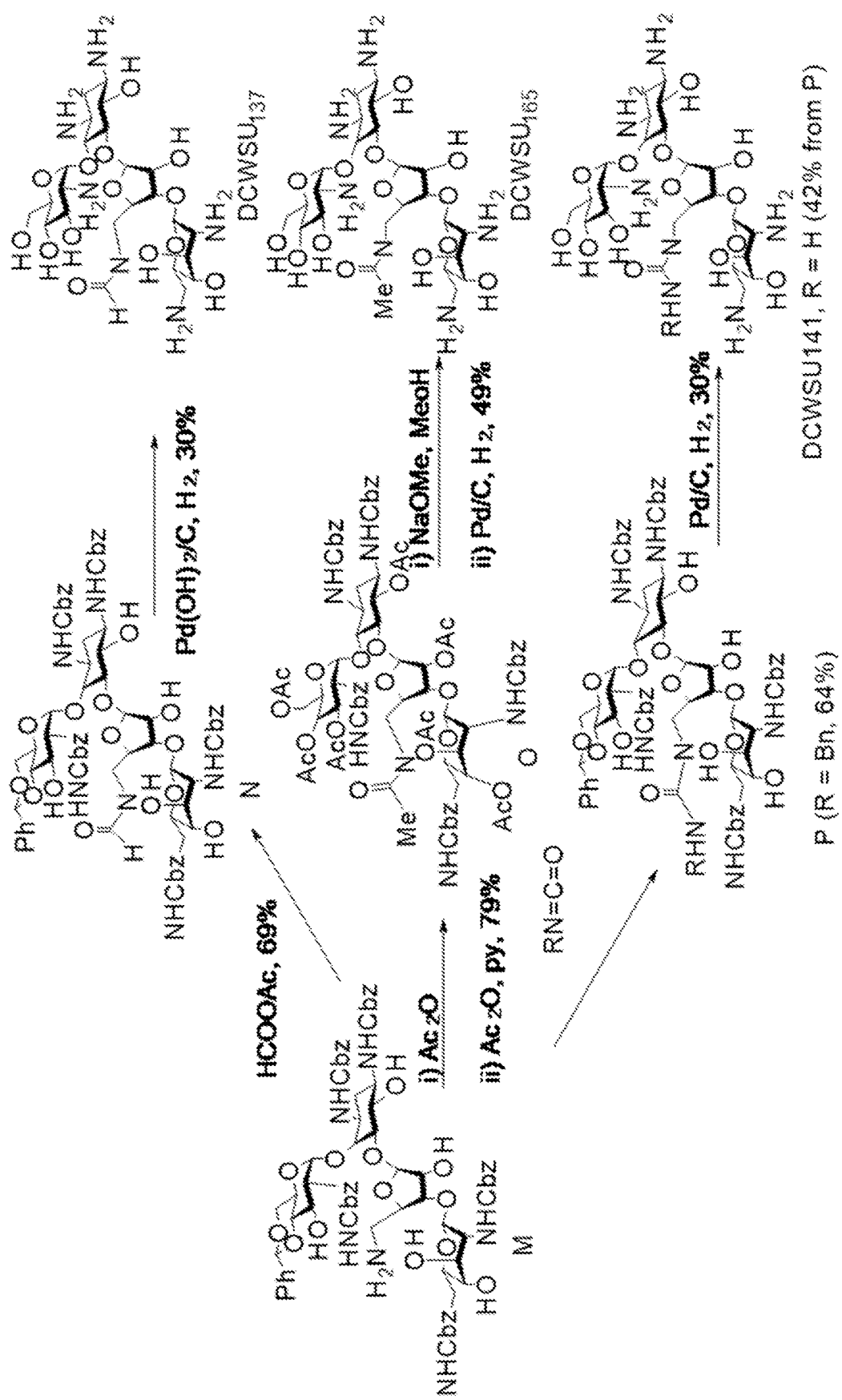
FIGS. 1-18 depict chemical formulas described herein.

Provided are aminoglycoside compounds based on the neomycin scaffold having improved antibacterial properties. The disclosure further relates to use of the compounds of the disclosure in the treatment of infections by pathogens carrying certain resistance genes rendering such pathogens refractive to classical aminoglycoside antibacterial drugs.

Based on the above-mentioned state of the art, the objective of the present disclosure is to provide improved aminoglycoside derivatives that allow treatment of infections by pathogens carrying resistance determinants, and which are show less ototoxicity and nephrotoxicity in human patients. This objective is attained by the claims of the present specification.

Most literature work on the deaminated aminoglycosides was conducted on the only modestly active pseudodisaccharide neamine and is of questionable relevance to the considerably more active pseudotetrasaccharides paromomycin and neomycin B. Indeed, as the data reveal, conclusions drawn on the effect of 2'-deamination on neamine microbiology and susceptibility to resistance mechanism by Mobashery (JACS 1995, 117, 11060) do not extrapolate to neomycin B or to paromomycin.

One aspect of the present disclosure teaches that forcing the ring I 6' carbon into a particular conformation or set of conformations, which increase affinity for the ribosome and increase antibacterial activity. In addition, these novel modifications of the AGA ring I overcome the action of at least two common aminoglycoside modifying enzymes and so, in addition to increased activity against wild-type bacteria, afford the possibility of use against resistant bacteria endowed with those AMEs.

Terms and Definitions

A $C_1$-$C_4$ alkyl in the context of the present disclosure signifies a saturated linear or branched hydrocarbon having 1, 2, 3 or 4 carbon atoms, wherein in particular embodiments one carbon-carbon bond may be unsaturated and one $CH_2$ moiety may be exchanged for oxygen (ether bridge) or nitrogen (NH, or NR with R being methyl, ethyl, or propyl; amino bridge). Non-limiting examples for a $C_1$-$C_4$ alkyl are methyl, ethyl, propyl, prop-2-enyl, n-butyl, 2-methylpropyl, tert-butyl, but-3-enyl, prop-2-inyl and but-3-inyl. In particular embodiments, a $C_1$-$C_4$ alkyl is a methyl, ethyl, propyl or butyl moiety.

The term $C_1$-$C_6$ alkyl similarly refers to $C_1$-$C_4$ alkyls and their higher homologues, including additionally 3-methylbut-2-enyl, 2-methylbut-3-enyl, 3-methylbut-3-enyl, n-pentyl, 2-methylbutyl, 3-methylbutyl, 1,1-dimethylpropyl, 1,2-dimethylpropyl, 1,2-dimethylpropyl, pent-4-inyl, 3-methyl-2-pentyl, and 4-methyl-2-pentyl. In particular embodiments, a $C_5$ alkyl is a pentyl moiety and a $C_6$ alkyl is a hexyl or cyclohexyl moiety.

Where used in the context of chemical formulae, the following abbreviations may be used: Me is methyl $CH_3$, Et is ethyl —$CH_2CH_3$, Prop is propyl —$(CH_2)_2CH_3$ (n-propyl, n-pr) or —$CH(CH_3)_2$ (iso-propyl, i-pr), but is butyl —$C_4H_9$, —$(CH_2)_3CH_3$, —$CHCH_3CH_2CH_3$, —$CH_2CH(CH_3)_2$ or —$CH(CH_3)_3$.

The term amino-substituted alkyl or hydroxyl substituted alkyl refers to an alkyl according to the above definition that is modified by one or several amine or hydroxyl groups $NH_2$, NHR, $NR_2$ or OH, wherein the R substituent as used in the current paragraph, different from other uses assigned to R in the body of the specification, is methyl, ethyl or propyl unless otherwise specified. An alkyl having more than one carbon may comprise more than one amine or hydroxyl. Unless otherwise specified, the term "substituted alkyl" refers to alkyl in which each C is only substituted by one amine or hydroxyl group, in addition to bonds to the alkyl chain, terminal methyl, or hydrogen.

Non-limiting examples of amino-substituted alkyl include —$CH_2NH_2$, —$CH_2NHMe$, —$CH_2NHEt$, —$CH_2CH_2NH_2$, —$CH_2CH_2NHMe$, —$CH_2CH_2NHEt$, —$(CH_2)_3NH_2$, —$(CH_2)_3NHMe$, —$(CH_2)_3NHEt$, —$CH_2CH(NH_2)CH_3$, —$CH_2CH(NHMe)CH_3$, —$CH_2CH(NHEt)CH_3$, —$(CH_2)_3CH_2NH_2$, —$(CH_2)_3CH_2NHMe$, —$(CH_2)_3CH_2NHEt$, —$CH(CH_2NH_2)CH_2CH_3$, —$CH(CH_2NHMe)CH_2CH_3$, —$CH(CH_2NHEt)CH_2CH_3$, —$CH_2CH(CH_2NH_2)CH_3$, —$CH_2CH(CH_2NHMe)CH_3$, —$CH_2CH(CH_2NHEt)CH_3$, —$CH(NH_2)(CH_2)_2NH_2$, —$CH(NHMe)(CH_2)_2NHMe$, —$CH(NHEt)(CH_2)_2NHEt$, —$CH_2CH(NH_2)CH_2NH_2$, —$CH_2CH(NHMe)CH_2NHMe$, —$CH_2CH(NHEt)CH_2NHEt$, —$CH_2CH(NH_2)(CH_2)_2NH_2$, —$CH_2CH(NHMe)(CH_2)_2NHMe$, —$CH_2CH(NHEt)(CH_2)_2NHEt$, —$CH_2CH(CH_2NH_2)_2$, —$CH_2CH(CH_2NHMe)_2$ and —$CH_2CH(CH_2NHEt)_2$.

Non-limiting examples of hydroxy-substituted alkyl include —$CH_2OH$, —$(CH_2)_2OH$, —$(CH_2)_3OH$, —$CH_2CH(OH)CH_3$, —$(CH_2)_4OH$, —$CH(CH_2OH)CH_2CH_3$, —$CH_2CH(CH_2OH)CH_3$, —$CH(OH)(CH_2)_2OH$, —$CH_2CH(OH)CH_2OH$, —$CH_2CH(OH)(CH_2)_2OH$ and —$CH_2CH(CH_2OH)_2$.

Non-limiting examples of fluoro-substituted alkyl include —$CH_2F$, —$CHF_2$, —$CF_3$, —$(CH_2)_2F$, —$(CHF)_2H$, —$(CHF)_2F$, —$C_2F_5$, —$(CH_2)_3F$, —$(CHF)_3H$, —$(CHF)_3F$, —$C_3F_7$, —$(CH_2)_4F$, —$(CHF)_4H$, —$(CHF)_4F$ and —$C_4F_9$.

Non-limiting examples of hydroxyl- and fluoro-substituted alkyl include —$CHFCH_2OH$, —$CF_2CH_2OH$, —$(CHF)_2CH_2OH$, —$(CF_2)_2CH_2OH$, —$(CHF)_3CH_2OH$, —$(CF_2)_3CH_2OH$, —$(CH_2)_3OH$, —$CF_2CH(OH)CH_3$, —$CF_2CH(OH)CF_3$, —$CF(CH_2OH)CHFCH_3$, and —$CF(CH_2OH)CHFCF_3$.

The term "$C_1$ to $C_4$ alkenyl or alkynyl" refers to unsaturated linear carbon chains, particularly unsubstituted carbon chains, i.e. the moiety thus referred to is constituted of carbon and hydrogen atoms only. It encompasses, but is not limited to, ethenyl (—$CHCH_2$), ethynyl (—CCH) or allyl (CH—$CHCH_2$) and but-2-enyl (—$CH_2CHCHCH_3$).

Unless explicitly stated otherwise, the following letters, when contained as capital lettering in a formula, refer to atoms: H hydrogen, C carbon F fluorine, N nitrogen, O oxygen, S sulphur, P phosphorus. CHO designates a formyl moiety. $NHCONH_2$ designates a ureido moiety.

A first aspect of the disclosure relates to a compound characterized by a general formula (100)

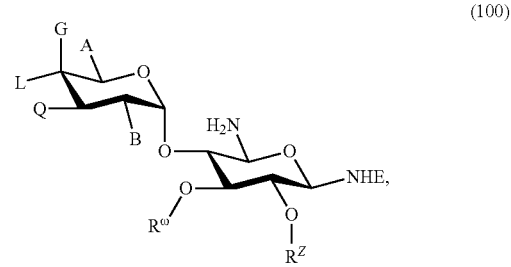

(100)

wherein
i. A is selected from
$CH_2OH$, $CH_2NH_2$ and $CH_2NHR^0$, or from
$C R^1_2OH$, $C R^1_2NH_2$ and $C R^1_2NHR^0$, or from
(R)—$CH(OH)R^1$, (R)—$CH(NH_2)R^1$, (R)—$CH(NHR^0)R^1$, (S)—$CH(OH)R^1$, (S)—$CH(NH_2)R^1$, and (S)—$CH(NHR^0)R^1$, wherein $R^0$ is selected from the group consisting of methyl, ethyl, 2-aminoethyl, 2-hydroxyethyl, $CH_2CH_2NHR$, $CH_2CH_2F$, $CH_2CHF_2$, $(CH_2)_nCF_3$, and each $R^1$ is selected independently from the group consisting of methyl, ethyl, aminomethyl, hydroxymethyl, 2-aminoethyl, 2-hydroxyethyl, $CH_2NHR$, $(CH_2)_nCH_2F$, $(CH_2)_nCHF_2$, $(CH_2)_nCF_3$, wherein n is 1 or 2, a $C_2$ to $C_4$ alkenyl and a $C_2$ to $C_4$ alkynyl, with each R independently being selected from the group of unsubstituted $C_1$ to $C_4$ alkyl, wherein G is H and L is O—$R^{A'}$, S—$R^{A'}$ or $R^{A'}$, with $R^{A'}$ being selected from H and unsubstituted, fluoro-, amino- and/or hydroxysubstituted $C_1$ to $C_4$ alkyl, or G is F and L is H or $C_1$ to $C_4$ alkyl; or ii. A and L are connected via a moiety —$CR^5_2$— and L is —O— or —$CR^5_2$—, wherein each $R^5$ is independently being from H, F and $R^1$, or $R^5_2$ signifies an oxygen atom connected to the C of one moiety —$CR^5$— in the chain by a double bond (—$CR^5$— is a carbonyl —CO—); with the proviso that $R^5$ is not F on a carbon linked to a heteroatom (selected from O, N, S); and A is selected from (R)—CH(OH), (R)—$CH(NH_2)$, (R)—$CH(NHR^0)$, (S)—CH(OH), (S)—$CH(NH_2)$, (S)—$CH(NHR^0)$, (R)—$C(OH)R^1$, (R)—$C(NH_2)R^1$, (R)—$C(NHR^0)R^1$, (S)—$C(OH)R^1$, (S)—$C(NH_2)R^1$, and (S)—$C(NHR^0)R^1$, (A and L together form a four-membered moiety substituted by oxygen or amine nitrogen on the carbon in A, and optionally substituted in any other position of the bridge connecting carbon 4 and 5 of the ring, forming a five membered ring)

wherein $R^0$ is selected from the group consisting of methyl, ethyl, 2-aminoethyl, 2-hydroxyethyl, $CH_2CH_2NHR$, $CH_2CH_2F$, $CH_2CHF_2$, $(CH_2)_nCF_3$, and each R¹ is selected independently from the group consisting of methyl, ethyl, aminomethyl, hydroxymethyl, 2-aminoethyl, 2-hydroxyethyl, CH₂NHR, (CH₂)ₙCH₂F, (CH₂)ₙCHF₂. (CH₂)ₙCF₃, wherein n is 1 or 2, and wherein each R is independently selected from the group of unsubstituted C₁ to C₄ alkyl, and G is H, or iii. A and L are connected via a moiety —CR⁵— and L is O, S or CR⁵₂, and G is H wherein each R⁵ is independently being from H, F and R¹, or R⁵₂ signifies an oxygen atom connected to the C of one moiety —CR⁵— in the chain by a double bond (—CR⁵— is a carbonyl —CO—); with the proviso that R⁵ is not F on a carbon linked to a heteroatom (selected from O, N, S); (particularly wherein L is O) and A is selected from (R)—CH(OH), (R)—CH(NH₂), (R)—CH(NHR⁰), (S)—CH(OH), (S)—CH(NH₂), (S)—CH(NHR⁰), (R)—C(OH)R¹, (R)—C(NH₂)R¹, (R)—C(NHR⁰)R¹, (S)—C(OH)R¹, (S)—C(NH₂)R¹, and (S)—C(NHR⁰)R¹, (A and L together form a propylene or O-ethylene moiety substituted by oxygen or amine nitrogen on the carbon in A, and optionally substituted in any other position of the bridge connecting carbon 4 and 5 of the ring, forming a five membered ring) wherein R⁰ is selected from the group consisting of methyl, ethyl, 2-aminoethyl, 2-hydroxyethyl, CH₂CH₂NHR, CH₂CH₂F, CH₂CHF₂, (CH₂)ₙCF₃, and each R¹ is selected independently from the group consisting of methyl, ethyl, aminomethyl, hydroxymethyl, 2-aminoethyl, 2-hydroxyethyl, CH₂NHR, (CH₂)ₙCH₂F, (CH₂)ₙCHF₂, (CH₂)ₙCF₃, wherein n is 1 or 2, and wherein each R is independently selected from the group of unsubstituted C₁ to C₄ alkyl, or iv. A and L together form a five-membered bridge connecting the 4' and 5' carbon of ring I, and G is H, wherein three or four members proximal to the 4' carbon are —CR⁵₂—, with one member optionally selected from —O—, —S—, —SO—, —SO₂—, and —NHR⁰—, (particularly wherein L is O, and L is connected to the 5' carbon via —(CR⁵₂)₄—),
wherein each R⁵ is independently being from H, F and R¹, or R⁵₂ signifies an oxygen atom connected to the C of one moiety —CR⁵— in the chain by a double bond (—CR⁵— is a carbonyl —CO—, particularly a carbonyl adjacent to an —O—, —S—, or NHR⁰—, thereby forming a lactone, thiolactone or lactame); with the proviso that R⁵ is not F on a carbon linked to a heteroatom (selected from O, N, S);
and wherein optionally, two adjacent carbon members form a double bond —CR⁵=CR⁵—, and the member positioned proximal to the 5' carbon of ring I A is selected from (R)—CH(OH), (R)—CH(NH₂), (R)—CH(NHR⁰), (S)—CH(OH), (S)—CH(NH₂), (S)—CH(NHR⁰), (R)—C(OH)R¹, (R)—C(NH₂)R¹, (R)—C(NHR⁰)R¹, (S)—C(OH)R¹, (S)—C(NH₂)R¹, and (S)—C(NHR⁰)R¹,
wherein R⁰ is selected from the group consisting of methyl, ethyl, 2-aminoethyl, 2-hydroxyethyl, CH₂CH₂NHR, CH₂CH₂F, CH₂CHF₂, (CH₂)ₙCF₃, and each R¹ is selected independently from the group consisting of methyl, ethyl, aminomethyl, hydroxymethyl, 2-aminoethyl, 2-hydroxyethyl, CH₂NHR, (CH₂)ₙCH₂F, (CH₂)ₙCHF₂, (CH₂)ₙCF₃, wherein n is 1 or 2, and wherein each R is independently selected from the group of unsubstituted C₁ to C₄ alkyl, and wherein a. for i-iv, R^Z is H or 2-aminoethyl, and R^ω is characterized by a general formula (200) or (201)

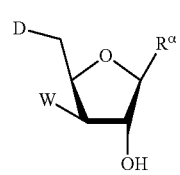
(200)

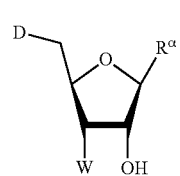
(201)

wherein R^α designates the bond linking the moiety to moiety (100);
D is selected from NH₂, OH, H, and NHR⁴, wherein R⁴ is selected from CHO, CONH₂, CONHOH, and amino- and/or hydroxy-substituted C₁ to C₆ alkyl, particularly where D is NHR⁴ and R⁴ is selected from CHO, CONH₂, CONHOH, COCH₂NH₂; COCH(NH₂)(CH₂)₄NH₂, or COCH(NH₂)(CH₂)₃NHC(NH)NH₂, and amino-substituted or hydroxy-substituted methyl, ethyl, n- or iso-propyl; more particularly where D is NHCHO or NHCONH₂, and
W is selected from OH, F, H, —O(CH₂)₂NH₂, —O(CH₂)₂NH(CH₂)₃NH₂, O—(CH₂)₂—N-morpholino, O—(CH₂)₂—N-piperidono, O—(CH₂)₂—N—[(CH₂)₂OH]₂ and a moiety characterized by formula (300) or (301)

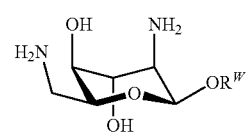
(300)

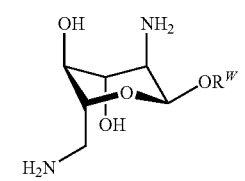
(301)

wherein R^W designates the bond linking the moiety to moiety (200) or (201), or
b. for i-ii, R^ω is H and R^Z is characterized by a general formula (400), (401), or (402):

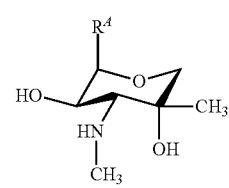
(400)

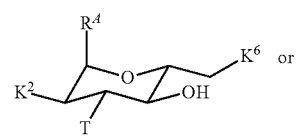
(401)

-continued

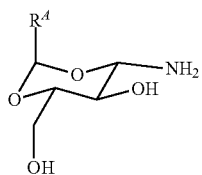
(402)

wherein $R^A$ designates the bond linking the moiety to moiety (100), and T is OH or H, and $K^2$ and $K^6$ are selected from OH and $NH_2$, or c. for i-ii, $R^\omega$ and $R^Z$ are both H, with the proviso for i-ii, that the molecule is not described by the following combination of parameters:

A is $CH_2OH$ or $CH_2NH_2$, B is $NH_2$, $R^Z$ is H and $R^\square$ is (201), and D is OH, or A is $CH_2OH$ or $CH_2NH_2$, and B is OH, and $R^\square$ is H and $R^Z$ is any one of (400), (401), and (402)

A is $CH_2NH_2$, and B is $NH_2$, OH or H, and $R^\square$ is H and $R^Z$ is H;

A is $CH_2OH$, B is 2'-N-ethyl, $R^Z$ is H, $R^\square$ is (200) and D is OH;

A is $CH_2NH_2$, B is OH, $R^Z$ is H, $R^\square$ is (200) and D is OH.

and wherein

B is selected from $NH_2$, OH, H, and $NHR^2$,
wherein $R^2$ is selected from —CHO, —$CONH_2$, substituted or unsubstituted $C_1$ to $C_6$ alkyl, and $COR^{2A}$,
wherein $R^{2A}$ is an amino-substituted $C_1$ to $C_6$ alkyl, particularly wherein B is $NHR^2$ and $R^2$ is —CHO, —$CONH_2$, an unsubstituted or amino-substituted methyl, ethyl, n- or iso-propyl, $COCH_2NH_2$; $COCH(NH_2)(CH_2)_4NH_2$, or $COCH(NH_2)(CH_2)_3NHC(NH)NH_2$,
more particularly wherein B is $NHR^2$ and $R^2$ is —CHO, methyl, ethyl, or propyl;

Q is selected from OH, $NH_2$, F and H, particularly Q is OH or H;

E is selected from H, CO—$R^3$, $CONHR^3$ and $CON(OH)R^3$, wherein $R^3$ is H or $C_1$ to $C_6$ substituted or unsubstituted alkyl (particularly a $C_1$ to $C_3$ alkyl bearing $NH_2$ and/or OH moieties), particularly wherein E is selected from (S)-4-amino-2-hydroxybutyryl, (S)-3-amino-2-hydroxypropionyl, —$CON(OH)(CH_2)_2NH_2$), (2R,3S)-2-hydroxy-4,5-diaminopentanoyl, and (2S,3R)-2,5-dihydroxy-4-aminopentanoyl.

A first sub aspect of the first aspect of the disclosure relates to a compound characterized by a general formula (100)

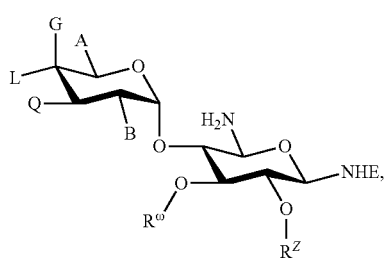
(100)

wherein
A is selected from
$CH_2OH$, $CH_2NH_2$ and $CH_2NHR^0$, or from
C $R^1_2OH$, C $R^1_2NH_2$ and C $R^1_2NHR^0$, or from
(R)—$CH(OH)R^1$, (R)—$CH(NH_2)R^1$, (R)—$CH(NHR^0)R^1$, (S)—$CH(OH)R^1$, (S)—$CH(NH_2)R^1$, and (S)—$CH(NHR^0)R^1$, wherein $R^0$ is selected from the group consisting of methyl, ethyl, 2-aminoethyl, 2-hydroxyethyl, $CH_2CH_2NHR$, $CH_2CH_2F$, $CH_2CHF_2$, $(CH_2)_nCF_3$, and each $R^1$ is selected independently from the group consisting of methyl, ethyl, aminomethyl, hydroxymethyl, 2-aminoethyl, 2-hydroxyethyl, $CH_2NHR$, $(CH_2)_nCH_2F$, $(CH_2)_nCHF_2$, $(CH_2)_nCF_3$, wherein n is 1 or 2, a $C_2$ to $C_4$ alkenyl and a $C_2$ to $C_4$ alkynyl, with each R independently being selected from the group of unsubstituted CM to $C_4$ alkyl, wherein G is H and L is O—$R^{A'}$, S—$R^{A'}$ or $R^{A'}$, with $R^{A'}$ being selected from H and unsubstituted, fluoro-, amino- and/or hydroxysubstituted $C_1$ to $C_4$ alkyl, or G is F and L is H or $C_1$ to $C_4$ alkyl;

or

A and L together form a four-membered mono- or oligoamino-, hydroxy- and/or fluoro-substituted alkyl or O-alkyl chain bridging the 4' and 5' carbon atoms of ring I, thereby forming a six-membered ring, wherein the 6' C in position (the 6' carbon linked to the 5' carbon of ring I) is selected from (R)—CH(OH), (R)—$CH(NH_2)$, (R)—$CCH_3(OH)$, (R)—$CCH_3(NH_2)$; (S)—CH(OH), (S)—$CH(NH_2)$; (S)—$CCH_3(OH)$, and (S)—$CCH_3(NH_2)$, and G is H, in other words, A and L are connected via a moiety —$CR^5_2$— and L is —O— or —$CR^5_2$—, in other words, the 4' and 5' carbon are connected by a bridge $(4'C)-L-CR^5_2-CR^5_2-A-(5'C)$,
wherein each $R^5$ is independently being from H, F and $R^1$, and A is selected from (R)—CH(OH), (R)—$CH(NH_2)$, (R)—$CH(NHR^0)$, (S)—CH(OH), (S)—$CH(NH_2)$, (S)—$CH(NHR^0)$, (R)—$C(OH)R^1$, (R)—$C(NH_2)R^1$, (R)—$C(NHR^0)R^1$, (S)—$C(OH)R^1$, (S)—$C(NH_2)R^1$, and (S)—$C(NHR^0)R^1$, (A and L together form a four-membered moiety substituted by oxygen or amine nitrogen on the carbon in A, and optionally substituted in any other position of the bridge connecting carbon 4 and 5 of the ring, forming a five membered ring)

wherein $R^0$ is selected from the group consisting of methyl, ethyl, 2-aminoethyl, 2-hydroxyethyl, $CH_2CH_2NHR$, $CH_2CH_2F$, $CH_2CHF_2$, $(CH_2)_nCF_3$, and each $R^1$ is selected independently from the group consisting of methyl, ethyl, aminomethyl, hydroxymethyl, 2-aminoethyl, 2-hydroxyethyl, $CH_2NHR$, $(CH_2)_nCH_2F$, $(CH_2)_nCHF_2$, $(CH_2)_nCF_3$, wherein n is 1 or 2, and wherein each R is independently selected from the group of unsubstituted $C_1$ to $C_4$ alkyl, and G is H, and wherein B is selected from $NH_2$, OH, H, and $NHR^2$, wherein $R^2$ is selected from —CHO, —$CONH_2$, substituted or unsubstituted $C_1$ to $C_6$ alkyl, and $COR^{2A}$, wherein $R^{2A}$ is an aminosubstituted $C_1$ to $C_6$ alkyl, particularly wherein B is $NHR^2$ and $R^2$ is —CHO, —$CONH_2$, an unsubstituted or aminosubstituted methyl, ethyl, n- or iso-propyl, $COCH_2NH_2$ (B is glycinyl); $COCH(NH_2)(CH_2)_4NH_2$ (B is lysinyl), or $COCH(NH_2)(CH_2)_3NHC(NH)NH_2$ (B is arginyl), more particularly wherein B is $NHR^2$ and $R^2$ is —CHO, methyl, ethyl, or propyl;

Q is selected from OH, $NH_2$, F and H, particularly Q is OH or H;

E is selected from H, CO—$R^3$, $CONHR^3$ and $CON(OH)R^3$, wherein $R^3$ is H or a $C_1$ to $C_6$ substituted or unsubstituted alkyl (particularly a $C_1$ to $C_3$ alkyl bearing $NH_2$ and/or OH moieties), particularly wherein E is selected from (S)-4-amino-2-hydroxybutyryl, (S)-3-amino-2-hydroxypropionyl, —CON(OH)(CH$_2$)$_2$NH$_2$), (2R,3S)-2-hydroxy-4,5-diaminopentanoyl, and (2S,3R)-2,5-dihydroxy-4-aminopentanoyl, and a. R$^Z$ is H or 2-aminoethyl, and R$^\omega$ is characterized by a general formula (200) or (201)

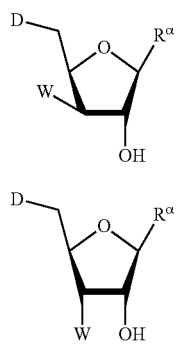

(200)

(201)

wherein R$^\alpha$ designates the bond linking the moiety to the oxygen designated OR$^\omega$ of moiety (100);

D is selected from NH$_2$, OH, H, and NHR$^4$, wherein R$^4$ is selected from CHO, CONH$_2$, CONHOH, and amino- and/or hydroxy-substituted C$_1$ to C$_6$ alkyl, particularly where D is NHR$^4$ and R$^4$ is selected from CHO, CONH$_2$, CONHOH, COCH$_2$NH$_2$ (D is glycinyl); COCH(NH$_2$)(CH$_2$)$_4$NH$_2$ (D is lysinyl), or COCH(NH$_2$)(CH$_2$)$_3$NHC(NH)NH$_2$ (D is arginyl), and amino-substituted or hydroxy-substituted methyl, ethyl, n- or iso-propyl; more particularly where D is NHCHO or NHCONH$_2$, and W is selected from OH, F, H, —O(CH$_2$)$_2$NH$_2$, —O(CH$_2$)$_2$NH(CH$_2$)$_3$NH$_2$, O—(CH$_2$)$_2$—N-morpholino, O—(CH$_2$)$_2$—N-piperidono, O—(CH$_2$)$_2$—N—[(CH$_2$)$_2$OH]$_2$ and a moiety characterized by formula (300) or (301)

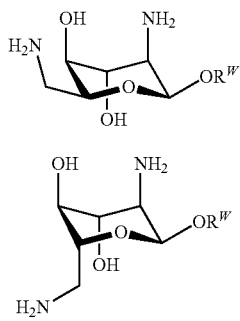

(300)

(301)

wherein R$^W$ designates the bond linking the moiety to the carbon designated W of moiety (200) or (201), or b. R$^\omega$ is H and R$^Z$ is characterized by a general formula (400), (401), or (402):

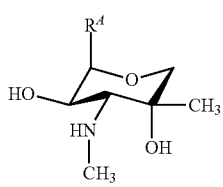

(400)

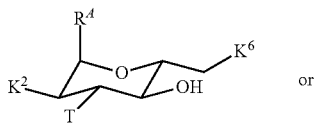

(401)

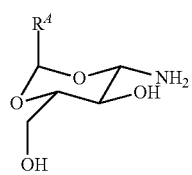

(402)

wherein R$^A$ designates the bond linking the moiety to the oxygen designated R$^Z$ of moiety (100), and T is OH or H, and K$^2$ and K$^6$ are selected from OH and NH$_2$, or c. or R$^\omega$ and R$^Z$ are both H, with the proviso that the molecule is not described by the following combination of parameters:

A is CH$_2$OH or CH$_2$NH$_2$, B is NH$_2$, R$^Z$ is H and R$^\omega$ is (201), and D is OH, or A is CH$_2$OH or CH$_2$NH$_2$, and B is OH, and R$^\omega$ is H and R$^Z$ is any one of (400), (401), and (402)

A is CH$_2$NH$_2$, and B is NH$_2$, OH or H, and R$^\omega$ is H and R$^Z$ is H.

A is CH$_2$OH, B is 2'-N-ethyl, R$^Z$ is H, R$^\omega$ is (200) and D is OH;

A is CH$_2$NH$_2$, B is OH, R$^Z$ is H, R$^\omega$ is (200) and D is OH.

Particularly preferred embodiments show a formamido or ureido moiety in position D. Alternatively, a hydroxy ureido moiety is introduced in position D to increase H-bonding capabilities. Substituted N-alkyl is possible in D also with at least one of the variations in position A or B, particularly with a six-ring formed between the 4' and 5' carbon of ring I. N-alkyl modifications in D that otherwise are unchanged natural paromomycin or neomycin type ring I are disclaimed.

Particular embodiments include compounds characterized by the general formula (110), particularly (111)

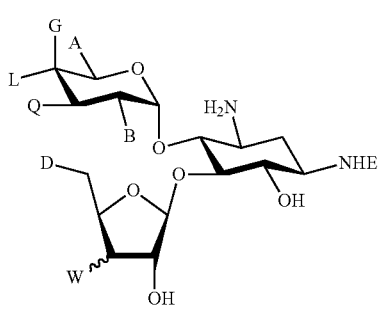

(110)

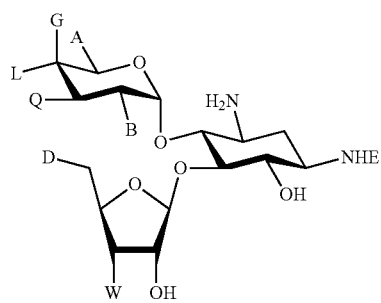
(111)

Particular embodiments include compounds characterized by the general formula (120), particularly (121)

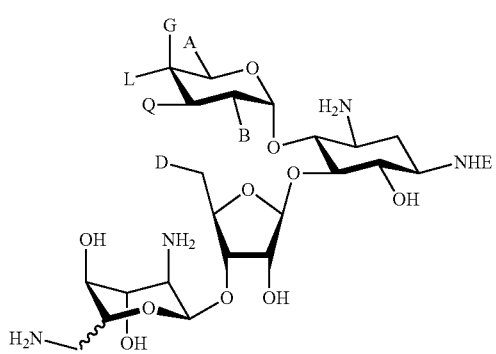
(120)

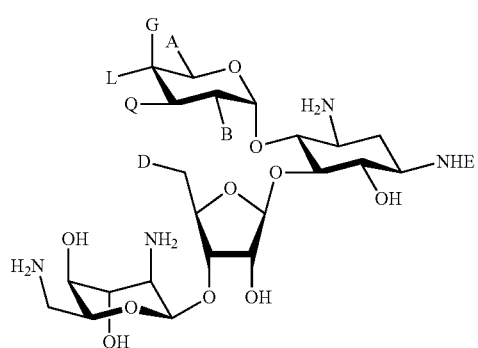
(121)

wherein A, B, D, E, G, L and Q have the same meaning as indicated above.

Particular embodiments include compounds described by a general formula (101), particularly by (102) or (102a).

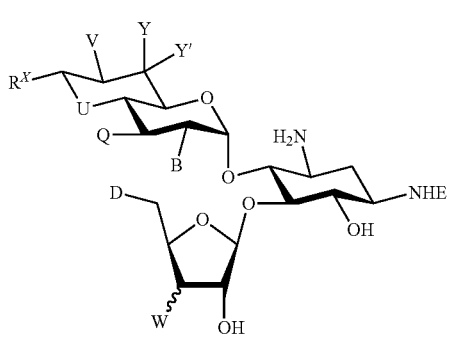
(101)

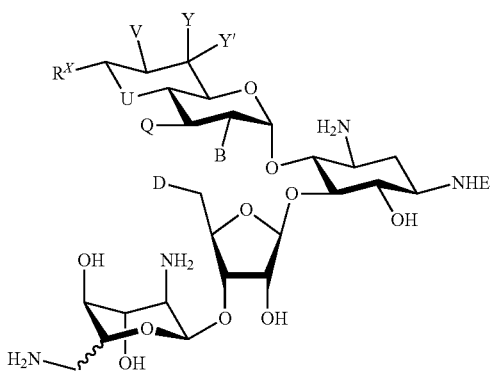
(102)

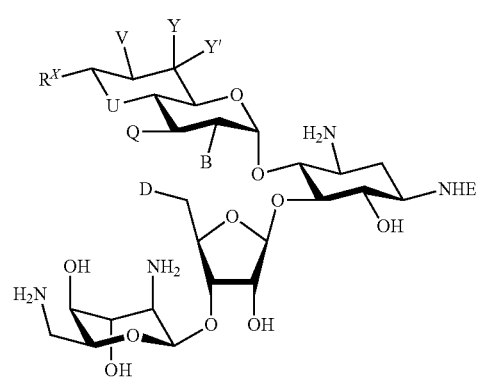
(102a)

wherein one of Y and Y' is selected from OH and $NH_2$ and the other one is H, particularly wherein Y is H and Y' is selected from OH and $NH_2$, $R^X$ is selected from H, methyl, ethyl, aminomethyl, hydroxymethyl, 2-aminoethyl, 2-hydroxyethyl, $CH_2NHR$ (with R being a $C_1$ to $C_4$ alkyl), $CH_2F$, $CHF_2$, and $CF_3$, V is selected from H, OH, $NH_2$, NHR and $NHR_2$ with R being a amino-, hydroxyl- or fluoro-substituted $C_1$ to $C_4$ alkyl, particularly $(CH_2)_nOH$, $(CH_2)_nNH_2$, $(CH_2)_nF$ with n being 2, 3 or 4, U is selected from O, S, $CH_2$, SO and $SO_2$, —CH(OH)— and —CH($NH_2$)— wherein B is selected from $NH_2$, OH, H, and $NHR^2$, wherein $R^2$ is selected from —CHO, —$CONH_2$, substituted or unsubstituted $C_1$ to $C_6$ alkyl, and $COR^{2A}$, wherein $R^{2A}$ is an amino-substituted $C_1$ to $C_6$ alkyl, particularly wherein B is $NHR^2$ and $R^2$ is —CHO, —$CONH_2$, unsubstituted or amino-substituted or hydroxy-substituted $C_1$ to $C_4$ alkyl, $COCH_2NH_2$ (B is glycinyl); $COCH(NH_2)(CH_2)_4NH_2$ (B is lysinyl), or $COCH(NH_2)(CH_2)_3NHC(NH)NH_2$ (B is arginyl), more particularly wherein B is $NHR^2$, and $R^2$ is selected from CHO, methyl, ethyl, and propyl, and wherein D, E, Q and W, where appropriate, have the meaning indicated above.

For certain countries, particularly for Europe, compounds defined according to the above formula (102a) for which $R^X$ is methyl when U is O, V is H, B is $NH_2$ and D is OH, are disclaimed. This disclaimer is not valid for the United States of America.

Particular embodiments include compounds described by a general formula (103), particularly by (104) or (104a)

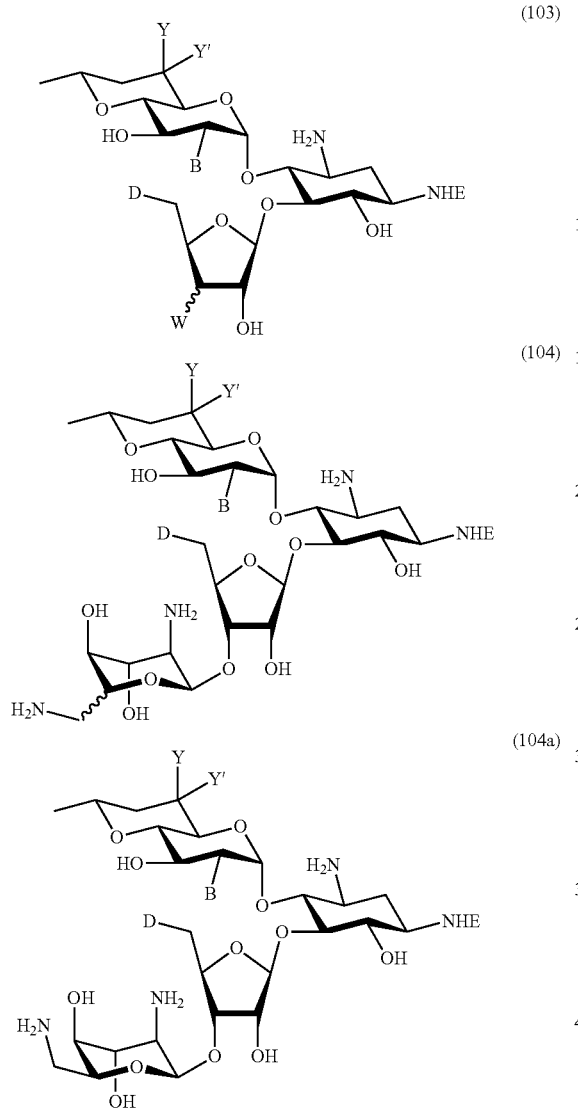

(103)
(104)
(104a)

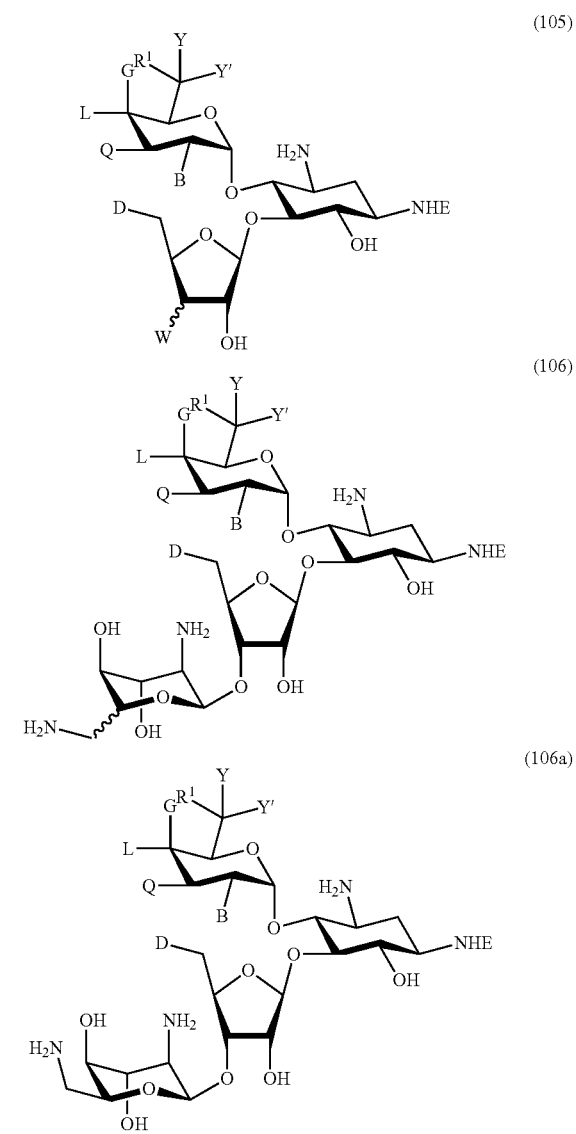

(105)
(106)
(106a)

wherein one of Y and Y' is selected from OH, $NH_2$ and $CH_2NHR^0$, and the other one is H, wherein $R^0$ has the same meaning as indicated in the first aspect, particularly wherein $R^0$ is selected from methyl, ethyl, 2-aminoethyl and 2-hydroxyethyl, W, where appropriate, has the same meaning as indicated in the first aspect, and B is $NHR^2$, wherein $R^2$ is selected from substituted or unsubstituted $C_1$ to $C_6$ alkyl (particularly $R^2$ is an unsubstituted, amino-substituted and/or hydroxy-substituted methyl, ethyl, n- or iso-propyl), —CHO (formylamido), —$CONH_2$ (ureido), and $CO(CH_2)_nNH_2$ with n selected from 1 (glycinyl), 2 and 3, lysinyl and arginyl, and D is OH or B is $NHR^2$, wherein $R^2$ is has the meaning indicated in the previous paragraph, and D is selected from NH—CHO and NH—$CONH_2$ or D is selected from NH—CHO and NH—$CONH_2$ and B is $NH_2$.

Acetyl, propanoyl and higher acyl groups will not work in B but inclusion of amino groups in the acyl group helps to rescue the activity Particular embodiments include compounds described by a general formula (105), particularly by (106) or (106a) wherein one of Y and Y' is selected from OH, $NH_2$ and $CH_2NHR^0$, and the other one is H, wherein $R^0$ has the same meaning as indicated in claim 1, particularly one of Y and Y' is selected from OH, $NH_2$ and $CH_2NHR^0$ wherein $R^0$ is selected from methyl, ethyl, 2-aminoethyl and 2-hydroxyethyl, and the other one of Y and Y' is H or $R^1$, wherein each $R^1$ independently of any other $R^1$ has the meaning defined in claim 1, particularly Y and Y' is H or $R^1$ and each $R^1$ independently of any other $R^1$ is selected from $C_1$ to $C_3$ substituted or unsubstituted alkyl, more particularly one of Y and Y' is H and $R^1$ is an unsubstituted, amino-substituted and/or hydroxy-substituted methyl, ethyl, n- or iso-propyl), or a $C_2$ to $C_4$ alkenyl or alkynyl moiety, particularly ethenyl (—$CHCH_2$), ethynyl (C—CH) or allyl (CH—$CHCH_2$), and B, D, E, G, L, Q and W, where appropriate, have the same meaning as indicated in claim 1.

In particular embodiments, Q is OH, L is OH, G is H.

In particular embodiments, Y is selected from OH, $NH_2$ and $CH_2NHR^0$ and Y' is H (R configuration), wherein $R^0$ has the meaning indicated above.

In particular embodiments, Y is H and Y' is selected from OH, $NH_2$ and $CH_2NHR^0$ (S configuration), wherein $R^0$ has the meaning indicated above.

In particular embodiments, the compound is described by formula (106a) and
  a. R$^1$ is selected from methyl, ethyl, propyl and aminomethyl, Y is selected from NH$_2$ and OH and Y' is H (R configuration), or
  b. R$^1$ is selected from methyl, ethyl, propyl and aminomethyl, Y is H and Y' is selected from NH$_2$ and OH.

In particular embodiments, B is NH$_2$.
In particular embodiments, D is OH.
In particular embodiments, E is H.
In particular embodiments, E is selected from (S)-4-amino-2-hydroxybutyryl, (S)-3-amino-2-hydroxypropionyl, —CON(OH)(CH$_2$)$_2$NH$_2$), (2R,3S)-2-hydroxy-4,5-diaminopentanoyl, and (2S,3R)-2,5-dihydroxy-4-aminopentanoyl.
In particular embodiments, Q is OH or H, particularly Q is OH.

Particular embodiments are those wherein
  a. R$^1$ is methyl, Y is NH$_2$ and Y' is H;
  b. R$^1$ is ethyl, Y is NH$_2$ and Y' is H;
  c. R$^1$ is propyl, Y is NH$_2$ and Y' is H;
  d. R$^1$ is aminomethyl, Y is NH$_2$ and Y' is H;
  e. R$^1$ is ethenyl, Y is NH$_2$ and Y' is H;
  f. R$^1$ is ethynyl, Y is NH$_2$ and Y' is H;
  g. R$^1$ is allyl, Y is NH$_2$ and Y' is H;
  h. R$^1$ is methyl, Y is OH and Y' is H; (156)
  i. R$^1$ is ethyl, Y is OH and Y' is H;
  j. R$^1$ is propyl, Y is OH and Y' is H; (142)
  k. R$^1$ is aminomethyl, Y is OH and Y' is H;
  L. R$^1$ is ethenyl, Y is OH and Y' is H;
  m. R$^1$ is ethynyl, Y is OH and Y' is H;
  n. R$^1$ is allyl, Y is OH and Y' is H;
  o. R$^1$ is methyl, Y' is NH$_2$ and Y is H; (166)
  p. R$^1$ is ethyl, Y' is NH$_2$ and Y is H;
  q. R$^1$ is propyl, Y' is NH$_2$ and Y is H;
  r. R$^1$ is aminomethyl, Y' is NH$_2$ and Y is H;
  s. R$^1$ is ethenyl, Y' is NH$_2$ and Y is H;
  t. R$^1$ is ethynyl, Y' is NH$_2$ and Y is H;
  u. R$^1$ is allyl, Y' is NH$_2$ and Y is H;
  v. R$^1$ is methyl, Y' is OH and Y is H; (155)
  w. R$^1$ is ethyl, Y' is OH and Y is H; (189)
  x. R$^1$ is propyl, Y' is OH and Y is H; (143)
  y. R$^1$ is aminomethyl, Y' is NH$_2$ and Y is H;
  z. R$^1$ and Y are methyl and Y' is OH. (159)

Particular embodiments include compounds described by a general formula (102) or (102a)

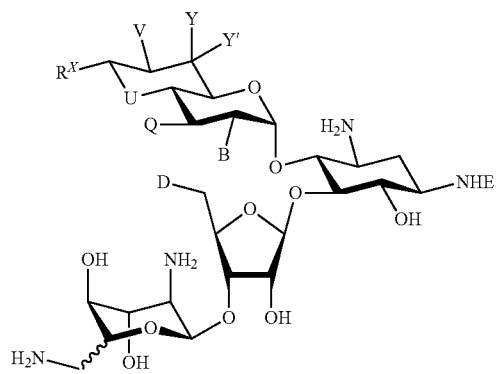

(102)

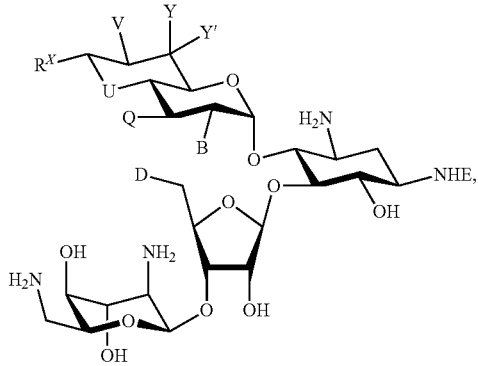

(102a)

wherein B is NH$_2$, D is OH, Q is OH, R$^X$ is H, U is O, V is H, E is H and
  a. Y is H and Y' is OH (210) or
  b. Y is OH and Y' is H (211).

or B is NH$_2$, D is OH, Q is OH, R$^X$ is methyl, U is O, E is H, V is H and
  c. Y is H and Y' is OH (125)
  d. Y is H and Y' is NH$_2$ (139)
  e. Y is OH and Y' is H (109)
  f. Y is H and Y' is NH$_2$ (150)

Particular embodiments are also those compounds wherein B is NHR$^2$, wherein R$^2$ is selected from —CHO, —CONH$_2$, C$_1$ to C$_6$ substituted or unsubstituted alkyl, particularly wherein R$^2$ is —CHO, —CONH$_2$ or an unsubstituted methyl, ethyl, or propyl.

Other particular embodiments are those compounds wherein B is NH$_2$.

In particular embodiments thereof, D is selected from NHCHO (formamide), NHCONH$_2$ (ureide), —NHCONHOH and NHR$^4$, wherein R$^4$ is selected from C$_1$ to C$_4$ unsubstituted alkyl and C$_1$ to C$_4$ aminosubstituted alkyl.

In particular embodiments thereof, D is OH.

Particular embodiments include compounds described by a general formula (107), particularly by (108) or (108a)

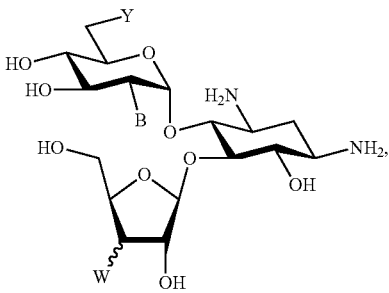

(107)

-continued

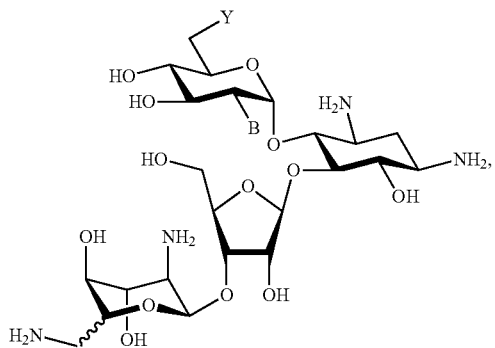
(108)

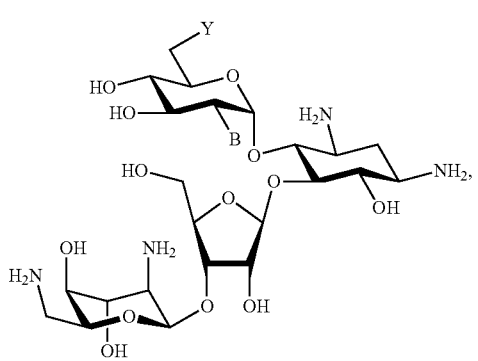
(109)

wherein W has the meaning indicated above, Y is selected from OH, NH₂ and NHR⁰, wherein R⁰ is selected from the group consisting of methyl, ethyl, aminomethyl, hydroxymethyl, 2-aminoethyl, 2-hydroxyethyl, CH₂NHR (with R being an unsubstituted $C_1$ to $C_4$ alkyl), and B is selected from H, OH, NHCHO (formamido), NHCOCH₂NH₂ (glycinyl), lysinyl, arginyl and NHR², wherein R² is selected from unsubstituted, amino-substituted and/or hydroxy-substituted $C_1$ to $C_4$ alkyl, or from $COR^{2A}$, wherein $R^{2A}$ is an amino-substituted $C_1$ to $C_4$ alkyl, particularly wherein a. B is OH and Y is OH (118)
b. B is NHCH₃ and Y is OH (115)
c. B is NHCH₂CH₃ and Y is OH (127)
d. B is NH(CH₂)₂CH₃ and Y is OH (128)
e. B is H and Y is NH₂ (173)
f. B is OH and Y is NH₂ (119)
g. B is NHCH₃ and Y is NH₂ (171)
h. B is NHCH₂CH₃ and Y is NH₂ (172)
i. B is NHCO and Y is NH₂ (182)
j. B is NHCOCH₂NH₂ and Y is NH₂ (175)

The following compounds are similarly encompassed:
a. 5"-deoxy-5"-formamidoparomomycin (137)
b. 5"-deoxy-5"-ureidoparomomycin (141)
c. 3',5"-dideoxy-5"-formamidoparomomycin (153)

Particular embodiments include the compounds:

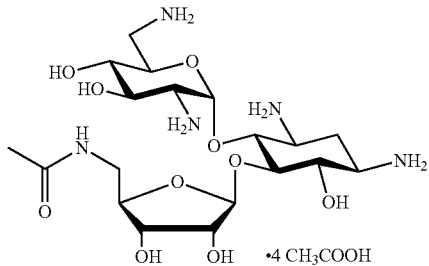
(129)

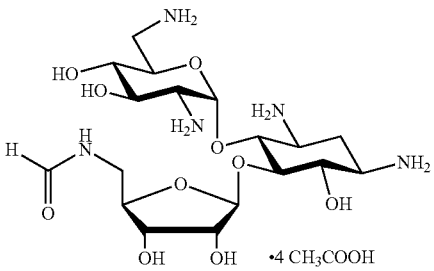
(130)

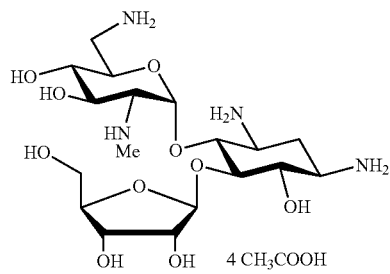
(DC100)

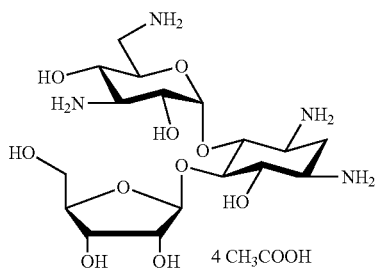
(064)

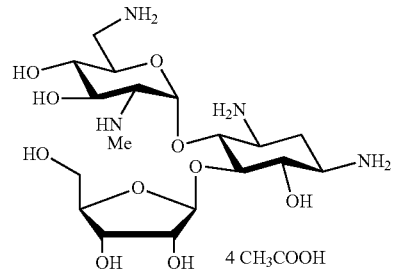

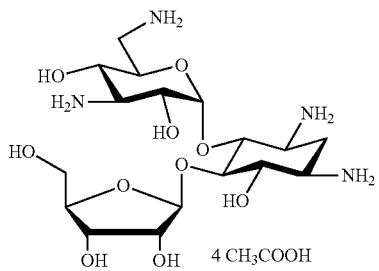
(034)

-continued
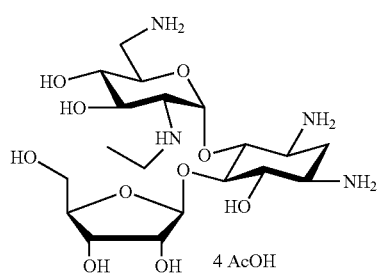
(037)
4 AcOH
(the acetic acid content is not part of the definition of the compound)
Particular embodiments include the compounds:
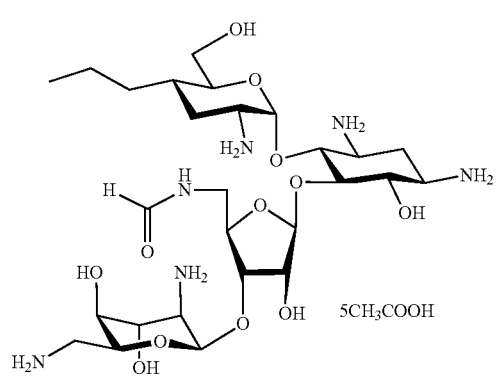
(190)
5CH₃COOH
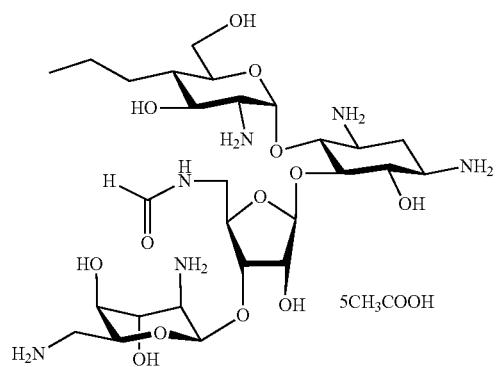
(194)
5CH₃COOH
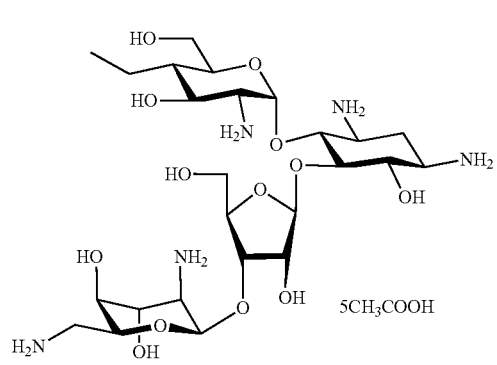
(206)
5CH₃COOH
-continued
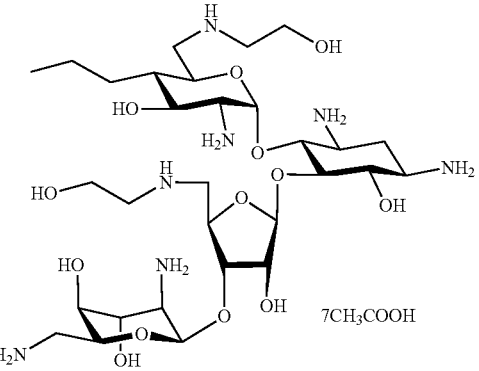
(193)
7CH₃COOH
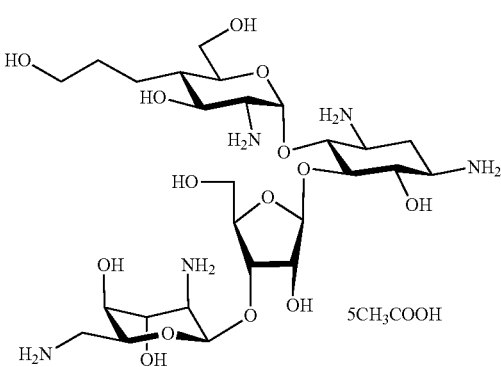
(195)
5CH₃COOH
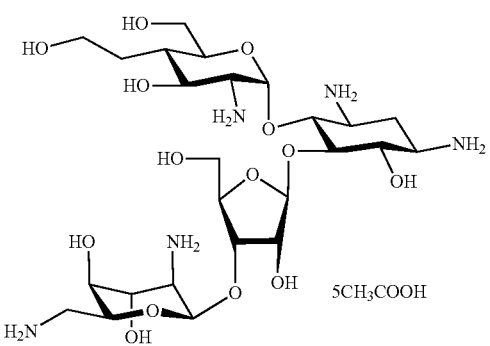
(197)
5CH₃COOH
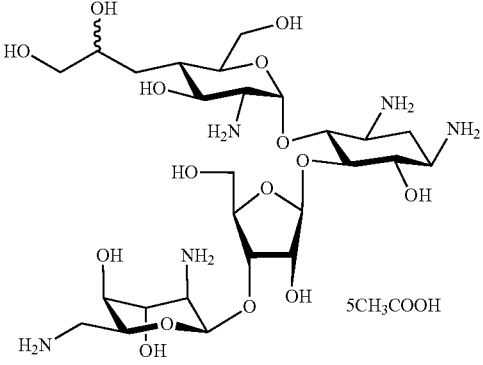
(198)
5CH₃COOH -continued

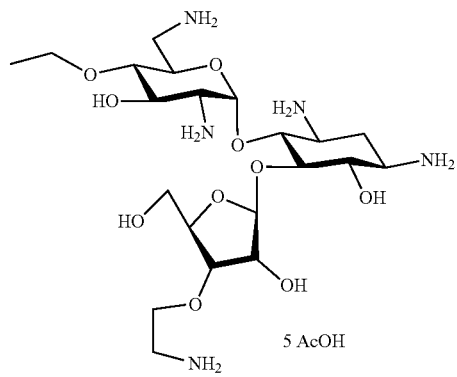
(073)
5 AcOH

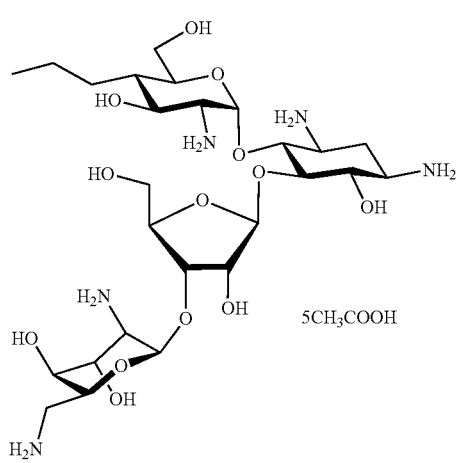
(079)
5CH₃COOH

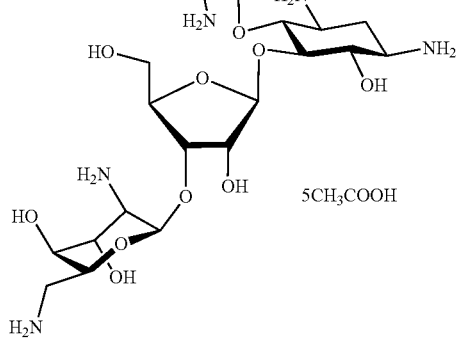
(116)
5CH₃COOH

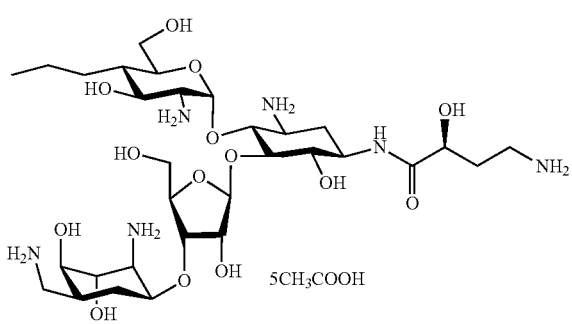
(187)
5CH₃COOH

-continued

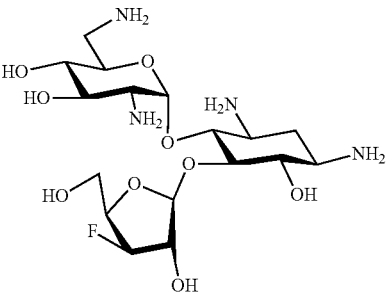
(083)

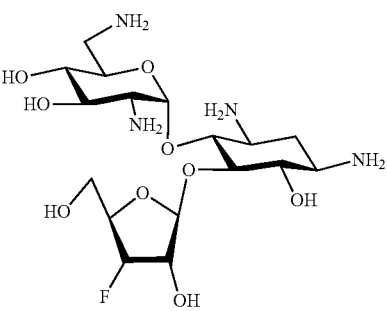
(093)

A second sub aspect of the first aspect of the invention relates to a compound being characterized by a general formula (100)

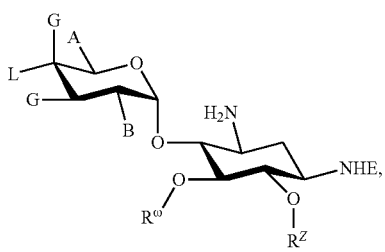
(100)

wherein
A and L are connected via a moiety —CR⁵— and L is O, S or CR⁵₂, and G is H
wherein each R⁵ is independently being from H, F and R¹, or R⁵₂ signifies an oxygen atom connected to the C of one moiety —CR⁵— in the chain by a double bond (—CR⁵— is a carbonyl —CO—);
with the proviso that R⁵ is not F on a carbon linked to a heteroatom (selected from O, N, S);
(particularly wherein L is O) and
A is selected from (R)—CH(OH), (R)—CH(NH₂), (R)—CH(NHR⁰), (S)—CH(OH), (S)—CH(NH₂), (S)—CH(NHR⁰), (R)—C(OH)R¹, (R)—C(NH₂)R¹, (R)—C(NHR⁰)R¹, (S)—C(OH)R¹, (S)—C(NH₂)R and (S)—C(NHR⁰)R¹, (A and L together form a propylene or O-ethylene moiety substituted by oxygen or amine nitrogen on the carbon in A, and optionally substituted in any other position of the bridge connecting carbon 4 and 5 of the ring, forming a five membered ring)
wherein R⁰ is selected from the group consisting of methyl, ethyl, 2-aminoethyl, 2-hydroxyethyl, CH₂CH₂NHR, CH₂CH₂F, CH₂CHF₂, (CH₂)ₙCF₃, and each R¹ is selected independently from the group consisting of methyl, ethyl, aminomethyl, hydroxymethyl, 2-aminoethyl, 2-hydroxyethyl, CH$_2$NHR, (CH$_2$)$_n$CH$_2$F, (CH$_2$)$_n$CHF$_2$, (CH$_2$)$_n$CF$_3$, wherein n is 1 or 2, and wherein each R is independently selected from the group of unsubstituted C$_1$ to C$_4$ alkyl, and wherein B is selected from NH$_2$, OH, H, and NHR$^2$, wherein R$^2$ is selected from —CHO, —CONH$_2$, substituted or unsubstituted C$_1$ to C$_6$ alkyl, and COR$^{2A}$, wherein R$^{2A}$ is an amino-substituted C$_1$ to C$_6$ alkyl, particularly wherein B is NHR$^2$ and R$^2$ is —CHO, —CONH$_2$, an unsubstituted or amino-substituted methyl, ethyl, n- or iso-propyl, COCH$_2$NH$_2$; COCH(NH$_2$)(CH$_2$)$_4$NH$_2$, or COCH(NH$_2$)(CH$_2$)$_3$NHC(NH)NH$_2$, more particularly wherein B is NHR$^2$ and R$^2$ is —CHO, methyl, ethyl, or propyl;

Q is selected from OH, NH$_2$, F and H, particularly Q is OH or H;

E is selected from H, CO—R$^3$, CONHR$^3$ and CON(OH)R$^3$, wherein R$^3$ is H or a C$_1$ to C$_6$ substituted or unsubstituted alkyl (particularly a C$_1$ to C$_3$ alkyl bearing NH$_2$ and/or OH moieties), particularly wherein E is selected from (S)-4-amino-2-hydroxybutyryl, (S)-3-amino-2-hydroxypropionyl, —CON(OH)(CH$_2$)$_2$NH$_2$), (2R,3S)-2-hydroxy-4,5-diaminopentanoyl, and (2S,3R)-2,5-dihydroxy-4-aminopentanoyl, and R$^Z$ is H or 2-aminoethyl, and R$^\omega$ is characterized by a general formula (200) or (201)

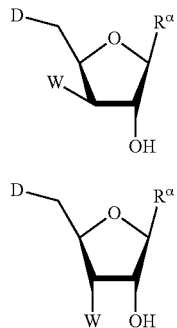

(200)

(201)

wherein R$^\alpha$ designates the bond linking the moiety to the oxygen designated OR$^\omega$ of moiety (100);

D is selected from NH$_2$, OH, H, and NHR$^4$, wherein R$^4$ is selected from CHO, CONH$_2$, CONHOH, and amino- and/or hydroxy-substituted C$_1$ to C$_6$ alkyl, particularly where D is NHR$^4$ and R$^4$ is selected from CHO, CONH$_2$, CONHOH, COCH$_2$NH$_2$; COCH(NH$_2$)(CH$_2$)$_4$NH$_2$, or COCH(NH$_2$)(CH$_2$)$_3$NHC(NH)NH$_2$, and amino-substituted or hydroxy-substituted methyl, ethyl, n- or iso-propyl; more particularly where D is NHCHO or NHCONH$_2$, and W is selected from OH, F, H, —O(CH$_2$)$_2$NH$_2$, —O(CH$_2$)$_2$NH(CH$_2$)$_3$NH$_2$, O—(CH$_2$)$_2$—N-morpholino, O—(CH$_2$)$_2$—N-piperidono, O—(CH$_2$)$_2$—N—[(CH$_2$)$_2$OH]$_2$ and a moiety characterized by formula (300) or (301)

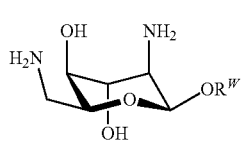

(300)

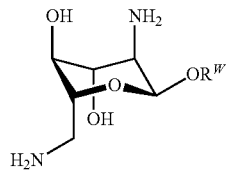

(301)

wherein R$^W$ designates the bond linking the moiety to the carbon designated W of moiety (200) or (201).

In particular embodiments, the compound is characterized by the general formula (110), particularly (111)

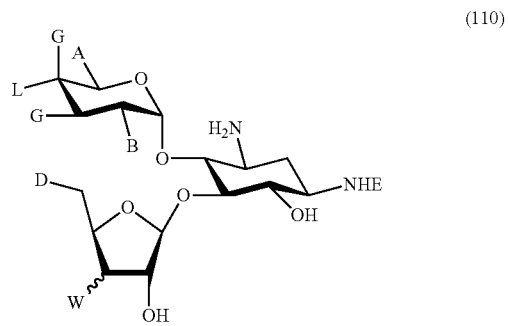

(110)

(111)

wherein A, B, D, E, G, L, Q and W have the same meanings as indicated above.

In particular embodiments, the compound is characterized by the general formula (120), particularly (121)

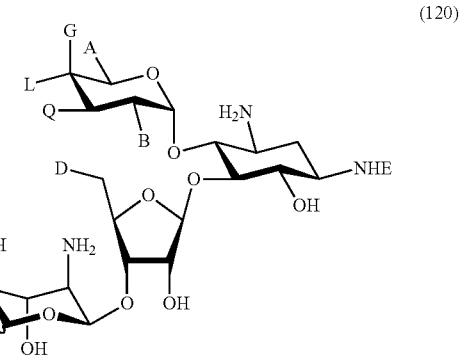

(120)

-continued

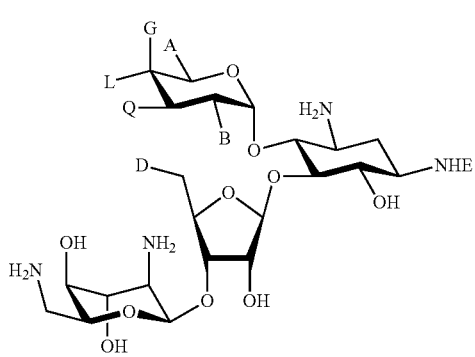
(121)

wherein A, B, D, E, G, L and Q have the same meaning as indicated above.

In particular embodiments, the compound is described by a general formula (101'), particularly by (102') or (102a')

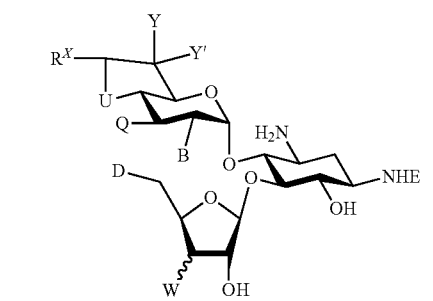
(101')

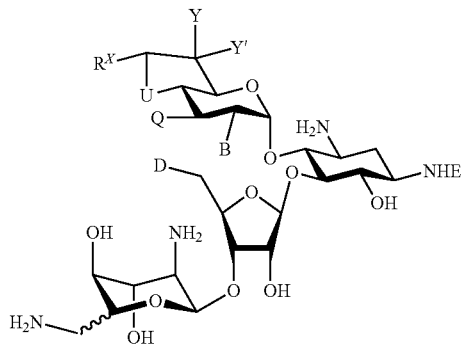
(102')

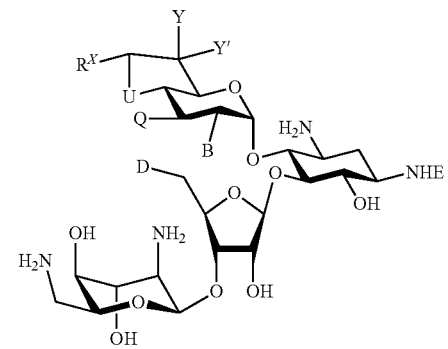
(102a')

wherein one of Y and Y' is selected from OH and NH$_2$ and the other one is H, particularly wherein Y is H and Y' is selected from OH and NH$_2$, $R^X$ is selected from H, methyl, ethyl, aminomethyl, hydroxymethyl, 2-aminoethyl, 2-hydroxyethyl, CH$_2$NHR (with R being a C$_1$ to C$_4$ alkyl), CH$_2$F, CHF$_2$, and CF$_3$, U is selected from O, S, CH$_2$, SO and SO$_2$, —CH(OH)— and —CH(NH$_2$)— wherein B is selected from NH$_2$, OH, H, and NHR$^2$, wherein R$^2$ is selected from —CHO, —CONH$_2$, substituted or unsubstituted C$_1$ to C$_6$ alkyl, and COR$^{2A}$, wherein R$^{2A}$ is an amino-substituted C$_1$ to C$_6$ alkyl, particularly wherein B is NHR$^2$ and R$^2$ is —CHO, —CONH$_2$, and unsubstituted C$_1$ to C$_4$ alkyl, more particularly wherein B is NHR$^2$, and R$^2$ is selected from CHO, methyl, ethyl, and propyl, and wherein D, E, Q and W, where appropriate, have the meaning indicated above.

In particular embodiments, the compound is described by a general formula (103'), particularly by (104') or (104a')

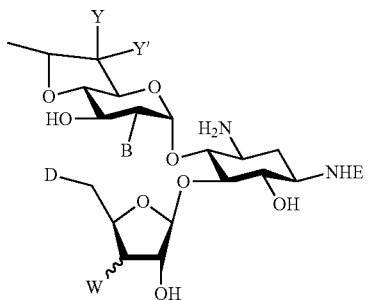
(103')

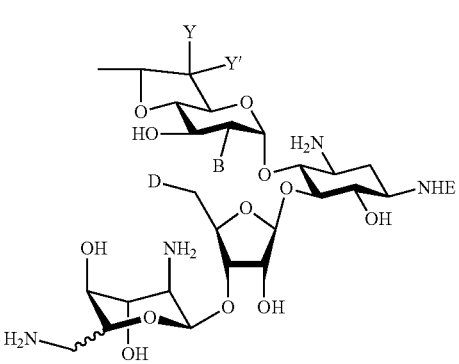
(104')

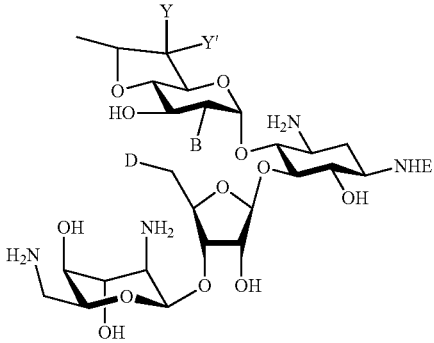
(104a')

wherein one of Y and Y' is selected from OH, NH$_2$ and CH$_2$NHR$^O$, and the other one is H, particularly wherein Y is H and Y' is selected from OH, NH$_2$ and CH$_2$NHR$^O$, wherein R$^O$ has the same meaning as indicated in the first aspect, particularly wherein R$^O$ is selected from methyl, ethyl, 2-aminoethyl and 2-hydroxyethyl, more particularly wherein Y is H and Y' is OH, W, where appropriate, has the same meaning as indicated in the first aspect, and B is NHR², wherein R² is selected from substituted or unsubstituted C₁ to C₆ alkyl (particularly R² is an unsubstituted, amino-substituted and/or hydroxy-substituted methyl, ethyl, n- or iso-propyl), —CHO, —CONH₂, and D is OH or B is NHR², wherein R² is has the meaning indicated in the previous paragraph, and D is selected from NH—CHO and NH—CONH₂ or
D is selected from NH—CHO and NH—CONH₂ and B is NH₂.

In particular embodiments, the compound is described by a general formula (103'h), particularly by (104'h) or (104a'h)

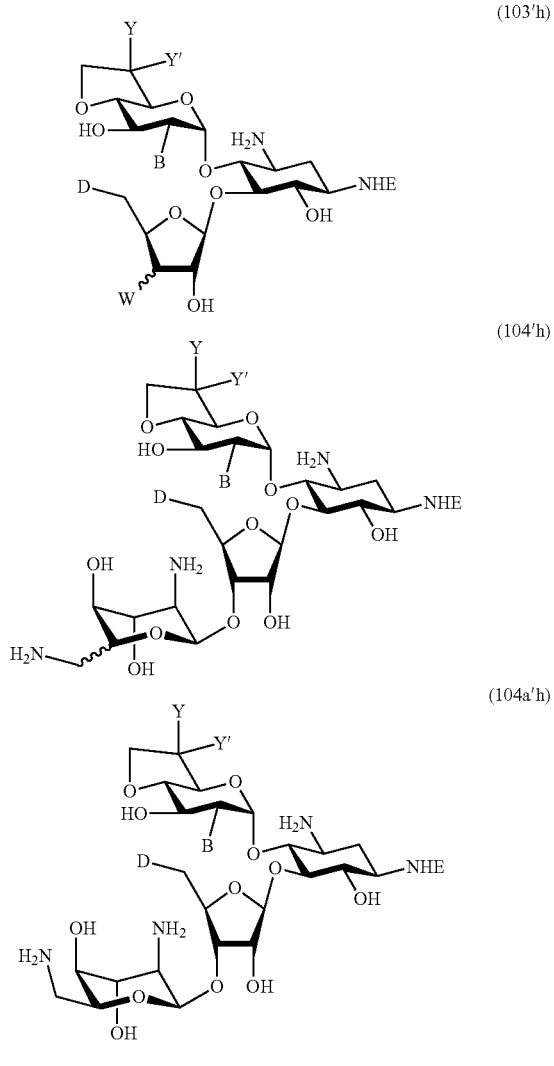

W, where appropriate, has the same meaning as indicated in the first aspect, and
B is NH₂, D is OH, E is H and
  a. Y is H and Y' is OH (203) or
  b. Y is OH and Y' is H (204).

In particular embodiments, Y is H and Y' is selected from OH, NH₂ and CH₂NHR⁰, wherein R⁰ has the same meaning as indicated in the first aspect, particularly wherein R⁰ is selected from methyl, ethyl, 2-aminoethyl and 2-hydroxyethyl, and B, D, E, G, L, Q and W, where appropriate, have the same meaning as indicated in in the first aspect.

In particular embodiments, Y' is OH.
In particular embodiments, B is NH₂.
In particular embodiments, D is OH.
In particular embodiments, E is H.
In particular embodiments, E is selected from (S)-4-amino-2-hydroxybutyryl, (S)-3-amino-2-hydroxypropionyl, —CON(OH)(CH₂)₂NH₂), (2R,3S)-2-hydroxy-4,5-diaminopentanoyl, and (2S,3R)-2,5-dihydroxy-4-aminopentanoyl.

In particular embodiments, Q is OH or H, particularly wherein Q is OH.

Particular embodiments include the compounds:

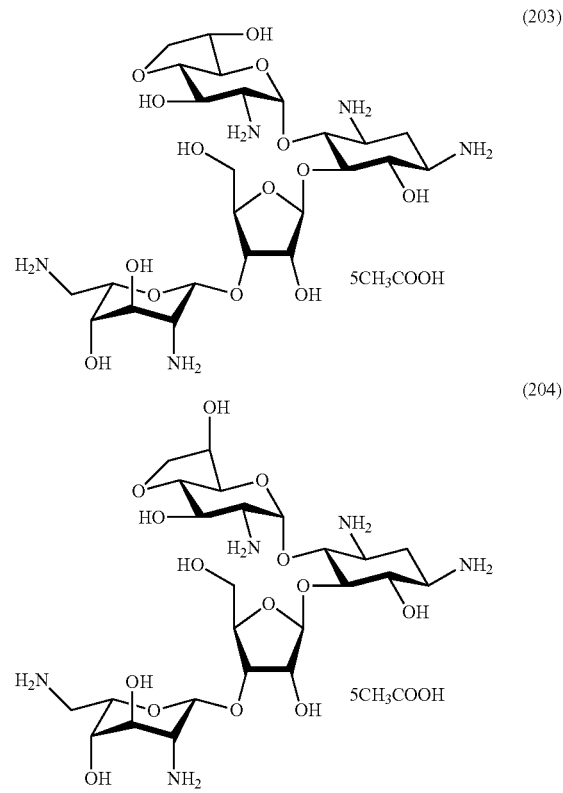

A third sub aspect of the first aspect of the invention relates to a compound being characterized by a general formula (100)

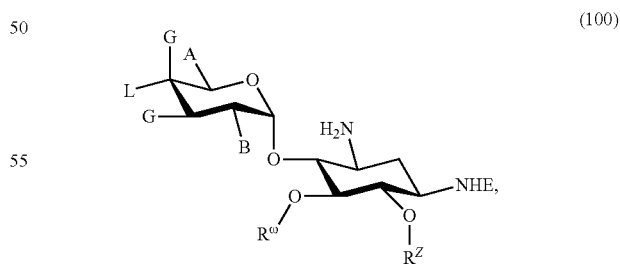

wherein
A and L together form a five-membered bridge connecting the 4' and 5' carbon of ring I, and G is H wherein three or four members proximal to the 4' carbon are —CR⁵₂—, with one member optionally selected from —O—, —S—, —SO—, —SO₂—, and —NHR⁰— (particularly wherein L is O, and L is connected to the 5' carbon via —(CR⁵₂)₄—), wherein each $R^5$ is independently being from H, F and $R^1$, or $R^5{}_2$ signifies an oxygen atom connected to the C of one moiety —$CR^5$— in the chain by a double bond (—$CR^5$— is a carbonyl —CO—, particularly a carbonyl adjacent to an —O—, —S—, or $NHR^O$—, thereby forming a lactone, thiolactone or lactame);

with the proviso that $R^5$ is not F on a carbon linked to a heteroatom (selected from O, N, S); and wherein optionally, two adjacent carbon members form a double bond —$CR^5$=$CR^5$—, and the member positioned proximal to the 5' carbon of ring I A is selected from (R)—CH(OH), (R)—CH($NH_2$), (R)—CH($NHR^O$), (S)—CH(OH), (S)—CH($NH_2$), (S)—CH($NHR^O$), (R)—C(OH)$R^1$, (R)—C($NH_2$)$R^1$, (R)—C($NHR^O$)$R^1$, (S)—C(OH)$R^1$, (S)—C($NH_2$)$R^1$, and (S)—C($NHR^O$)$R^1$, wherein $R^O$ is selected from the group consisting of methyl, ethyl, 2-aminoethyl, 2-hydroxyethyl, $CH_2CH_2NHR$, $CH_2CH_2F$, $CH_2CHF_2$, $(CH_2)_nCF_3$, and each $R^1$ is selected independently from the group consisting of methyl, ethyl, aminomethyl, hydroxymethyl, 2-aminoethyl, 2-hydroxyethyl, $CH_2NHR$, $(CH_2)_nCH_2F$, $(CH_2)_nCHF_2$, $(CH_2)_nCF_3$, wherein n is 1 or 2, and wherein each R is independently selected from the group of unsubstituted $C_1$ to $C_4$ alkyl, and wherein B is selected from $NH_2$, OH, H, and $NHR^2$, wherein $R^2$ is selected from —CHO, —$CONH_2$, substituted or unsubstituted $C_1$ to $C_6$ alkyl, and $COR^{2A}$, wherein $R^{2A}$ is an amino-substituted $C_1$ to $C_6$ alkyl, particularly wherein B is $NHR^2$ and $R^2$ is —CHO, —$CONH_2$, an unsubstituted or amino-substituted methyl, ethyl, n- or iso-propyl, $COCH_2NH_2$; $COCH(NH_2)(CH_2)_4NH_2$, or $COCH(NH_2)(CH_2)_3NHC(NH)NH_2$, more particularly wherein B is $NHR^2$ and $R^2$ is —CHO, methyl, ethyl, or propyl;

Q is selected from OH, $NH_2$, F and H, particularly Q is OH or H;

E is selected from H, CO—$R^3$, $CONHR^3$ and $CON(OH)R^3$, wherein $R^3$ is H or a $C_1$ to $C_6$ substituted or unsubstituted alkyl (particularly a $C_1$ to $C_3$ alkyl bearing $NH_2$ and/or OH moieties), particularly wherein E is selected from (S)-4-amino-2-hydroxybutyryl, (S)-3-amino-2-hydroxypropionyl, —CON(OH)($CH_2$)$_2NH_2$), (2R,3S)-2-hydroxy-4,5-diaminopentanoyl, and (2S,3R)-2,5-dihydroxy-4-aminopentanoyl, and $R^Z$ is H or 2-aminoethyl, and $R^\omega$ is characterized by a general formula (200) or (201)

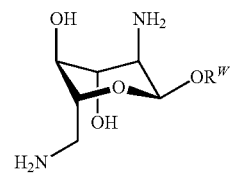
(200)

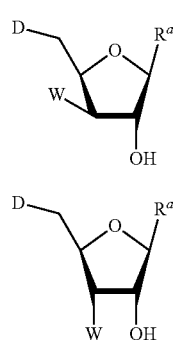
(201)

wherein $R^\alpha$ designates the bond linking the moiety to the oxygen designated $OR^\omega$ of moiety (100);

D is selected from $NH_2$, OH, H, and $NHR^4$, wherein $R^4$ is selected from CHO, $CONH_2$, CONHOH, and amino- and/or hydroxy-substituted $C_1$ to $C_6$ alkyl, particularly where D is $NHR^4$ and $R^4$ is selected from CHO, $CONH_2$, CONHOH, $COCH_2NH_2$; $COCH(NH_2)(CH_2)_4NH_2$, or $COCH(NH_2)(CH_2)_3NHC(NH)NH_2$, and amino-substituted or hydroxy-substituted methyl, ethyl, n- or iso-propyl; more particularly where D is NHCHO or $NHCONH_2$, and W is selected from OH, F, H, —O($CH_2$)$_2NH_2$, —O($CH_2$)$_2NH(CH_2$)$_3NH_2$, O—($CH_2$)$_2$—N-morpholino, O—($CH_2$)$_2$—N-piperidono, O—($CH_2$)$_2$—N—[($CH_2$)$_2OH$]$_2$ and a moiety characterized by formula (300) or (301)

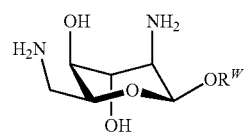
(300)

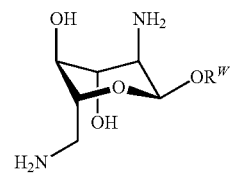
(301)

wherein $R^W$ designates the bond linking the moiety to the carbon designated W of moiety (200) or (201).

In particular embodiments, the compound is described by a general formula (101″), particularly by (102″) or (102a″)

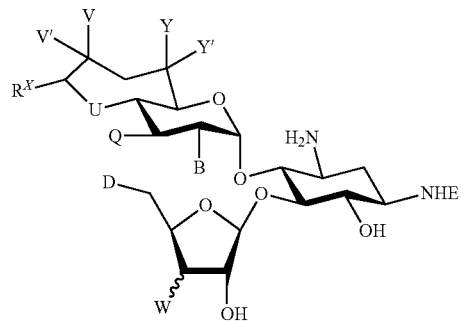
(101″)

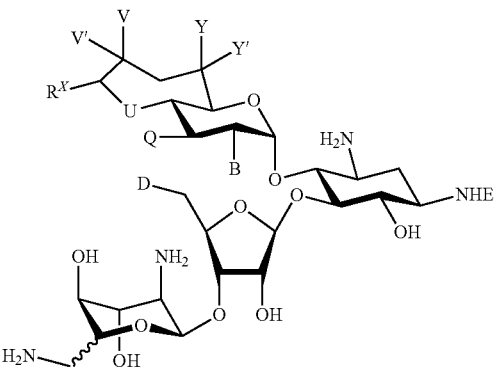
(102″)

35
-continued (102a″)

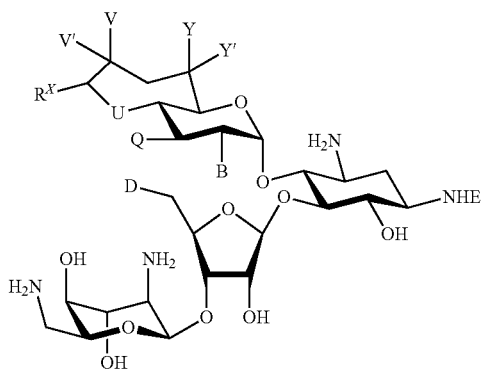

(104″)

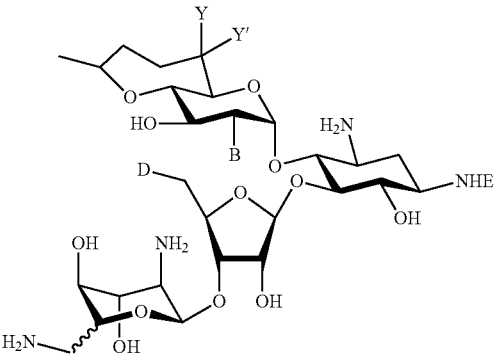

wherein one of Y and Y' is selected from OH and NH$_2$ and the other one is H, particularly wherein Y is H and Y' is selected from OH and NH$_2$, R$^X$ is selected from H, methyl, ethyl, aminomethyl, hydroxymethyl, 2-aminoethyl, 2-hydroxyethyl, CH$_2$NHR (with R being a C$_1$ to C$_4$ alkyl), CH$_2$F, CHF$_2$, and CF$_3$, V and V' independently are selected from H, OH, NH$_2$, NHR and NHR$_2$ with R being a amino-, hydroxyl- or fluoro-substituted C$_1$ to C$_4$ alkyl, particularly (CH$_2$)$_n$OH, (CH$_2$)$_n$NH$_2$ (CH$_2$)$_n$F with n being 2, 3 or 4, U is selected from O, S, CH$_2$, SO and SO$_2$, —CH(OH)— and —CH(NH$_2$)— wherein B is selected from NH$_2$, OH, H, and NHR$^2$, wherein R$^2$ is selected from —CHO, —CONH$_2$, substituted or unsubstituted C$_1$ to C$_6$ alkyl, and COR$^{2A}$, wherein R$^{2A}$ is an amino-substituted C$_1$ to C$_6$ alkyl, particularly wherein B is NHR$^2$ and R$^2$ is —CHO, —CONH$_2$, and unsubstituted C$_1$ to C$_4$ alkyl, more particularly wherein B is NHR$^2$, and R$^2$ is selected from CHO, methyl, ethyl, and propyl, and wherein D, E, Q and W, where appropriate, have the meaning indicated above.

In particular embodiments, the compound is described by a general formula (103″), particularly by (104″) or (104a″)

(103″)

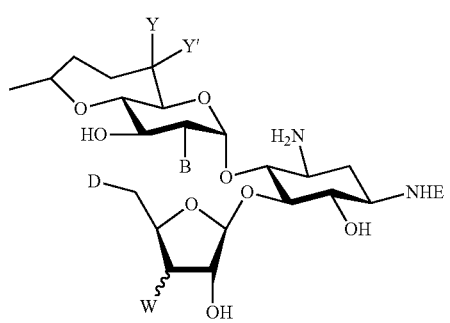

36
-continued (104a″)

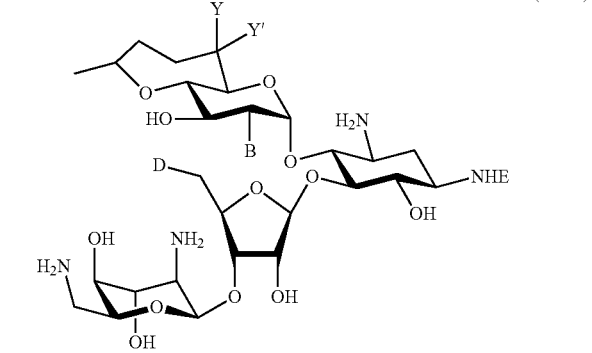

wherein one of Y and Y' is selected from OH, NH$_2$ and CH$_2$NHR$^O$, and the other one is H, particularly wherein Y is H and Y' is selected from OH, NH$_2$ and CH$_2$NHR$^O$, wherein R$^O$ has the same meaning as indicated in claim 1, particularly wherein R$^O$ is selected from methyl, ethyl, 2-aminoethyl and 2-hydroxyethyl, more particularly wherein Y is H and Y' is OH, W, where appropriate, has the same meaning as indicated in claim 1, and B is NHR$^2$, wherein R$^2$ is selected from substituted or unsubstituted C$_1$ to C$_6$ alkyl (particularly R$^2$ is an unsubstituted, amino-substituted and/or hydroxy-substituted methyl, ethyl, n- or iso-propyl), —CHO, —CONH$_2$, and D is OH or B is NHR$^2$, wherein R$^2$ is has the meaning indicated in the previous paragraph, and D is selected from NH—CHO and NH—CONH$_2$ or D is selected from NH—CHO and NH—CONH$_2$ and B is NH$_2$.

In particular embodiments, the compound is described by a general formula (103″h), particularly by (104″h) or (104a″h)

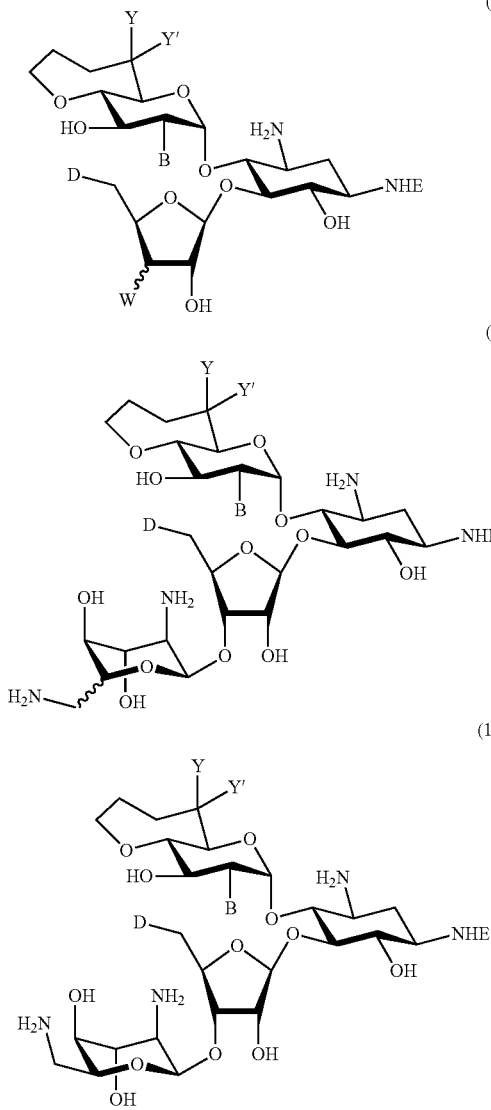

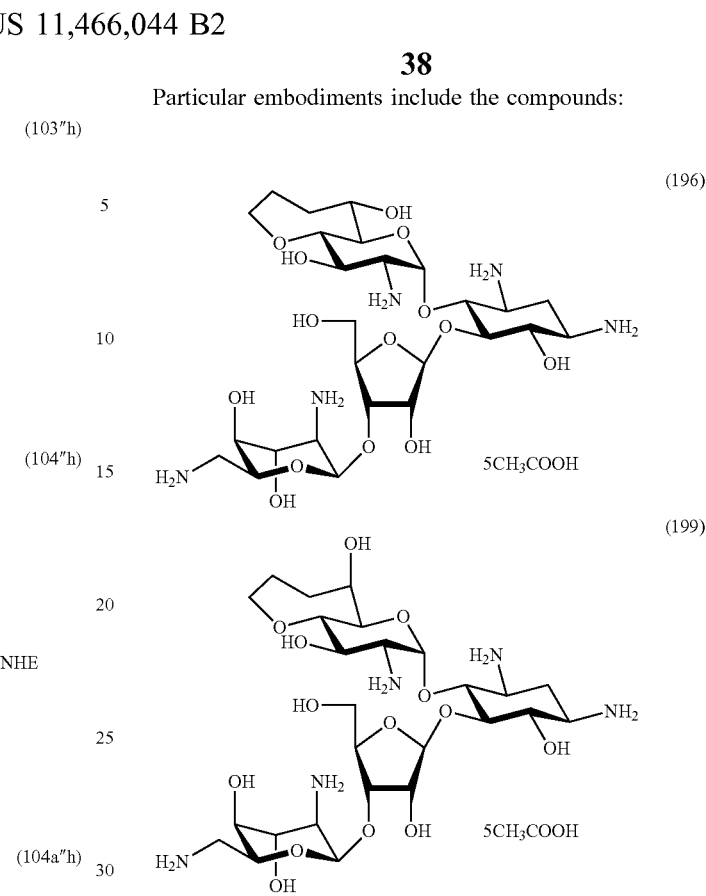

W, where appropriate, has the same meaning as indicated in the first aspect, and
B is NH$_2$, D is OH, E is H and
a. Y is H and Y' is OH (196) or
b. Y is OH and Y' is H (199), In particular embodiments, Y is H and Y' is selected from OH, NH$_2$ and CH$_2$NHR°, wherein R° has the same meaning as indicated in the first aspect, particularly wherein R° is selected from methyl, ethyl, 2-aminoethyl and 2-hydroxyethyl, and B, D, E, G, L, Q and W, where appropriate, have the same meaning as indicated in claim 1.
In particular embodiments, Y' is OH.
In particular embodiments, B is NH$_2$.
In particular embodiments, D is OH.
In particular embodiments, E is H.
In particular embodiments, E is selected from (S)-4-amino-2-hydroxybutyryl, (S)-3-amino-2-hydroxypropionyl, —CON(OH)(CH$_2$)$_2$NH$_2$), (2R,3S)-2-hydroxy-4,5-diamino-pentanoyl, and (2S,3R)-2,5-dihydroxy-4-aminopentanoyl.
In particular embodiments, Q is OH or H, particularly wherein Q is OH.

Particular embodiments include the compounds:

Particular embodiments relate to the use of a compound according to any of the previously described aspects, sub aspects and embodiments, or combinations of particular features, in the therapy of bacterial infection by systemic administration. The skilled artisan is aware that on the basis of the data provided and the general description, certain compounds can be identified that show advantageous selectivity for the bacterial, rather than the eukaryotic mitochondrial, ribosome.

Particular embodiments having a favorable selectivity comprise a hydroxyl moiety linked to the 6' carbon (position A), particularly wherein the 6' C is in (S) configuration.

In particular embodiments of this aspect, the compound for use in the therapy of bacterial infection is administered by systemic administration in a patient carrying a mutation in the A-site of the mitochondrial ribosomal RNA selected from A1555G and C1494U. Patients carrying these mutations are at particular jeopardy of suffering hearing loss and other permanent side-effects of AGA administration.

Particular embodiments relate to the use of a compound according to any of the previous aspects or embodiments in the therapy of bacterial infection, particularly by systemic administration. Certain particular embodiments relate to its use in infections caused by the so-called ESKAPE group of bacterial pathogens (*Enterococcus faecium, Staphylococcus aureus, Klebsiella pneumoniae, Acinetobacter baumannii, Pseudomonas aeruginosa* and *Enterobacter* species)(see Boucher et al. Clinical Infectious Diseases. 48 (1): 1-12; Renner et al. Appl Environ Microbiol. 2017 Feb. 15; 83(4): e02449-16) the infection is caused by a pathogen selected from the genera *Klebsellia* (particularly *K. pneumoniae*), *Escherichia* (particularly *E. coli*), *Mycobacterium, Pseudomonas* (particularly *P. aeroginosa*), *Acinetobacter* (particularly *A. baumannii*), *Enterobacter* (particularly *E. cloacae*), and *Neisseria* (particularly *N. gonorrhoeae*).

Another aspect relates to the use of a compound according to any of the aspects or embodiments disclosed herein, in the therapy of bacterial infection, wherein the infection is caused by a pathogen comprising a resistance determinant selected from AAC(6') aminoglycoside N-acetyltransferase, AAC(2') aminoglycoside N-acetyltransferase, APH(3') aminoglycoside O-phosphotransferase and ANT(4') aminoglycoside O-nucleotidyltransferase.

Particular embodiments relate to a compound according to the first aspect, in particular the first subaspect, for use in the therapy of bacterial infection, wherein the infection is caused by a pathogen selected from the genus *Mycobacterium*, particularly by systemic administration.

Particular embodiments relate to a compound according to the first aspect, in particular the first subaspect, for use in the therapy of bacterial infection, wherein the infection is caused by a pathogen comprising an AAC(2') aminoglycoside N-acetyltransferase resistance determinant.

Particular embodiments relate to a compound according to the first aspect, in particular the first subaspect, wherein B is selected from H, OH, NR$^2$, and NHR$^2$ and R$^2$ is —CHO, —CONH$_2$, an unsubstituted or amino-substituted methyl, ethyl, n- or iso-propyl, particularly wherein B is NHR$^2$ and R$^2$ is —CHO, methyl, ethyl, or propyl; for use in the therapy of infection by a bacterium, wherein the bacterium comprises an AAC(2') aminoglycoside N-acetyltransferase resistance determinant and/or the infection is caused by a pathogen selected from the genus *Mycobacterium*.

Particular embodiments relate to a compound according to the first aspect, in particular the first subaspect, for use in the therapy of infection by a bacterium, wherein the bacterium comprises a resistance determinant selected from
AAC(6') aminoglycoside N-acetyltransferase and/or
ANT(4') aminoglycoside O-nucleotidyltransferase and/or
APH(3') aminoglycoside O-phosphotransferase
wherein the compound is defined by a general formula (101), (102) or (102a), wherein Y' is selected from OH, NH$_2$ and NHR$^O$, wherein R$^O$ is selected from the group consisting of methyl, ethyl, 2-aminoethyl, 2-hydroxyethyl, CH$_2$CH$_2$NHR, CH$_2$CH$_2$F, CH$_2$CHF$_2$, (CH$_2$)$_n$CF$_3$, and particularly wherein Y' is OH, more particularly wherein V is H, U is O and Y' is H, even more particularly for use by systemic administration.

In particular embodiments, the resistance determinant is selected from the following table:

| Name | Enzyme family | Target | Exemplary GenBank accession numbers |
|---|---|---|---|
| AAC(6')-I | Aminoglycoside N-acetyltransferase | 6'-NH$_2$ | AF479774, M21682, M23634, and many others |
| AAC(6')-II | Aminoglycoside N-acetyltransferase | 6'-NH$_2$ | M29695, L06163, NC_012555, and many others |
| AAC(2')-I | Aminoglycoside N-acetyltransferase | 2'-NH$_2$ | L06156, CP001172, CP001658, NC_008596, AM743169, and many others |
| APH(3')-I | Aminoglycoside O-phosphotransferase | 3'-OH 5''-OH | V00359, M20305, M37910, and many others |
| APH(3')-II | Aminoglycoside O-phosphotransferase | 3'-OH | NC_002516, V00618, and many others |
| APH(3')-III | Aminoglycoside O-phosphotransferase | 3''-OH 5''-OH | V01547, and others |
| APH(3')-VI | Aminoglycoside O-phosphotransferase | 3'-OH 5''-OH | X07753, and others |
| ANT(4')-I | Aminoglycoside O-nucleotidyltransferase | 4'-OH 4''-OH | U35229, M19465, and others |
| ANT(4')-II | Aminoglycoside O-nucleotidyltransferase | 4'-OH | M98270, AY114142, and others |
| armA | 16S-rRNA methyltransferase | N7-G1405 | AB825954, DQ177329, EU014811, FJ788923, and others |
| rmtB | 16S-rRNA methyltransferase | N7-G1405 | NC_010558, and others |
| rmtC | 16S-rRNA methyltransferase | N7-G1405 | AB824738, EU144360, FJ807682, and others |
| rmtF | 16S-rRNA methyltransferase | N7-G1405 | AB824739, JQ955744, and others |

Summary of Antimicrobial Resistance Mechanisms Addressed

Particular embodiments relate to a compound for use in the therapy of bacterial infection by systemic administration, wherein the compound is characterized by a general formula (100)

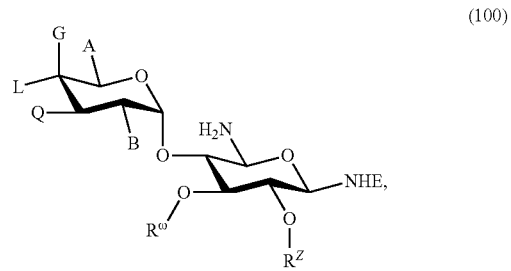

(100)

wherein
A is CH$_2$OH or CR$^1$$_2$OH, or (R)—CH(OH)R$^1$ or (S)—CH(OH)R$^1$, wherein
each R$^1$ is selected independently from the group consisting of methyl, ethyl, aminomethyl, hydroxymethyl, 2-aminoethyl, 2-hydroxyethyl, CH$_2$NHR, (CH$_2$)$_n$CH$_2$F, (CH$_2$)$_n$CHF$_2$, (CH$_2$)$_n$CF$_3$, wherein n is 1 or 2, a C$_2$ to C$_4$ alkenyl and a C$_2$ to C$_4$ alkynyl, with each R independently being selected from the group of unsubstituted C$_1$ to C$_4$ alkyl,
wherein
G is H and L is O—R$^{4'}$, SR$^{4'}$ or R$^{4'}$, with R$^{4'}$ being selected from H and unsubstituted, fluoro-, amino- and/or hydroxysubstituted C$_1$ to C4 alkyl, or
G is F and L is H or C$_1$ to C$_4$ alkyl; or
A and L are connected via a moiety —CR$^5$$_2$— and L is —O— or —CR$^5$$_2$—,
wherein each R$^5$ is independently being from H, F and R$^1$, and
A is (S)—CH(OH), or (S)—C(OH)R$^1$
wherein each R$^1$ is selected independently from the group consisting of methyl, ethyl, aminomethyl, hydroxymethyl, 2-aminoethyl, 2-hydroxyethyl, CH$_2$NHR, (CH$_2$)$_n$CH$_2$F, (CH$_2$)$_n$CHF$_2$, (CH$_2$)$_n$CF$_3$, wherein n is 1 or 2, and wherein each R is independently selected from the group of unsubstituted C$_1$ to C$_4$ alkyl, and G is H,
and wherein
B is selected from NH$_2$, OH, H, and NHR$^2$, wherein R$^2$ is selected from —CHO, —CONH$_2$, substituted or unsubstituted C$_1$ to C alkyl, and COR$^{2A}$, wherein R$^{2A}$ is an amino-substituted C$_1$ to C$_6$ alkyl, particularly wherein B is NHR$^2$ and R$^2$ is —CHO, —CONH$_2$, an unsubstituted or aminosubstituted methyl, ethyl, n- or iso-propyl, COCH$_2$NH$_2$; COCH(NH$_2$)(CH$_2$)$_4$NH$_2$, or COCH(NH$_2$)(CH$_2$)$_3$NHC(NH)NH$_2$, more particularly wherein B is NHR$^2$ and R$^2$ is —CHO, methyl, ethyl, or propyl;

Q is selected from OH, NH$_2$, F and H, particularly Q is OH or H;

E is selected from H, CO—R$^3$, CONHR$^3$ and CON(OH)R$^3$, wherein R$^3$ is H or a C$_1$ to C$_6$ substituted or unsubstituted alkyl (particularly a C$_1$ to C$_3$ alkyl bearing NH$_2$ and/or OH moieties), particularly wherein E is selected from (S)-4-amino-2-hydroxybutyryl, (S)-3-amino-2-hydroxypropionyl, —CON(OH)(CH$_2$)$_2$NH$_2$), (2R,3S)-2-hydroxy-4,5-diaminopentanoyl, and (2S,3R)-2,5-dihydroxy-4-aminopentanoyl, R$^Z$ is H or 2-aminoethyl, and R$^ω$ is characterized by a general formula (200) or (201)

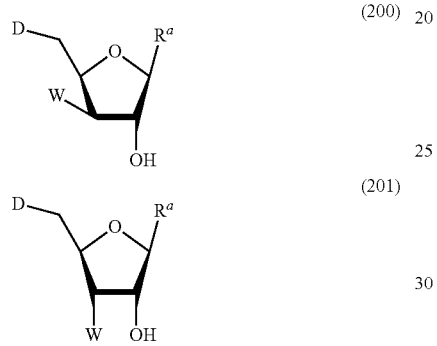

wherein R$^ω$ designates the bond linking the moiety to moiety (100);

D is selected from NH$_2$, OH, H, and NHR$^4$, wherein R$^4$ is selected from CHO, CONH$_2$, CONHOH, and amino- and/or hydroxy-substituted C$_1$ to C$_6$ alkyl, particularly where D is NHR$^4$ and R$^4$ is selected from CHO, CONH$_2$, CONHOH, COCH$_2$NH$_2$; COCH(NH$_2$)(CH$_2$)$_4$NH$_2$, or COCH(NH$_2$)(CH$_2$)$_3$NHC(NH)NH$_2$, and amino-substituted or hydroxy-substituted methyl, ethyl, n- or iso-propyl; more particularly where D is NHCHO or NHCONH$_2$, and W is selected from OH, F, H, —O(CH$_2$)$_2$NH$_2$, —O(CH$_2$)$_2$NH(CH$_2$)$_3$NH$_2$, O—(CH$_2$)$_2$—N-morpholino, O—(CH$_2$)$_2$—N-piperidono, O—(CH$_2$)$_2$—N—[(CH$_2$)$_2$OH]$_2$ and a moiety characterized by formula (300) or (301)

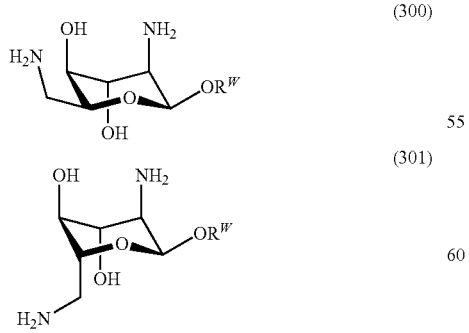

wherein R$^W$ designates the bond linking the moiety to moiety (200) or (201), with the proviso that the molecule is not described by the following combination of parameters:

A is CH$_2$OH or CH$_2$NH$_2$, B is NH$_2$, R is H and R is (201), and D is OH, or A is CH$_2$OH or CH$_2$NH$_2$, and B is OH, and R$^W$ is H and R$^Z$ is any one of (400), (401), and (402)

A is CH$_2$NH$_2$, and B is NH$_2$, OH or H, and R$^W$ is H and R$^Z$ is H;

A is CH$_2$NH$_2$, B is OH, R$^Z$ is H, R$^W$ is (200) and D is OH.

Particular embodiments relate to a compound for use in the therapy of bacterial infection by systemic administration, wherein B is NHR$^2$ and R$^2$ is —CHO, methyl, ethyl, or propyl.

Particular embodiments relate to a compound for use in the therapy of bacterial infection by systemic administration according to claim 40 or 41, wherein A is CR$^{12}$OH or (S)—CH(OH)R$^1$, and each R$^1$ is selected independently from the group consisting of methyl and ethyl.

Particular embodiments relate to a compound for use in the therapy of bacterial infection by systemic administration, wherein Q is H, and
  a. A is selected from CH$_2$OH, CR$^{12}$OH, and (S)—CH(OH)R$^1$, wherein R$^1$ is selected from the group consisting of methyl, ethyl, —CH$_2$NH$_2$, —CH$_2$OH, 2-aminoethyl, and 2-hydroxyethyl, and G is H and L is O—R$^{A'}$, SR$^{A'}$ or R$^{A'}$, with R$^{A'}$ being selected from H and unsubstituted, fluoro-, amino- and/or hydroxy-substituted C$_1$ to C$_4$ alkyl, or G is F and L is H or C$_1$ to C$_4$ alkyl; or
  b. A and L are connected via a moiety —CR$^5_2$— and L is —O— or —CR$^5_2$—, wherein each R$^5$ is independently being from H, F and R$^1$, and A is (S)—CH(OH), or (S)—C(OH)R wherein R$^1$ is selected from the group consisting of methyl, ethyl, —CH$_2$NH$_2$, —CH$_2$OH, 2-aminoethyl, and 2-hydroxyethyl, and G is H.

Particular embodiments relate to a compound for use in the therapy of bacterial infection by systemic administration, wherein D is NCHO.

Particular embodiments relate to a compound for use in the therapy of bacterial infection by systemic administration, wherein the compound is provided for administration to a patient carrying a mutation in the A-site of the mitochondrial ribosomal RNA selected from A1555G and C1494U.

Particular embodiments relate to a compound for use in the therapy of bacterial infection by systemic administration, wherein the infection is caused by a pathogen selected from the genera *kiebsellia* (particularly *K. pneumoniae*), *Escherichia* (particularly *E. coli*, *Mycobacterium*, *Pseudomonas* (particularly *P. aeroginosa*), *Acinetobacter* (particularly *A. baumannii*), *Enterobacter* (particularly *E. cloacae*), and *Neisseria* (particularly *N. gonorrhoeae*).

Modifications in Position A.

Particular embodiments further relate to a compound selected from:

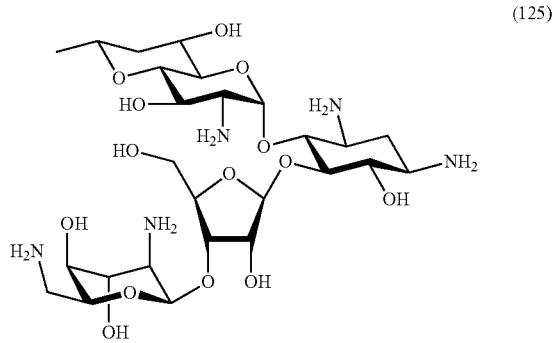

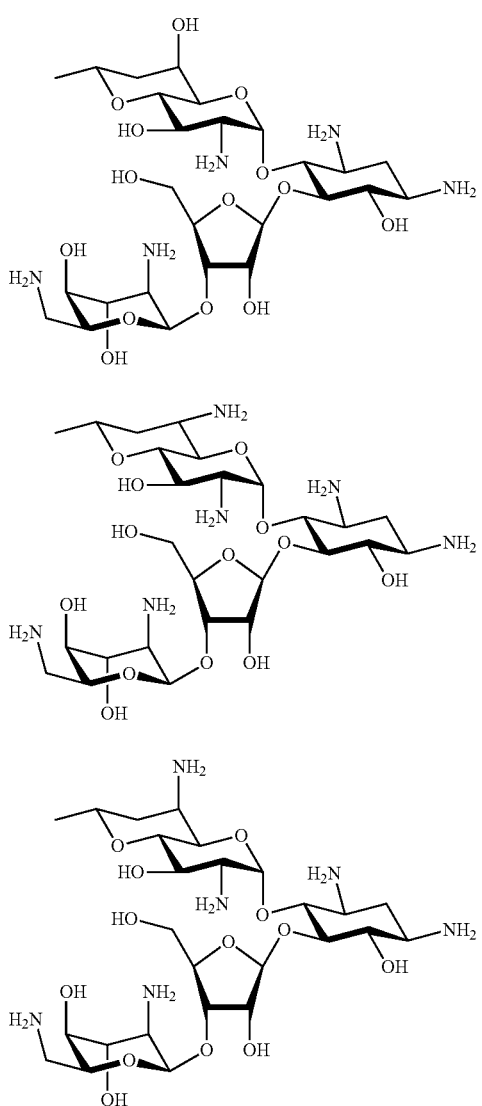
(109)
(139)
(150)
Particular embodiments further relate to the compounds:
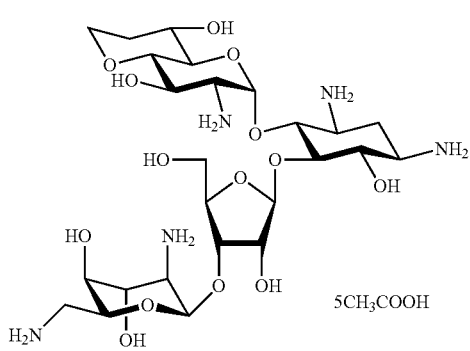
(210)
5CH₃COOH
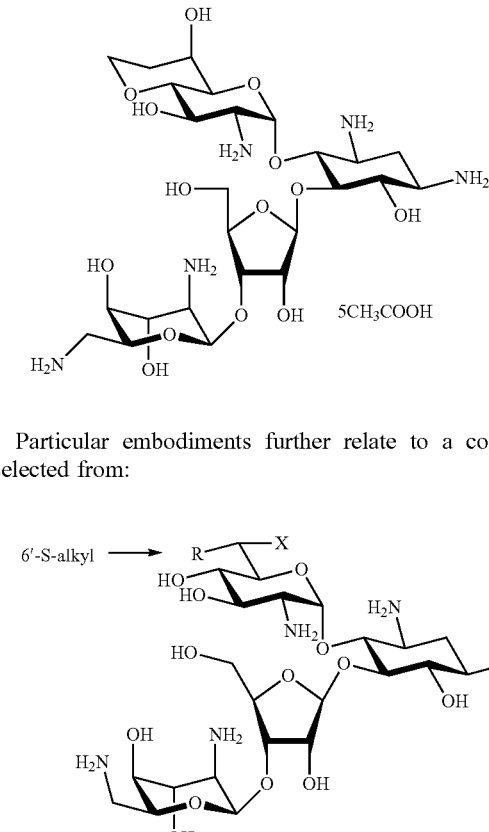
(211)
5CH₃COOH
Particular embodiments further relate to a compound selected from:
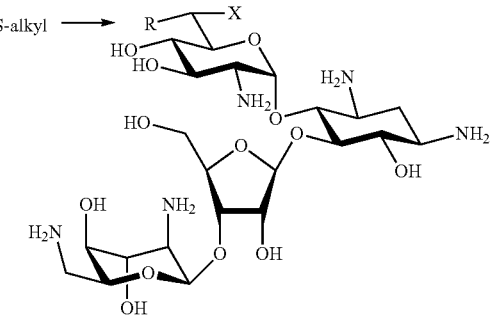
6'-S-alkyl
155: R = Me, X = OH
189: R = Et, X = OH
143: R = propyl, X = OH
244: R = NH₂, X = OH
245: R = CH₂, X = OH
166: R = Me, X = NH₂
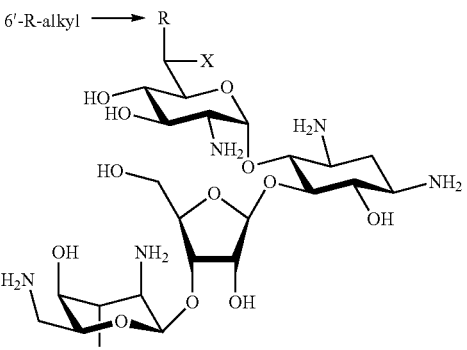
6'-R-alkyl
156; R = Me, X = OH
257: R = Ethyl, X = OH
142: R = propyl, X = OH
241: R = NH₂, X = OH
242: R = CH₂, X = OH
266: R = Me, X = NH₂

-continued

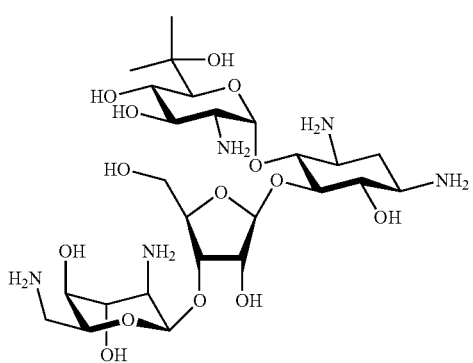

159

Me: methyl/—CH₃; Et: ethyl CH₂CH₃)

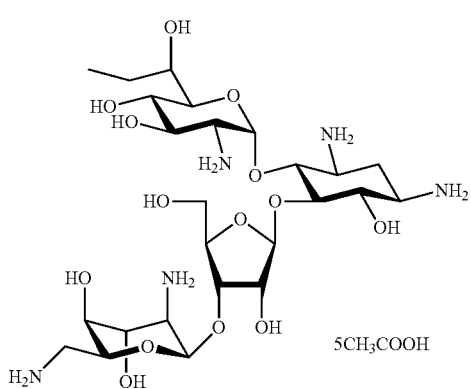

(192)

5CH₃COOH

Modifications in Position B.

Particular embodiments further relate to a compound selected from:

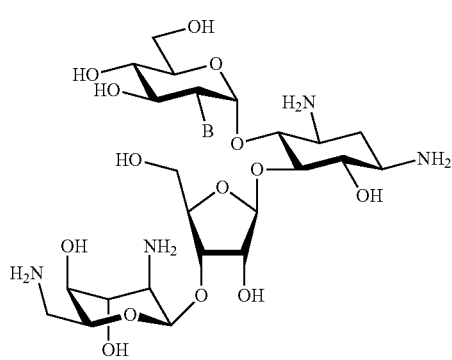

118: B = OH
115: B = NHMe
127: B = NHEt
128: B = NHPr

-continued

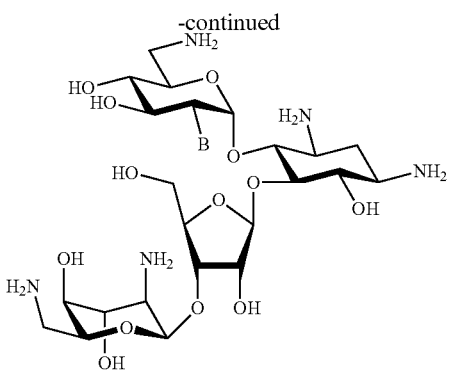

173: B = H
119: B = OH
171: B = NHMe
172: B NHEt
182: B = NHCHO
183: B = NHAc
175: B = NHCOCH₂NH₂

(Me: methyl/—CH₃; Et: ethyl CH₂CH₃, Ac: COCH₃)

Compound 183 is not encompassed by the embodiments, but serves as a comparative example.

Modification, particularly alkylation of (ring I) N2' in both paromomycin and neomycin B prevents the action of AAC(2') AMEs with little to no loss of antibacterial activity (Example 3, see Tables 1 and 2).

Alkylation of N2' in paromomycin (115, 127, 128) further results in increased selectivity for the bacterial ribosome over the A1555G mutant mitochondrial and cytosolic ribosomes, predictive of reduced ototoxicity and systemic toxicity. Similarly, alkylation of N2' in neomycin B (171, 172) results in increased selectivity for the bacterial ribosome over the mitochondrial (wild type and A1555G mutant) and cytosolic ribosomes, again predictive of reduced ototoxicity and systemic toxicity.

Deamination of N2' (173) and replacement of N2' by an hydroxyl group (119) in neomycin B overcomes the effect of AAC(2') with little to no loss of antibacterial activity (Tables 1 and 2).

Deamination of N2' (173) and replacement of N2' by an hydroxyl group (119) in neomycin B results in increased selectivity for the bacterial ribosome over the mitochondrial (wild type and A1555G mutant) and cytosolic ribosomes, predictive of reduced ototoxicity and systemic toxicity.

Conversion of the neomycin B 2'-amino group to a formamido group results in a compound (182) that retains most of the activity of the parent and which is not susceptible to deactivation by AAC(2'). This is distinct from the acetamide (183) and the glycinamide (175) both of which show very substantial loss of activity.

Conversion of the neomycin B 2'-amino group to a formamido group results in a compound (182) that displays increased selectivity for the bacterial ribosome over the mitochondrial (wild type and A1555G mutant) ribosomes, predictive of reduced ototoxicity.

The 2'-N-alkyl modification of neomycin and of paromomycin and other neosamine based AGA are suitable modifications to the parents enabling the reduction of toxicity and surmounting the effect of the AAC(2') resistance determinant. These modifications are suitable for use either alone or in combination with other tolerated aminoglycoside modifications designed to surmount other resistance mechanisms and/or reduce toxicity.

The 2'-deamination, 2'-amino to hydroxy conversion, and 2'-N-formylation of neomycin are suitable modifications to the parent that enable the reduction of toxicity and surmounting the effect of the AAC(2') resistance determinant. These modifications are suitable for use either alone or in combination with other tolerated aminoglycoside modifications designed to surmount other resistance mechanisms and/or reduce toxicity.

Modifications in Position D.

Particular embodiments further relate to a compound selected from:

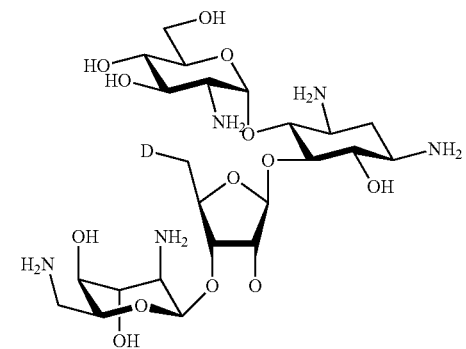

137: D = -NCHO
141: R = NHCONH₂

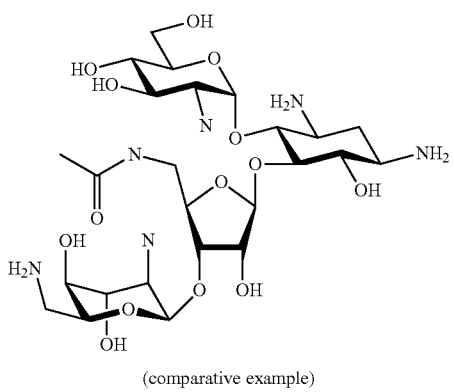

165

(comparative example)

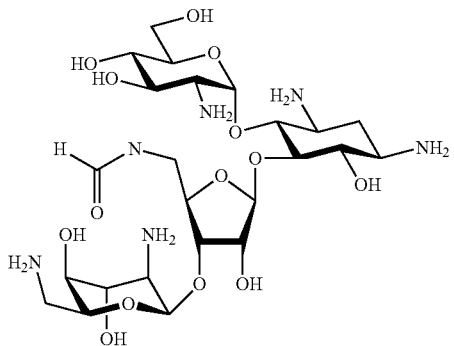

135

Particular embodiments also relates to any novel end products shown in the Figures, as well as to useful novel intermediates shown in the synthetic schemes disclosed herein.

Similarly, a dosage form for the prevention or treatment of bacterial infection is provided, comprising an amino glucoside antibacterial drug according to one of the above aspects of the embodiments. Dosage forms may be for enteral administration, such as nasal, buccal, rectal, transdermal or oral administration, or as an inhalation form or suppository. Alternatively, parenteral administration may be used, such as subcutaneous, intravenous, intrahepatic or intramuscular injection forms. Optionally, a pharmaceutically acceptable carrier and/or excipient may be present.

Topical administration is also within the scope of the advantageous uses of the compounds. The skilled artisan is aware of a broad range of possible recipes for providing topical formulations, as exemplified by the content of Benson and Watkinson (Eds.), Topical and Transdermal Drug Delivery: Principles and Practice (1st Edition, Wiley 2011, ISBN-13: 978-0470450291); and Guy and Handcraft: Transdermal Drug Delivery Systems: Revised and Expanded ($2^{nd}$ Ed., CRC Press 2002, ISBN-13: 978-0824708610); Osborne and Amann (Eds.): Topical Drug Delivery Formulations ($1^{st}$ Ed. CRC Press 1989; ISBN-13: 978-0824781835).

Wherever alternatives for single separable features such as, for example, substituents A, B and D are laid out herein as "embodiments", it is to be understood that such alternatives may be combined freely to form discrete embodiments of the invention disclosed herein.

The present disclosure is further illustrated by the following examples and figures, from which further embodiments and advantages can be drawn. These examples are meant to illustrate the invention but not to limit the scope.

Figure 2:
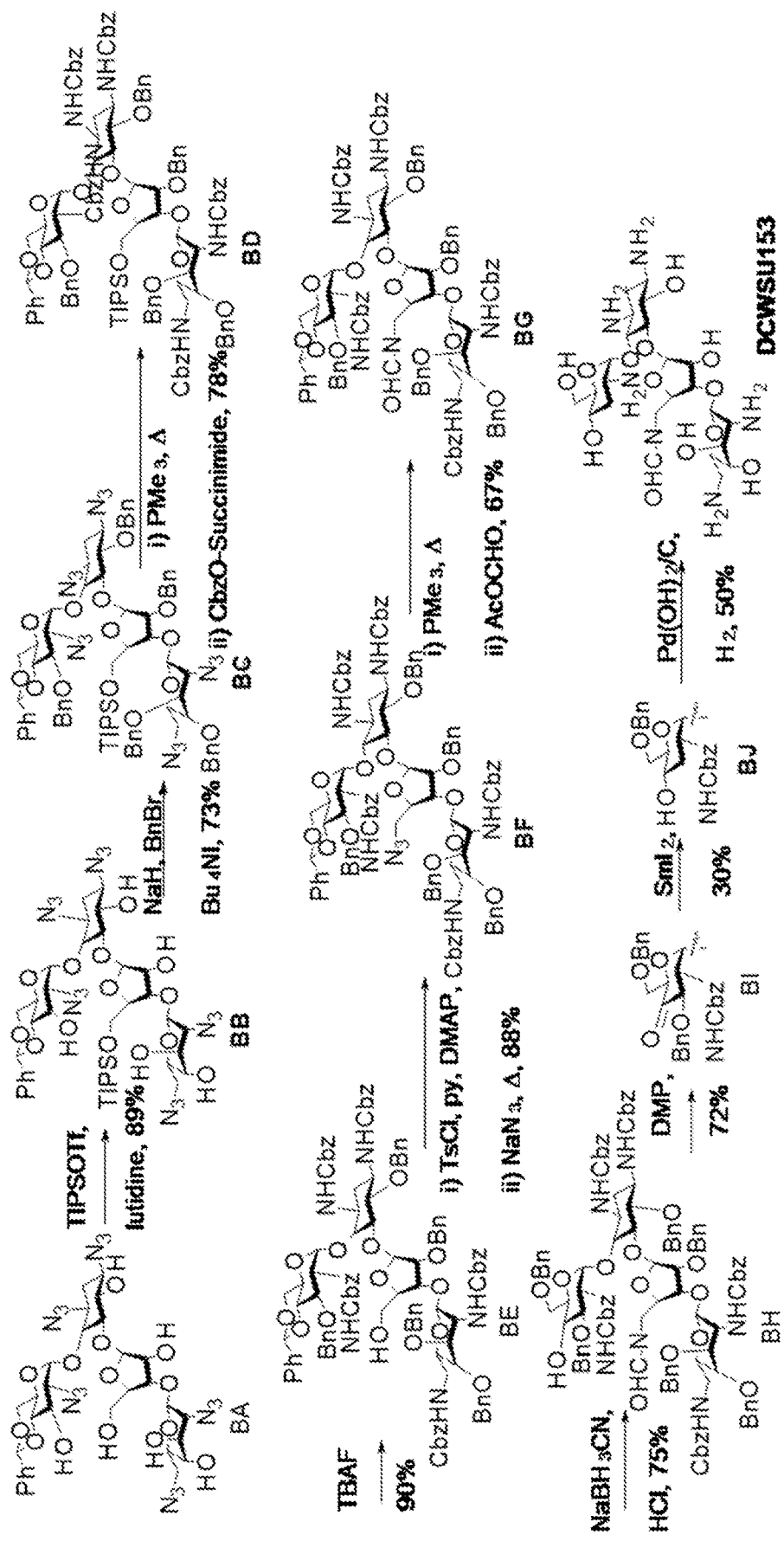

FIGS. 1 and 2 show the synthesis of exemplary compounds disclosed herein, modified in position D.

Figure 3:
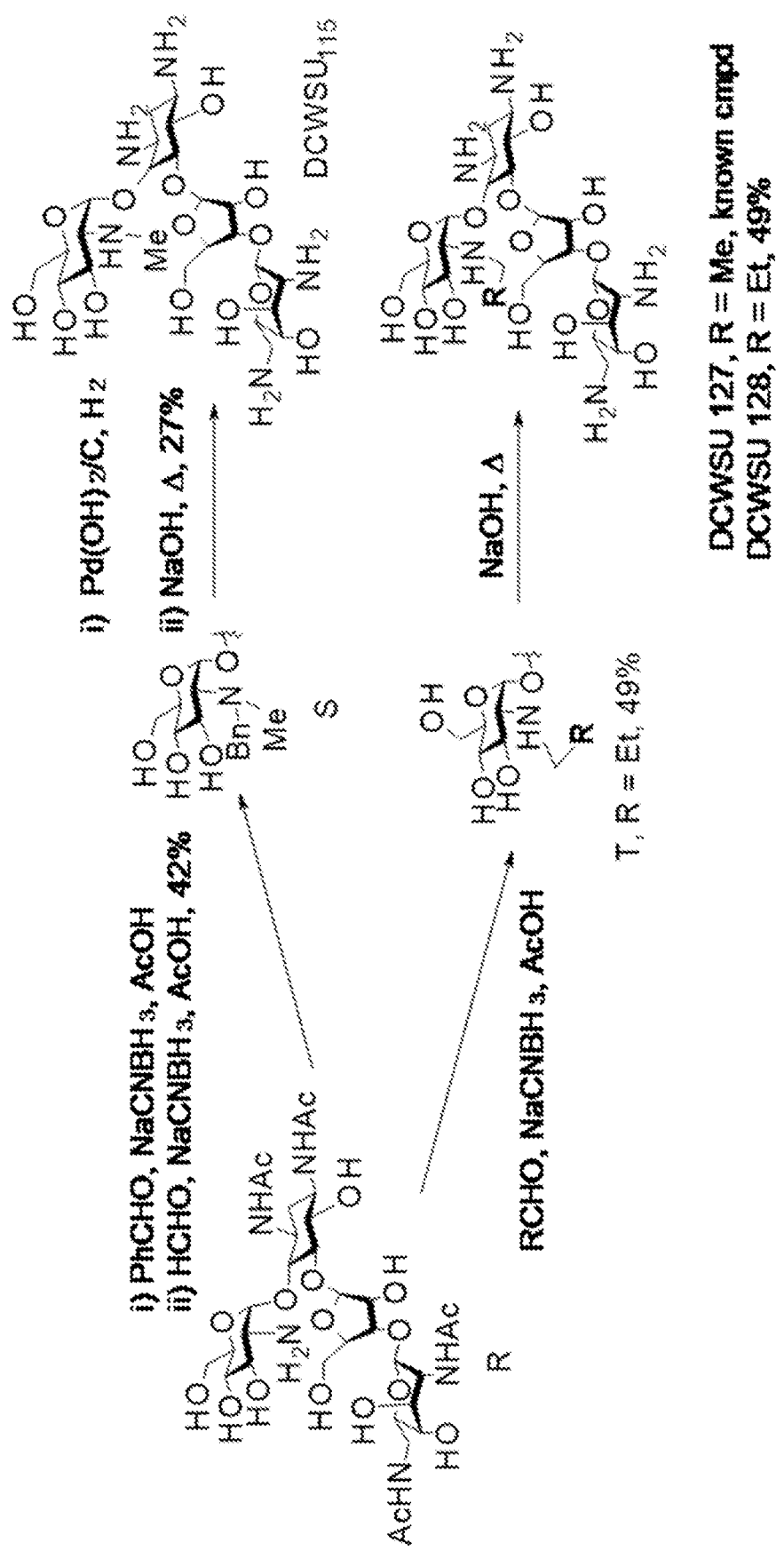
Figure 4:
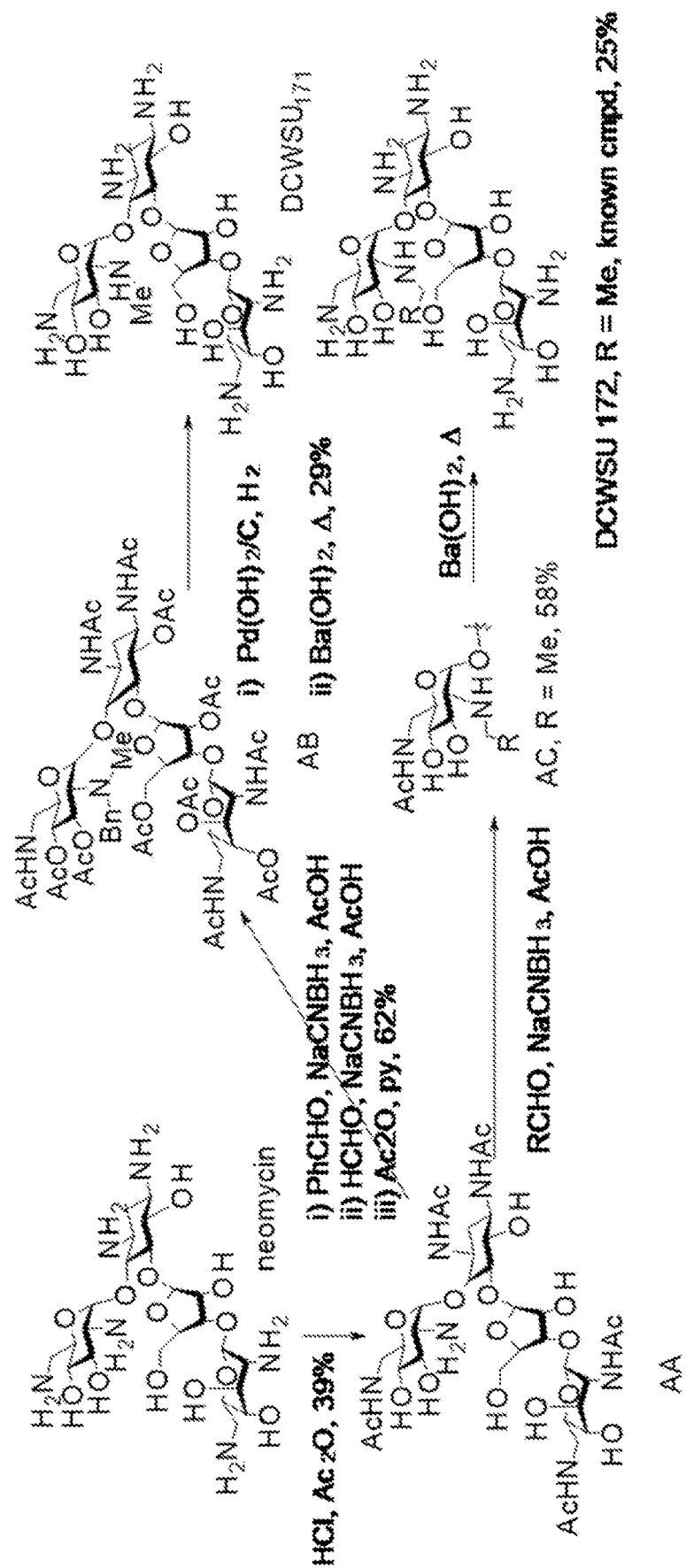
Figure 5:
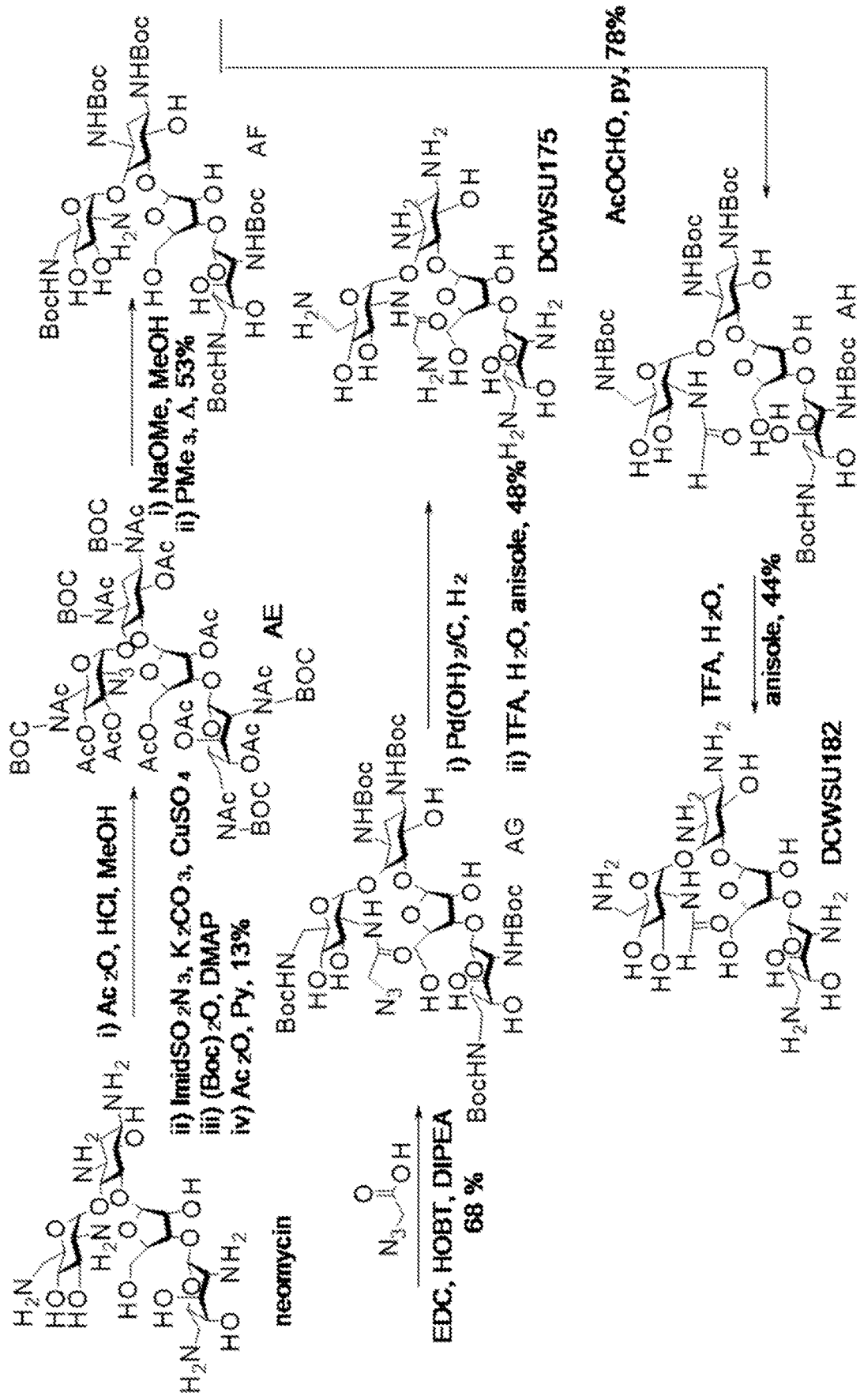

FIGS. 3, 4 and 5 show the synthesis of exemplary compounds disclosed herein, modified in position B.

Figure 6:
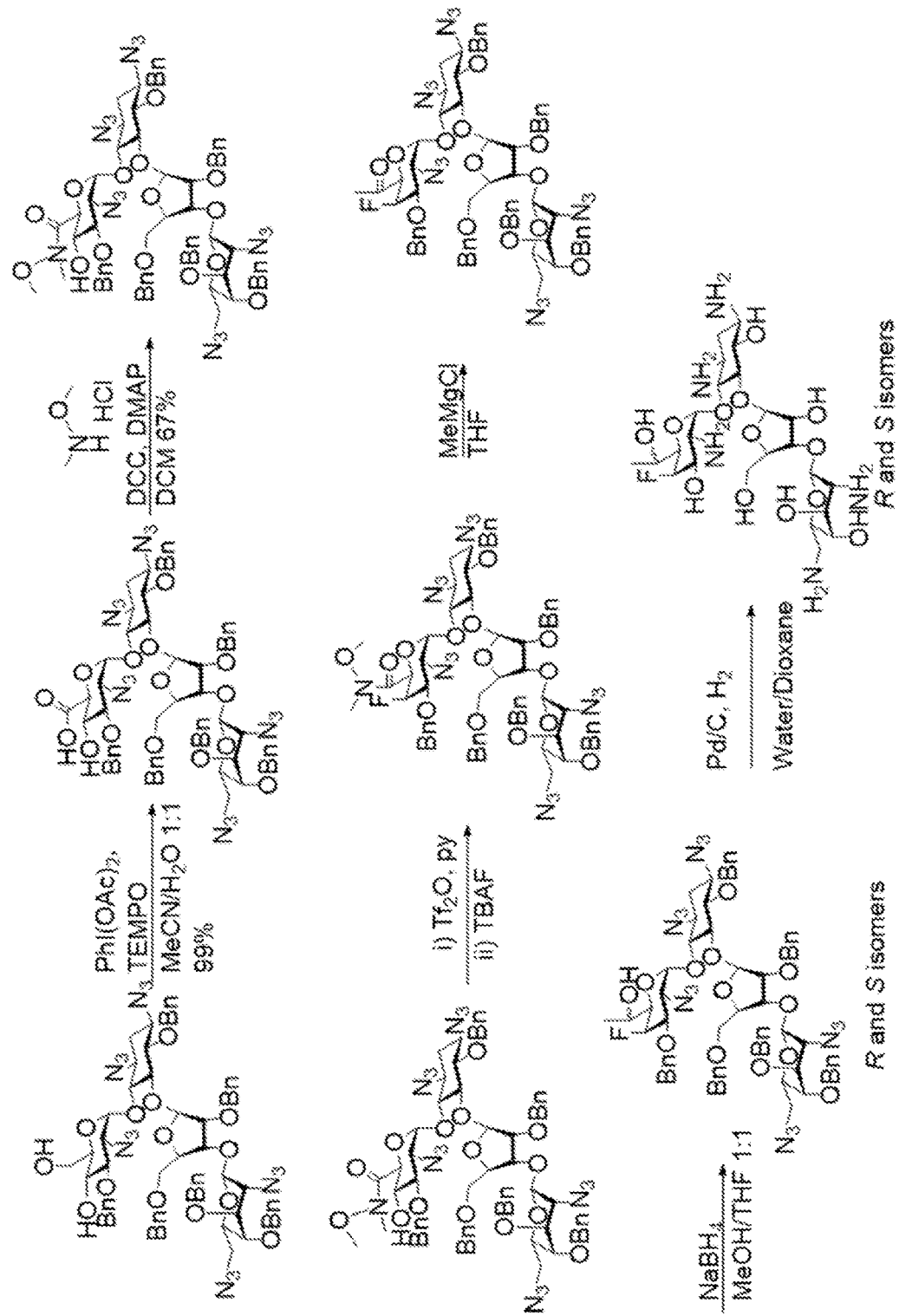
Figure 7:
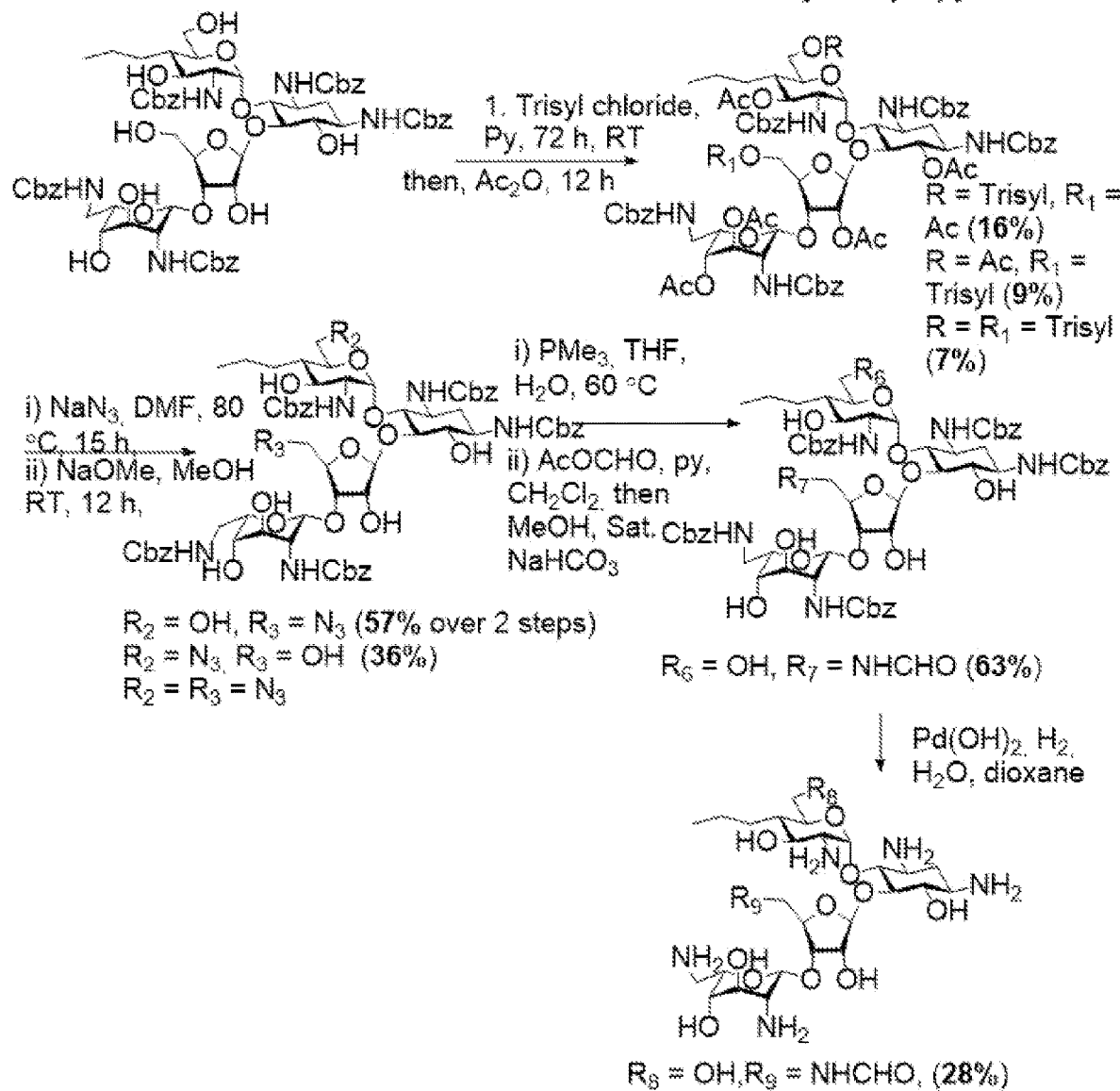
Figure 8:
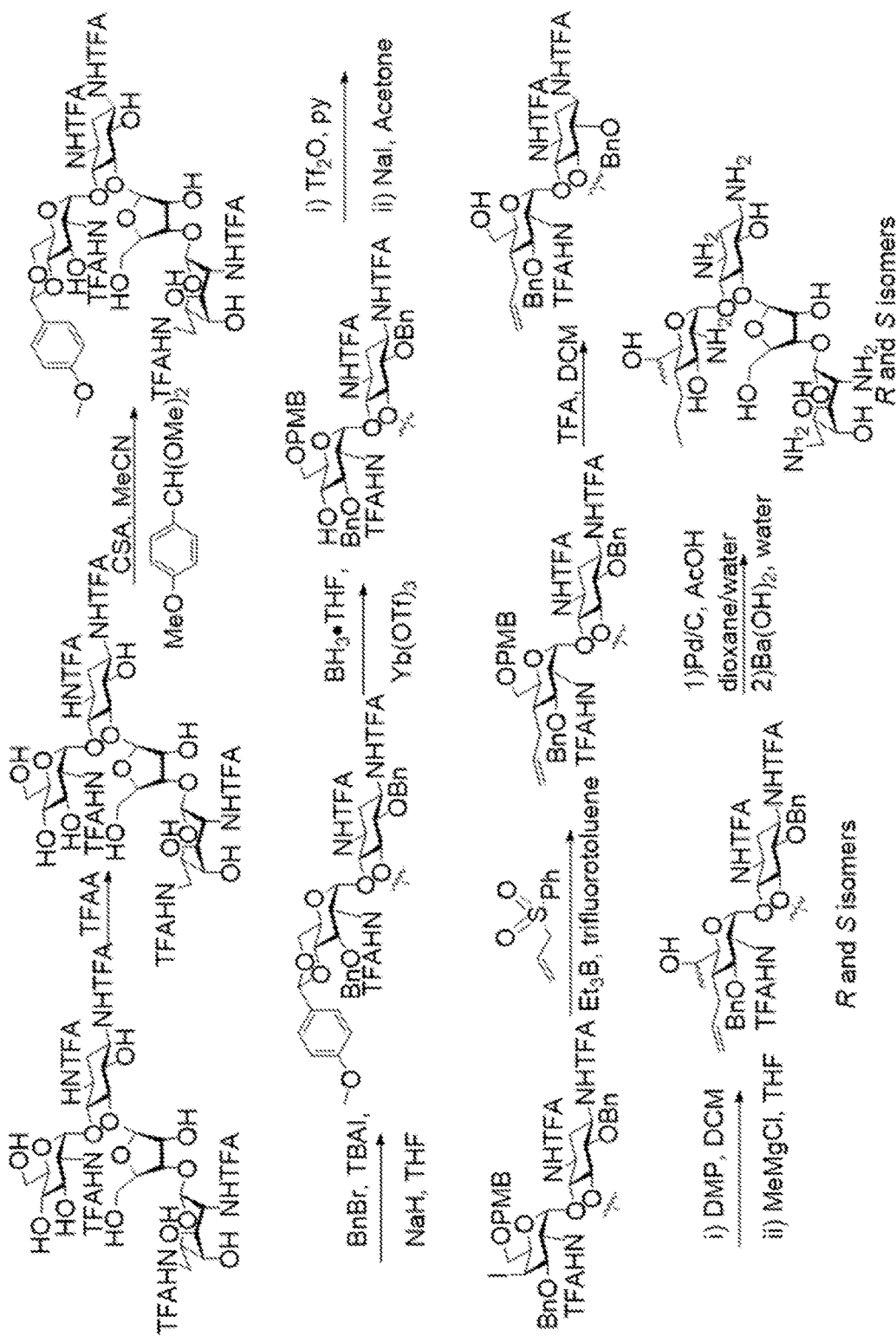
Figure 9:
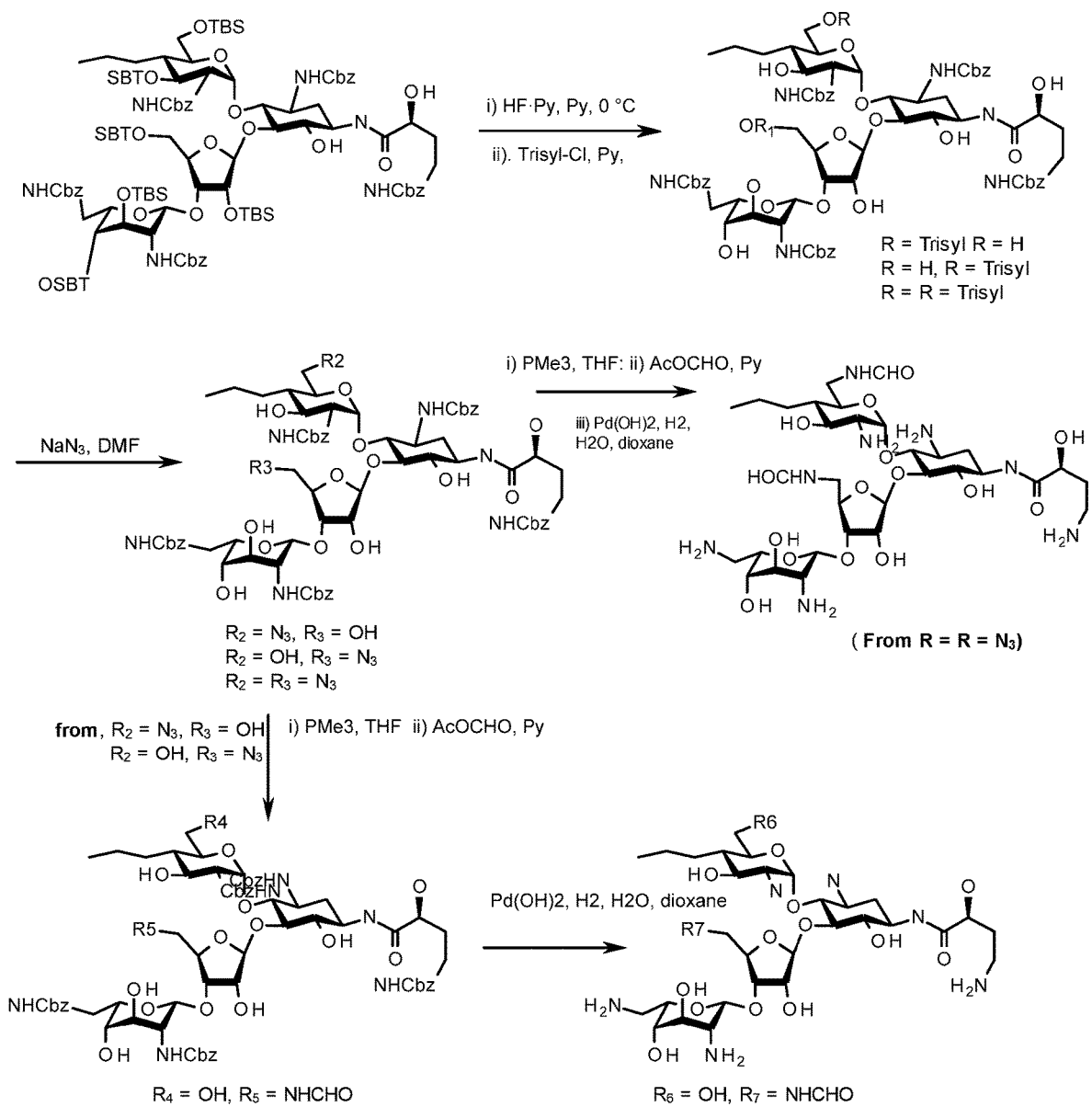
Figure 10:
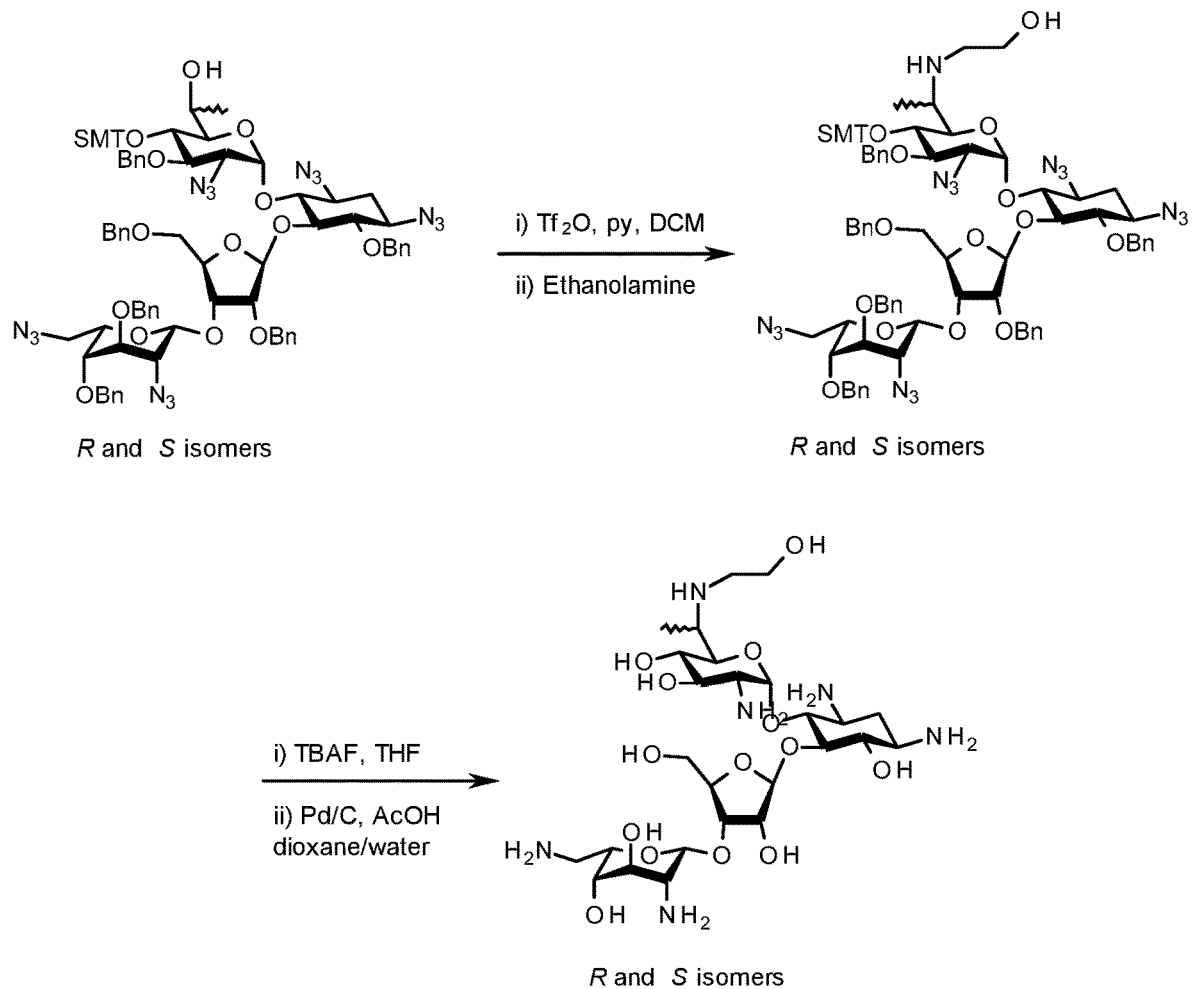
Figure 11:
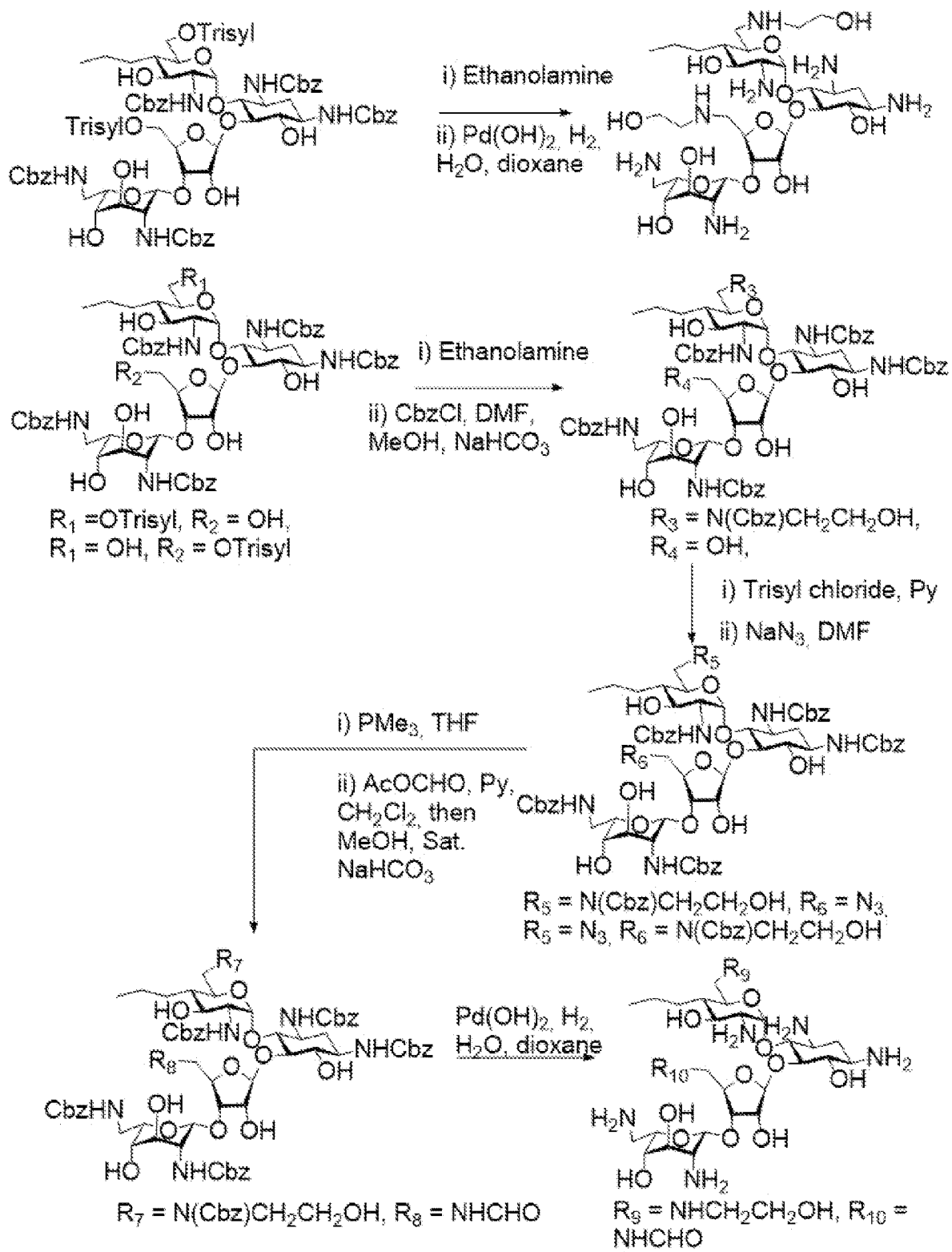
Figure 12:
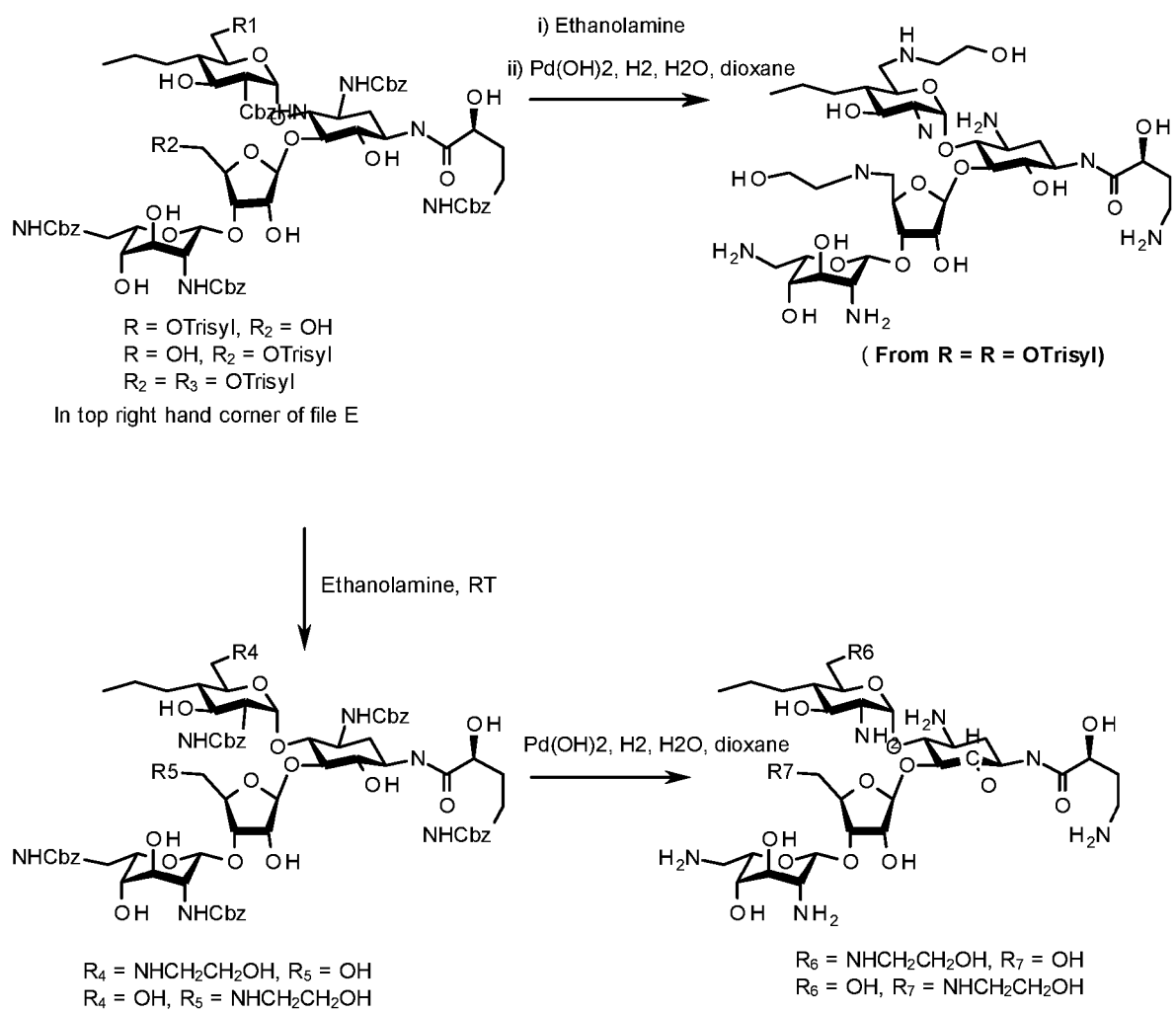
Figure 13:
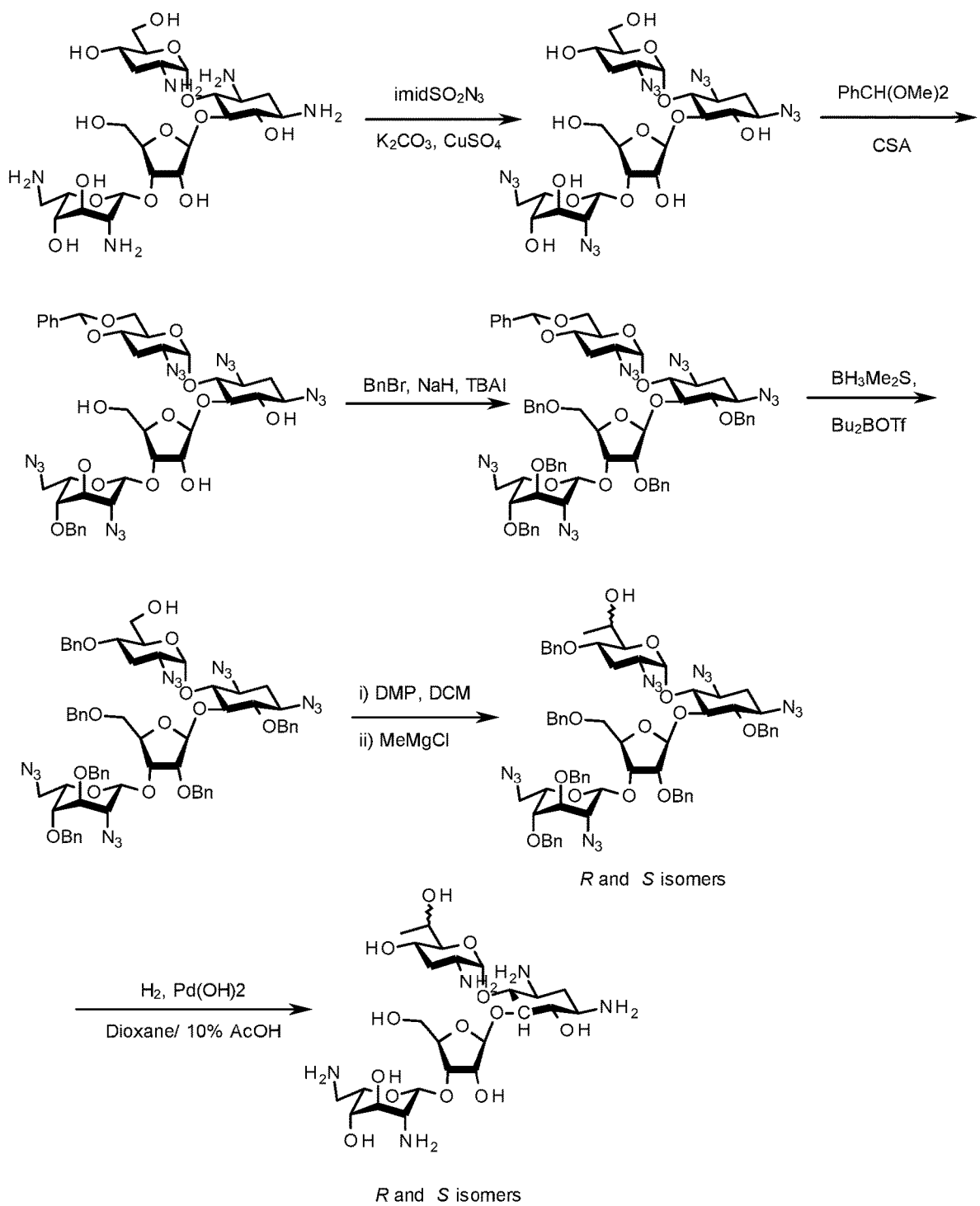
Figure 14:
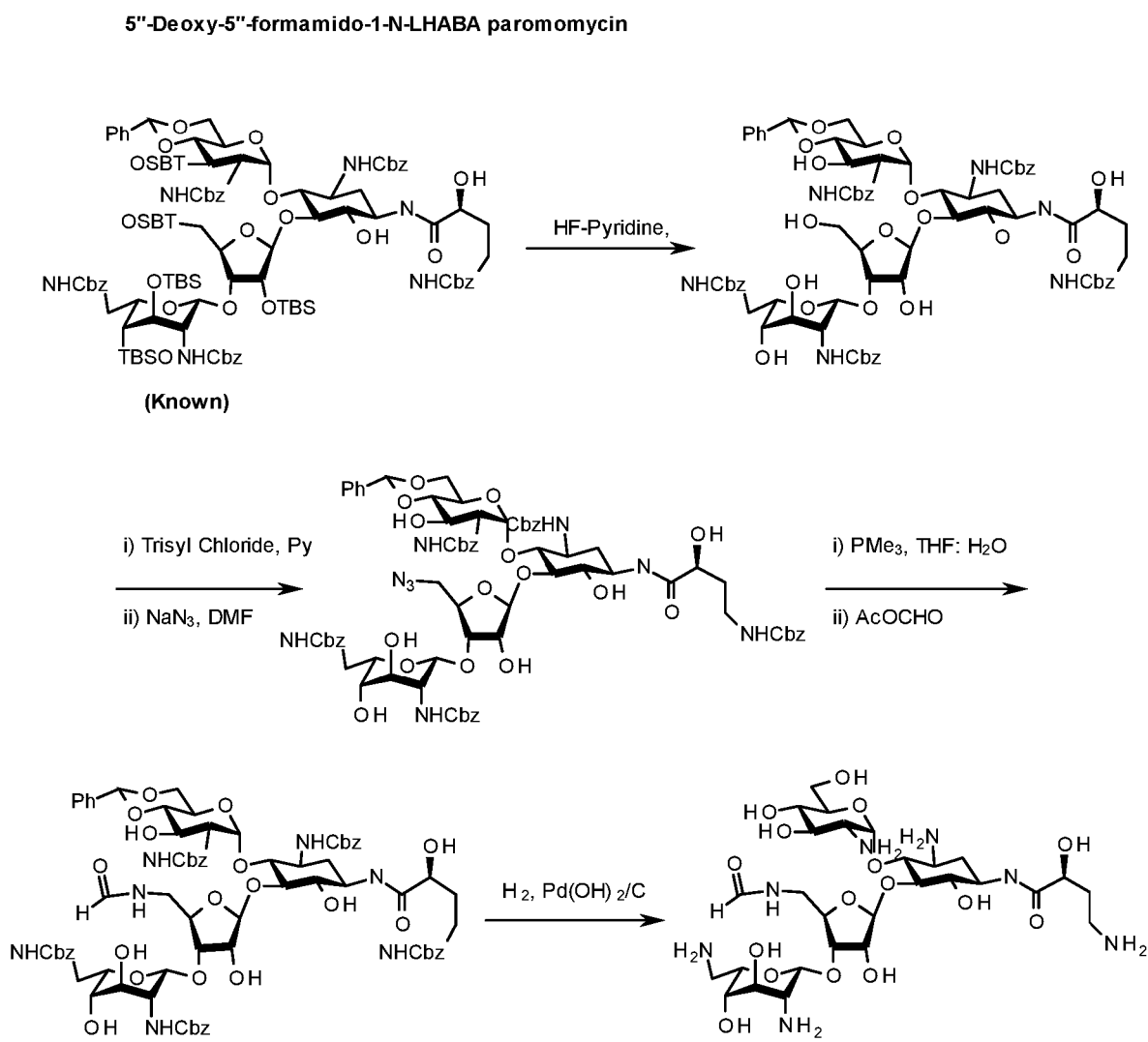
Figure 15:
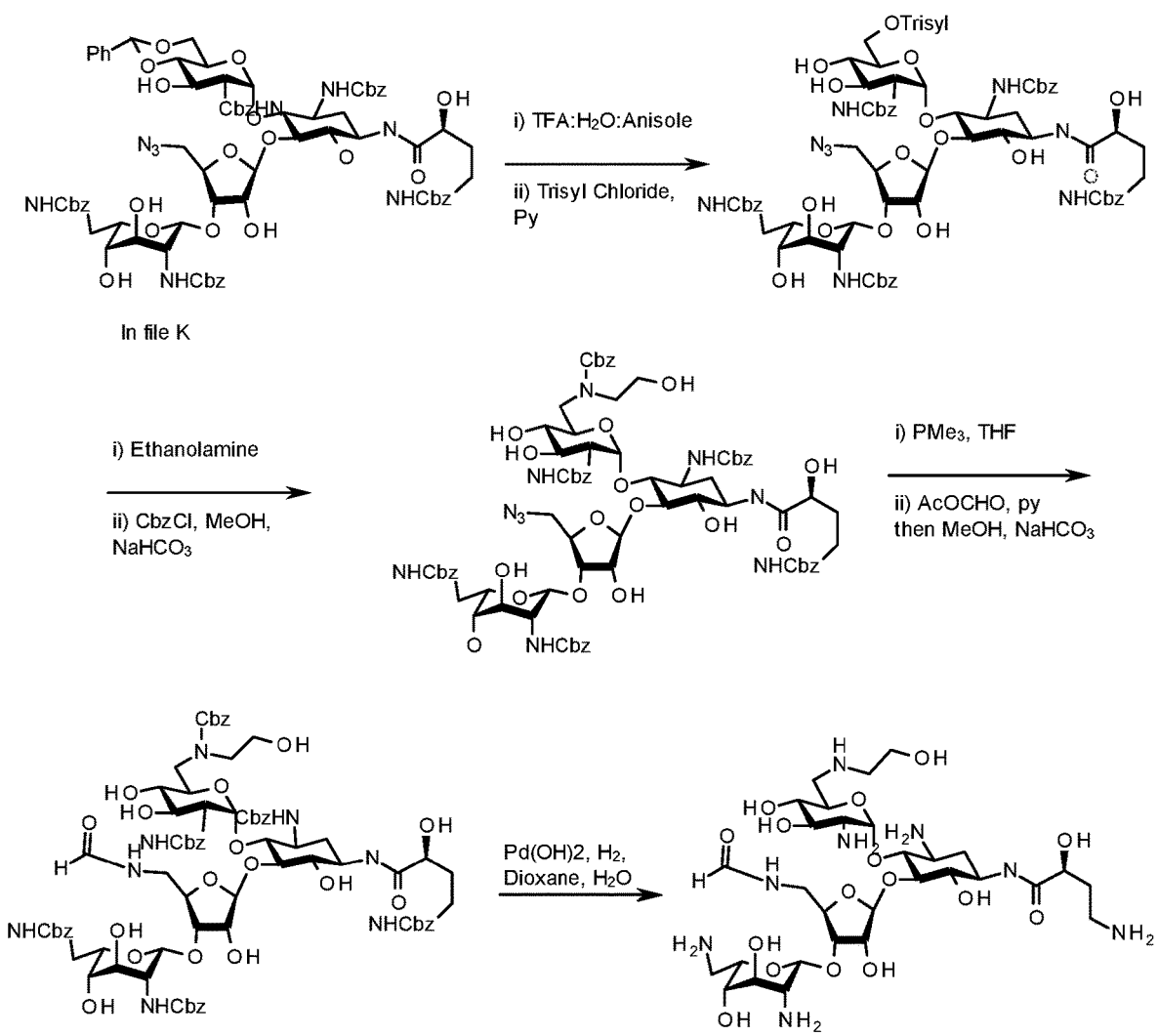
Figure 16:
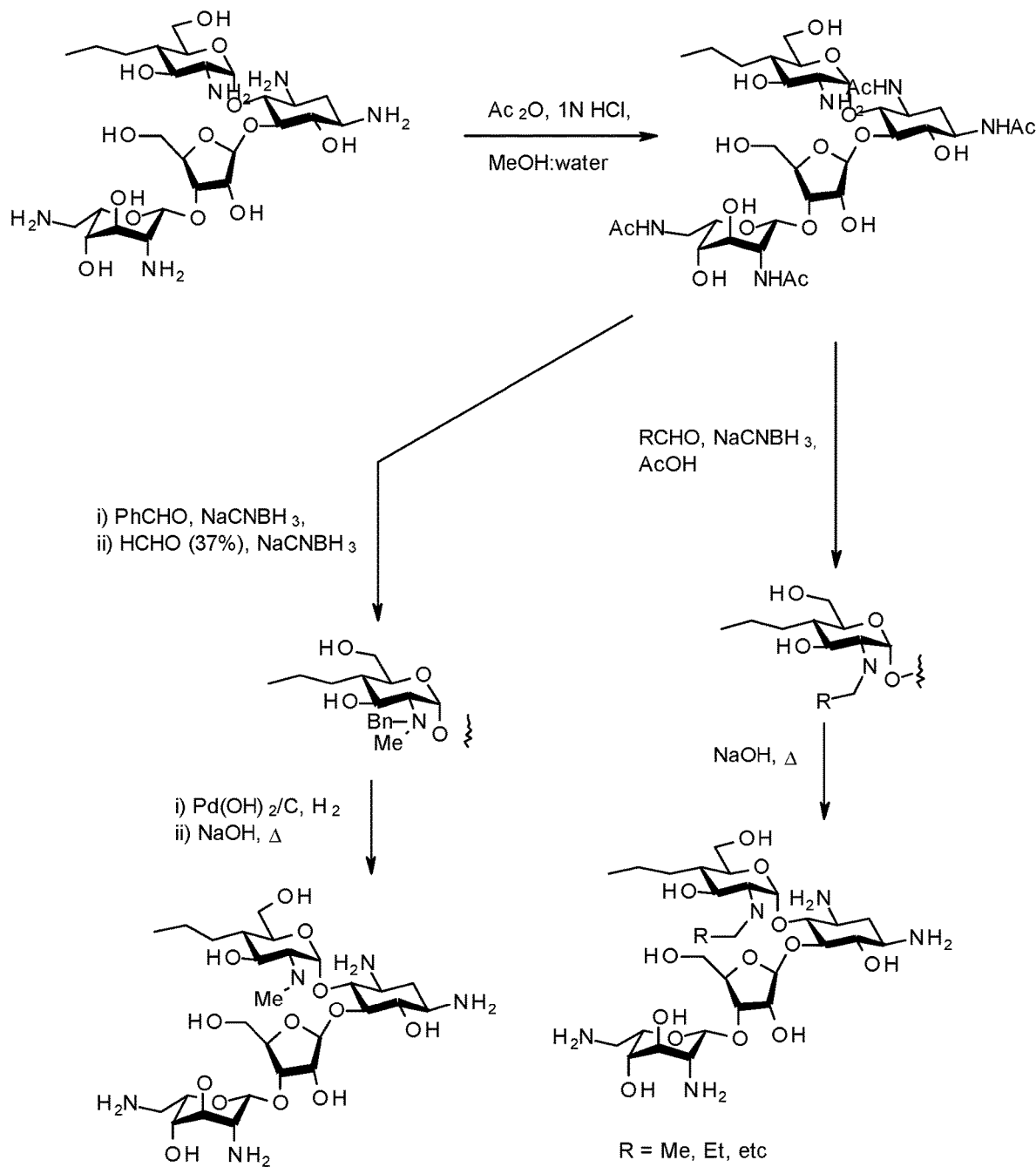
Figure 17A:
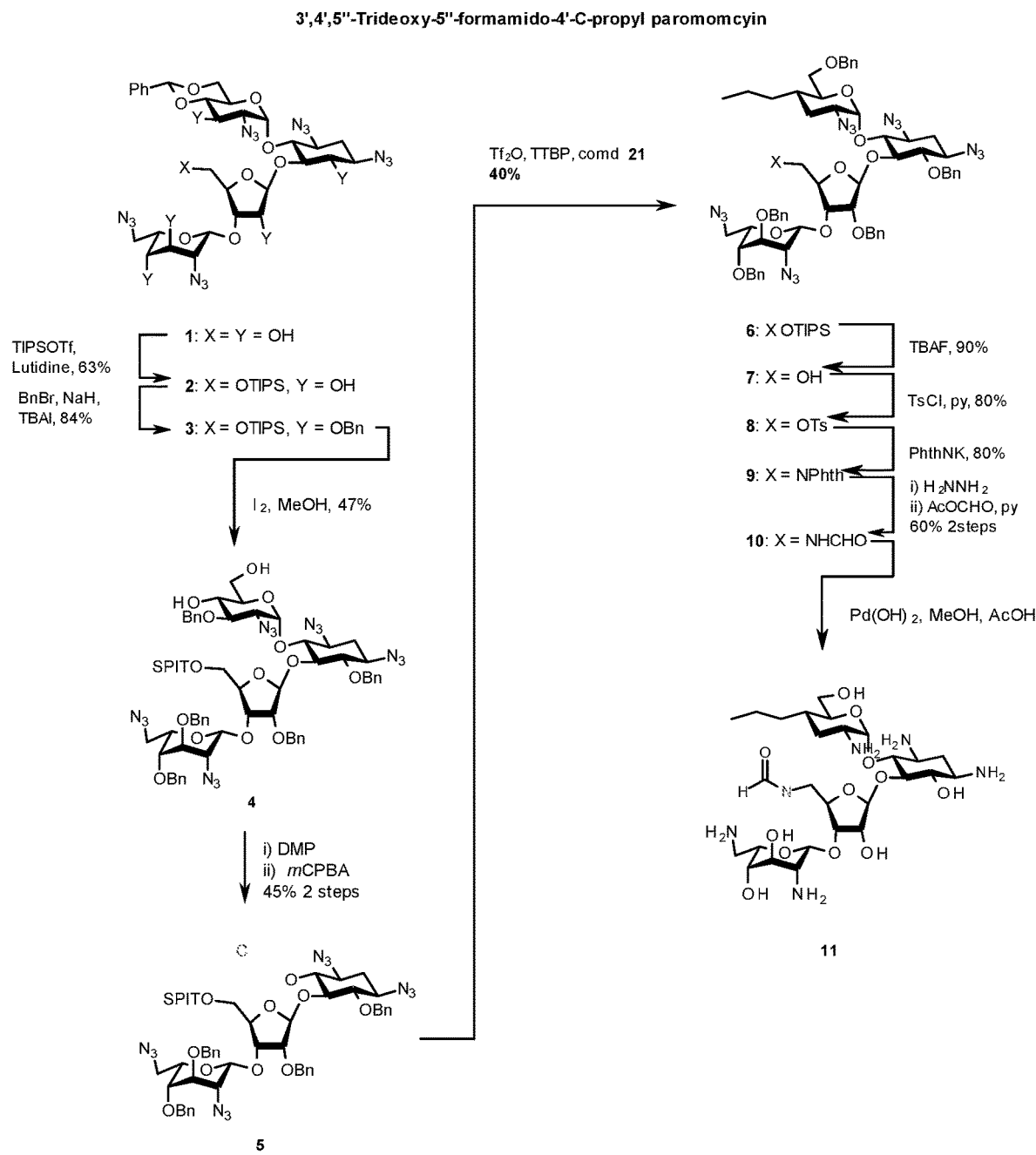
Figure 17B:
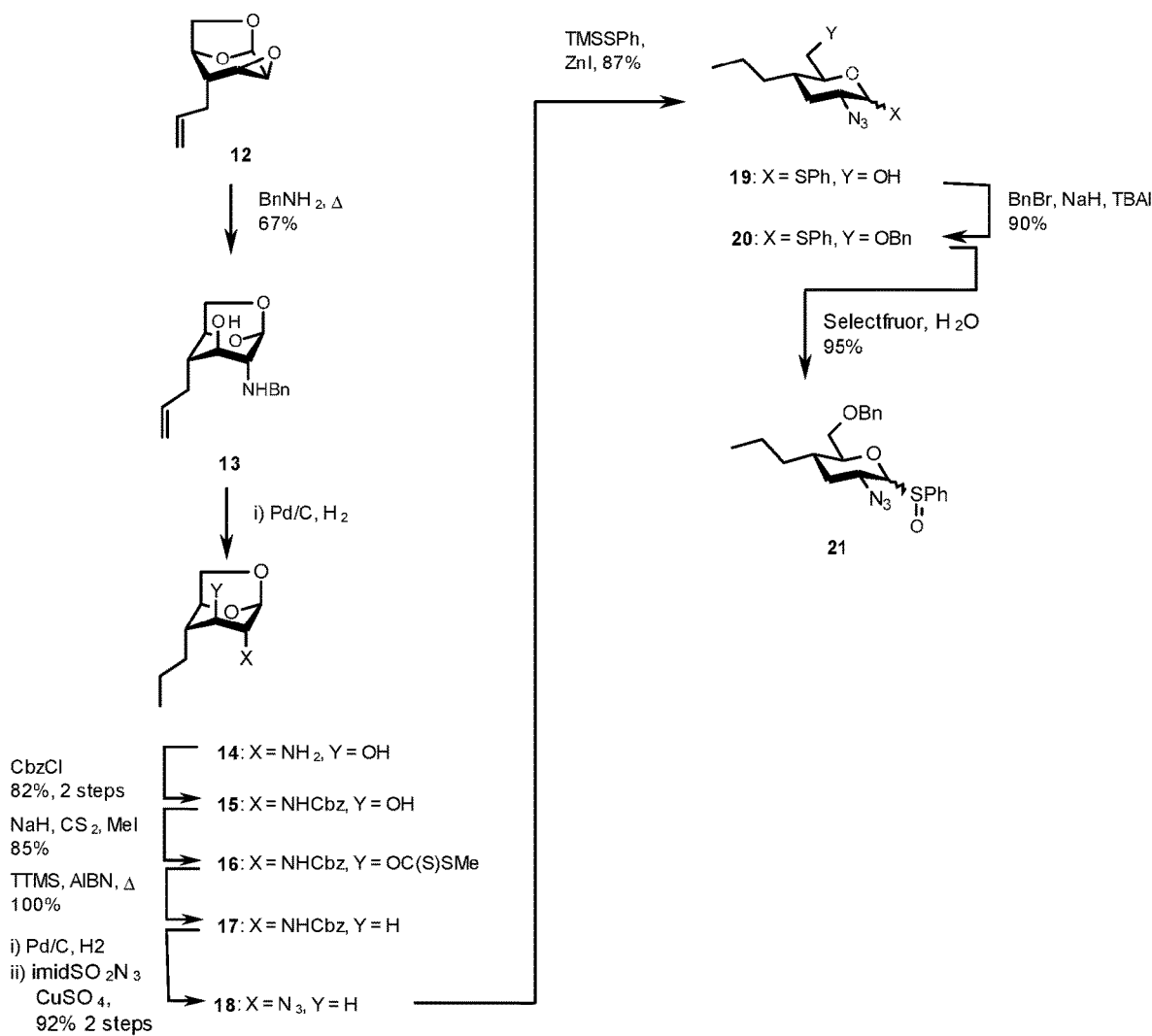
Figure 18:
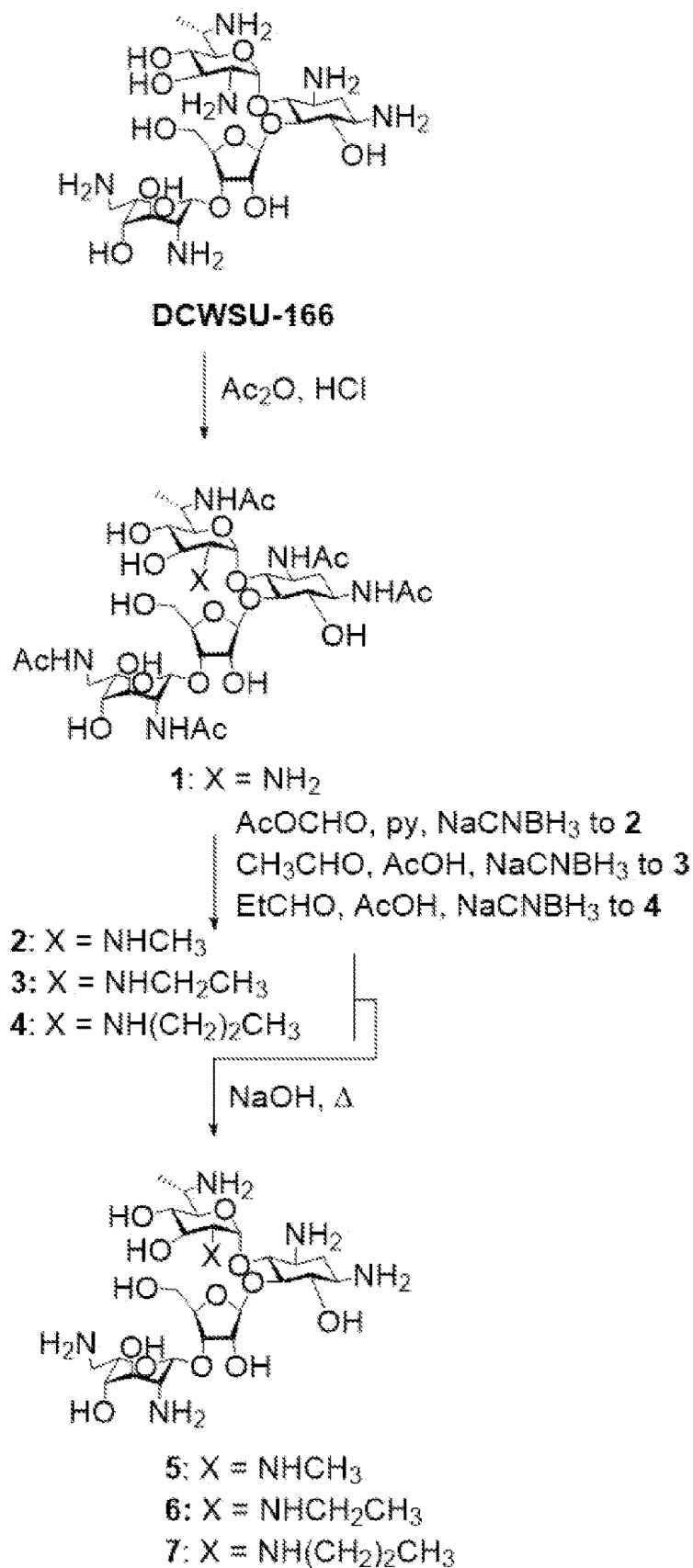
Figure 18:
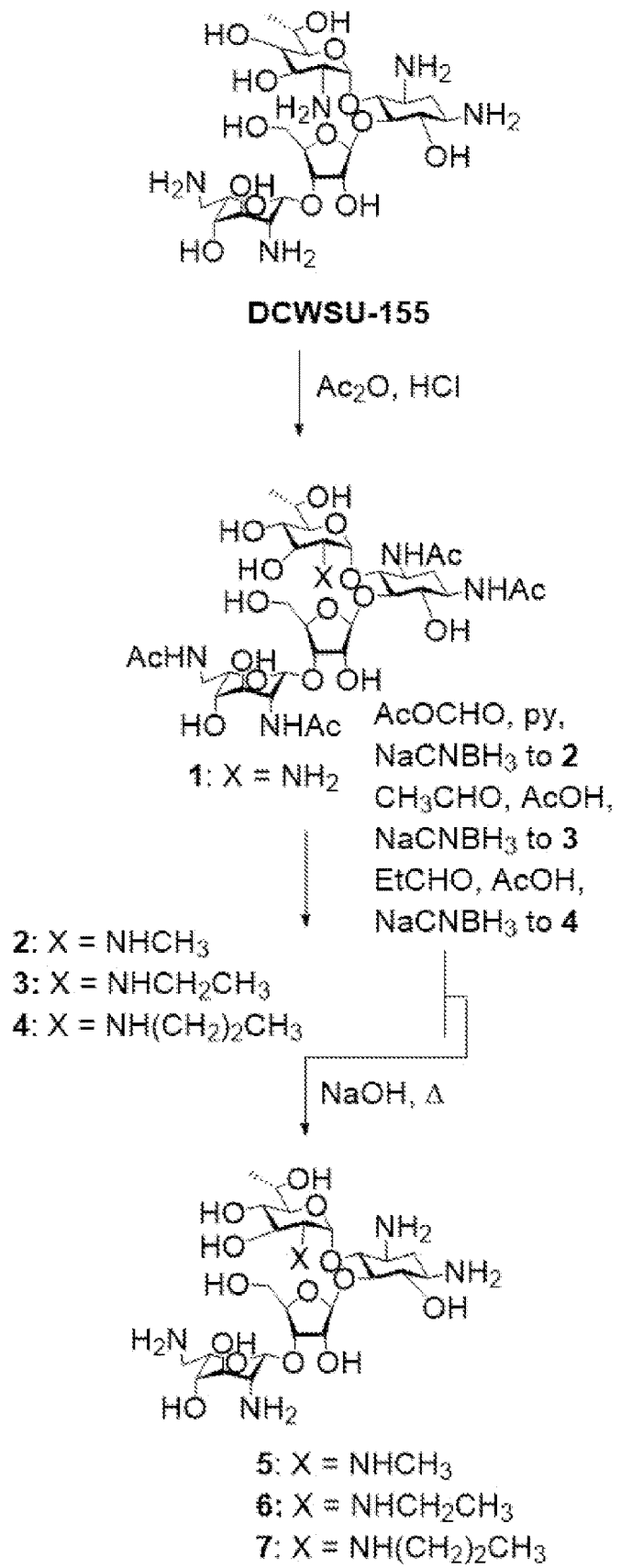
Figure 18:
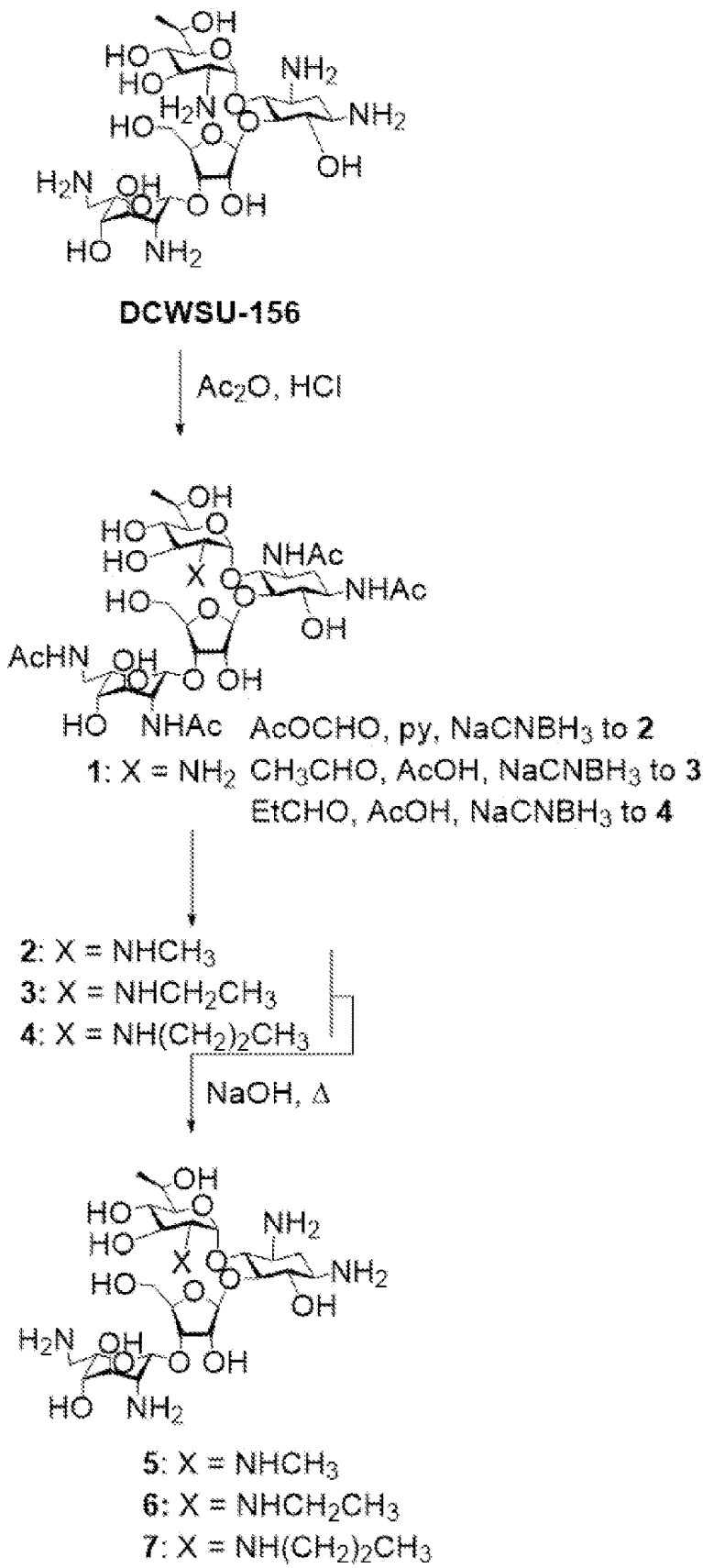

FIG. 6 show the synthesis of exemplary compounds disclosed herein, modified in position A, G and L.

EXAMPLES

General Methods and Materials.

Chemistry: All syntheses were run under an atmosphere of nitrogen or argon. Solvents were dried and purified by standard techniques.

Minimal inhibitory concentrations (MIC) have been determined by broth microdilution assays (CLSI. Methods for Dilution Antimicrobial Susceptibility Tests for Bacteria That Grow Aerobically; Approved Standard-Tenth Edition. CLSI document M07-A10. Wayne, Pa.: Clinical and Laboratory Standards Institute; 2015.). IC50 values for bacterial, human chimeric, and rabbit reticulocyte ribosomes have been determined by in-vitro translation assays as described previously (Proc. Nat. Ac. Sci USA 2012, 109(27):10984-10989).

Example 1: Modification of the 5" OH of Paromomycin or Neomycin (Position D)

Chemical synthesis of compounds modified in position D/the 5" carbon.

See the synthetic scheme of FIG. 1.

Particular embodiments encompass the compounds N, O and P of FIG. 1 and their use as an intermediate of an aminoglycoside drug derivative.

4',6'-O-Benzylidene-penta-N-benzyloxycarbonyl-5"-deoxy-5"-formamido-paromomycin (N)

A stirred solution of 4',6'-O-benzylidene-penta-N-benzyloxycarbonyl-5"-amino-5"-deoxy-paromomycin M (Hanessian et al. Antibiotics 1977, 30, 983) (250 mg, 0.18 mmol) in DCM (3 mL) was treated with formic acetic anhydride (3 mL) at RT. The reaction mixture was stirred for 2 h and then concentrated to dryness under reduced pressure. The residue was dissolved in MeOH (5 mL) and to this solution was added aq-NaHCO$_3$ (5 mL) at RT. The mixture was stirred for 1 h at RT and concentrated to dryness under reduced pressure. The residue was purified by column chromatography on silica gel eluting with CHCl$_3$/MeOH (49:1) to give N (175 mg, 69%). [α]$^{RT}_D$+44.3 (c 0.53, MeOH). ESIHRMS calculated for C$_{71}$H$_{80}$N$_6$O$_{24}$Na [M+Na]$^+$, 1423.5122; found, 1423.5095.

5"-Deoxy-5"-formamido-paromomycin acetate salt (137)

To a stirred suspension of Pd(OH)$_2$/C (160 mg, prewashed with glacial acetic acid) in water (2 mL) was added a solution of N (80 mg, 0.06 mmol) in dioxane (2 mL) at RT. The reaction mixture was stirred under a hydrogen atmosphere (45 psi) for 8 h, filtered, concentrated under reduced pressure, and purified by Sephadex C-25 column chromatography (0.6% NH$_4$OH). The product containing fractions were concentrated under reduced pressure. The residue was dissolved in 10%-AcOH and freeze dried to give 137 in the form of its acetate salt (25 mg, 26%). [α]$^{RT}_D$+44.0 (c 0.8, H$_2$O). ESIHRMS calculated for C$_{24}$H$_{47}$N$_6$O$_{14}$ [M+H]$^+$, 643.3150; found, 643.3145. This compound contained a second rotamer of the formamido group to the extent of 10%.

Penta-N-benzyloxycarbonyl-3',4',6'-hexa-O-acetyl-5"-deoxy-5"-acetamido-paromomycin (O)

A stirred solution of 4',6'-O-benzylidene-penta-N-benzyloxycarbonyl-5"-amino-5"-deoxy-paromomycin M (80 mg, 0.06 mmol) in DCM (1 mL) was treated with acetic anhydride (1 mL) at RT and stirred for 24 h at RT. Pyridine (1 mL) was then added and the reaction mixture was stirred for an additional 18 h at RT. The reaction mixture was concentrated to dryness under reduced pressure and the residue was purified by column chromatography on silica gel eluting with CHCl$_3$/MeOH (49:1) to give O (75 mg, 79%). [α]$^{RT}_D$+33.8 (c 0.94, MeOH). ESIHRMS calculated for C$_{79}$H$_{92}$N$_6$O$_{31}$Na [M+Na]$^+$, 1643.5705; found, 1643.5653.

5"-Acetamido-5"-deoxy-paromomycin-acetate salt (165)

To a stirred solution of O (75 mg, 0.05 mmol) in MeOH (1 mL) was added NaOMe (20 mg, 0.37 mmol) at RT. After stirring for 2 h, the reaction mixture was neutralized with Amberlyst (H-form), filtered, and concentrated under reduced pressure. The residue as dissolved in dioxane (1.5 ml) and was added to a stirred suspension of Pd/C (75 mg) in 10%-AcOH (0.75 mL). The reaction mixture was stirred under a hydrogen atmosphere (45 psi) for 18 h, filtered, concentrated under reduced pressure, and purified by Sephadex C-25 column chromatography (0.8% NH$_4$OH). The product-containing fractions were concentrated under reduced pressure. The residue was dissolved in 10%-AcOH and freeze dried to give 165 in the form of its acetate salt (26 mg, 49%). [α]$^{RT}_D$+55.7 (c 0.87, H$_2$O). ESIHRMS calculated for C$_{25}$H$_{49}$N$_6$O$_{14}$ [M+H]$^+$, 657.3307; found, 657.3273.

4',6'-O-Benzylidene-penta-N-benzyloxycarbonyl-5"-deoxy-5"-(3-N-benzylureido)-paromomycin (P)

A stirred solution of 4',6'-O-benzylidene-penta-N-benzyloxycarbonyl-5"-amino-5"-deoxy-paromomycin M (100 mg, 0.07 mmol) in DCM (1 mL) was treated with benzyl isocyanate (50 μL) at RT. The reaction mixture was stirred for 2 h, quenched with MeOH (5 mL), and concentrated to dryness under reduced pressure. The residue was purified by column chromatography on silica gel eluting with CHCl$_3$/MeOH (24:1) to give P (70 mg, 64%). [α]$^{RT}_D$+16.8 (c 0.9, MeOH). ESIHRMS calculated for C$_{73}$H$_{87}$N$_7$O$_{24}$Na [M+Na]$^+$, 1528.5700; found, 1527.5717.

5"-Deoxy-5"-ureido-paromomycin acetate salt (141)

To a stirred suspension of Pd/C (90 mg) in 80% AcOH (0.5 mL) was added a solution of P (30 mg, 0.02 mmol) in 80% AcOH (1.0 mL) at RT. The reaction mixture was stirred under a hydrogen atmosphere (45 psi) for 12 h, filtered, concentrated under reduced pressure, and purified by Sephadex C-25 column chromatography (0.7% NH$_4$OH). The product-containing fractions were concentrated under reduced pressure. The residue was dissolved in 10% AcOH and freeze dried to give 141 in the form of its acetate salt (8 mg, 42%). [α]$^{RT}_D$+18.5 (c 0.27, H$_2$O). ESIHRMS calculated for C$_{24}$H$_{48}$N$_7$O$_{14}$ [M+H]$^+$, 658.3259; found, 658.3258.

For a summary of the synthetic approach of the following steps, see FIG. 2.

Particular embodiments encompass the compounds BB, BC, BD, BE, BF, BG, BH, BI and BJ (see FIG. 2) and their use as an intermediate of an aminoglycoside drug derivative.

1,3,2',2''',6'''-Pentadeamino-1,3,2',2''',6'''-pentaazido-4',6'-O-benzylidene-5"-O-triisopropylsilyl-paromomycin (BB)

4',6'-O-Benzylidene penta-azidoparomomycin BA (Pathak, R.; Böttger, E. C.; Vasella, A. Helv. Chim. Acta 2005, 88, 2967) (4.16 g, 5 mmol) was dissolved in CH$_2$Cl$_2$ (80 mL), and treated with 2,6-utidine (3.07 mL, 25 mmol) and triisopropylsilyl trifluoromethanesulfonate (1.51 mL, 6 mmol) were added. The reaction mixture was stirred at room temperature for 1.5 h then diluted with ethyl acetate, washed with saturated aqueous sodium bicarbonate and brine. The organic layer was dried with sodium sulfate, filtered and concentrated. The residue was purified by flash column chromatography (hexane:ethyl acetate 1:4) to give BB as white solid (4.42 g, 89%). ESI-HRMS: m/z calculated for C$_{39}$H$_{59}$N$_{15}$NaO$_{14}$Si [M+Na]$^+$1012.4033, found 1012.4030.

1,3,2',2''',6'''-Pentadeamino-1,3,2',2''',6'''-pentaazido-6,3',2'',3''',4'''-penta-O-benzyl-4',6'-O-benzylidene-5"-O-triisopropylsilyl-paromomycin (BC)

Intermediate BB (3.94 g 3.97 mmol) was dissolved in THF (40 mL) and cooled to 0° C. in an ice bath. Sodium hydride (60% in mineral oil, 1.27 g, 31.8 mmol) was added slowly with stirring followed by benzyl bromide (4 mL, 31.8 mmol) and tetrabutylammonium iodide (148 mg, 0.4 mmol). The reaction mixture was allowed to warm up to room temperature and stirred for 15 h before cooling to 0° C. and addition of sufficient methanol to dissolve all solids. Saturated aqueous sodium bicarbonate was added and the mixture was extracted with ethyl acetate. The combined organic layer was washed with brine, dried with sodium sulfate, filtered and concentrated. The residue was purified by flash column chromatography (hexane:ethyl acetate 4:1) to give BC as a white solid (4.2 g, 73%) ESI-HRMS: m/z calculated for C$_{74}$H$_{89}$N$_{15}$NaO$_{14}$Si [M+Na]$^+$1462.6380, found 1462.6384.

6,3',2",3"',4"'-Penta-O-benzyl-1,3,2',2"',6"'-penta-N-(benzyloxycarbonyl)-4',6'-O-benzylidene-5"-O-triisopropylsilyl-paromomycin (BD)

Intermediate BC (4.2 g 2.92 mmol) was dissolved in THF (42 mL), and treated with trimethylphosphine solution (1M in THF, 23.3 mL, 23.3 mmol). The reaction mixture was heated to 65° C. with stirring for 1 h, then 0.1 M sodium hydroxide (42 mL) was added, and the mixture stirred at 65° C. for another 3 h before it was cooled to room temperature. N-(Benzyloxycarbonyloxy)succinimide (7.27 g, 29.2 mmol) and potassium carbonate (4.03 g, 29.2 mmol) were added and the mixture was stirred at room temperature for 15 h. Saturated aqueous sodium bicarbonate was added, and the mixture was extracted with ethyl acetate. The combined organic layer was washed with brine, dried with sodium sulfate, filtered and concentrated. The residue was purified by flash column chromatography (hexane:ethyl acetate 2:1) to give BD as a white solid (4.52 g, 78%). ESI-HRMS: m/z calculated for $C_{114}H_{129}N_5NaO_{24}Si$ [M+Na]$^+$ 2003.8728, found 2003.8725.

6,3',2",3"',4"'-Penta-O-benzyl-1,3,2',2"',6"'-penta-N-(benzyloxycarbonyl)-4',6'-O-benzylidene-paromomycin (BE)

Intermediate BD (1.98 g, 1 mmol) was dissolved in THF (50 mL), and treated with tetrabutylammonium fluoride solution (1 M in THF, 2 mL, 2 mmol) followed by stirring at room temperature for 1 h. The reaction mixture was concentrated and the residue was purified by flash column chromatography (hexane:ethyl acetate 1:1) to give BE as a white solid (1.64 g, 90%) ESI-HRMS: m/z calculated for $C_{15}H_{109}N_5NaO_{24}$ [M+Na]$^+$1847.7394, found 1847.7396.

5"-Azido-6,3',2",3"',4"'-penta-O-benzyl-1,3,2',2"',6"'-penta-N-(benzyloxycarbonyl)-4',6'-O-benzylidene-5"-deoxy-paromomycin (BF)

Intermediate BE (1.21 g, 0.66 mmol) was dissolved in $CH_2Cl_2$ (12 mL), 4-toluenesulfonyl chloride (1.28 g, 6.6 mmol), triethylamine (1.8 mL, 13.2 mmol) and 4-dimethylaminopyridine (80 mg, 0.66 mmol) were added and the reaction mixture was stirred at room temperature for 16 h. The reaction mixture was diluted with ethyl acetate, washed with saturated aqueous sodium bicarbonate, 1 M HCl and brine. The organic layer was dried with sodium sulfate, filtered and concentrated. The residue was dissolved in dimethylformamide (12 mL), sodium azide (430 mg, 6.6 mmol) was added and the reaction mixture was stirred at 65° C. for 15 h, then cooled to room temperature, diluted with ethyl acetate, and washed with saturated sodium aqueous bicarbonate solution and brine. The organic layer was dried with sodium sulfate, filtered and concentrated. The residue was purified by flash column chromatography (hexane:ethyl acetate 2:1) to give BF as a white solid (1.08 g, 88%). ESI-HRMS: m/z calculated for $C_{15}H_{109}N_8NaO_{23}$ [M+Na]$^+$ 1872.7459, found 1872.7458.

6,3',2",3"',4"'-Penta-O-benzyl-1,3,2',2"',6"'-penta-N-(benzyloxycarbonyl)-4',6'-O-benzylidene-5"-deoxy-5"-formamido-paromomycin (BG)

Intermediate BF (1.57 g, 0.85 mmol) was dissolved in THF (16 mL), trimethylphosphine (1 M in THF, 1.7 mL, 1.7 mmol) was added and the reaction mixture was stirred at 65° C. for 1 h. DI water (16 mL) was added and stirring was continued at 65° C. for another 3 h. The reaction mixture was concentrated and dried then was dissolved in $CH_2Cl_2$ (16 mL), and formic acetic anhydride (1.6 mL) was added followed by stirring at room temperature for 1 h. The reaction mixture was evaporated to dryness and the residue was purified by flash column chromatography (hexane:ethyl acetate 1:2) to give BG as a white solid (1.06 g, 67%). ESI-HRMS: m/z calculated for $C_{106}H_{110}N_6NaO_{24}$ [M+Na]$^+$ 1874.7503, found 1874.7505.

6,3',6',2",3"',4"'-Hexa-O-benzyl-1,3,2',2"',6"'-penta-N-(benzyloxycarbonyl)-5"-deoxy-5"-formamido-paromomycin (BH)

Intermediate BG (1.06 g, 0.57 mmol) was dissolved in THF (10 mL) and stirred with activated 4-A molecular sieves at room temperature for 1 h before sodium cyanoborohydride (730 mg, 11.5 mmol) and methyl orange (1 mg) were added. The reaction mixture was cooled to 0° C. and 2 M HCl in diethyl ether (11.5 mL, 23 mmol) was added drop wise after which the reaction mixture was stirred at 0° C. for 2 h. The reaction mixture was poured into ice-cold saturated aqueous sodium bicarbonate and extracted with ethyl acetate. The combined organic layer was washed with brine, dried with sodium sulfate, filtered, and concentrated. The residue was purified by flash column chromatography (hexane:ethyl acetate 1:2) to give BH as a white solid (804 mg, 75%). ESI-HRMS: m/z calculated for $C_{106}H_{112}N_6NaO_{24}$ [M+Na]$^+$1876.7659, found 1876.7663.

6,3',6',2",3"',4"'-Hexa-O-benzyl-1,3,2',2"',6"'-penta-N-(benzyloxycarbonyl)-5"-deoxy-5"-formamido-4'-keto-paromomycin (BI)

Intermediate BH (804 mg, 0.43 mmol) was dissolved in $CH_2Cl_2$ (8 mL) and Dess-Martin periodinane (276 mg, 0.65 mmol) was added. The reaction mixture was stirred at room temperature for 7 h, then diluted with ethyl acetate, washed with saturated sodium aqueous bicarbonate and brine. The organic layer was dried with sodium sulfate, filtered and concentrated. The residue was purified by flash column chromatography (hexane:ethyl acetate 1:2) to give intermediate BI as a white solid (574 mg, 72%). ESI-HRMS: m/z calculated for $C_{106}H_{110}N_6NaO_{24}$ [M+Na]$^+$1874.7503, found 1874.7505.

6,6',2",3"',4"'-Penta-O-benzyl-1,3,2',2"',6"'-penta-N-(benzyloxycarbonyl)-3',5"-dideoxy-5"-formamido-paromomycin (BJ)

A solution of intermediate BI (300 mg, 0.16 mmol) in THF (1 mL) was cooled to −20° C. and treated with samarium(II) iodide (0.1 M in THF, 10 mL, 1 mmol) was added followed by stirring at −20° C. for 1 h. Methanol (38 μL, 1 mmol) was added and the reaction mixture was warmed to 0° C. and stirred for 2 h. Saturated aqueous sodium bicarbonate was added at 0° C. and the mixture was extracted with ethyl acetate. The combined organic layer was washed with brine, dried by sodium sulfate, filtered and concentrated. The residue was purified by flash column chromatography (hexane:ethyl acetate 1:3) to give intermediate BJ as a white solid (84 mg, 30%). ESI-HRMS: m/z calculated for $C_{99}H_{106}N_6NaO_{23}$ [M+Na]$^+$1770.7241, found 1770.7245.

3',5"-Dideoxy-5"-formamido-paromomycin (153)

Intermediate BJ (17.5 mg, 0.01 mmol) was dissolved in dioxane (0.2 mL), and 10% acetic acid (0.2 mL) and palladium hydroxide on carbon (17 mg) were added. The reaction mixture was stirred under a hydrogen atmosphere (48 psi) for 12 h, then was filtered, concentrated and purified by Sephadex C-25 column chromatography (0.17% ammonium hydroxide). The product-containing fractions were combined, acetic acid (41 µL, 0.69 mmol) was added, and the mixture was freeze dried to give 153 as a white solid in the form of the acetate salt (4.6 mg, 50%). ESI-HRMS: m/z calculated for $C_{24}H_{47}N_6O_{13}$ $[M+H]^+$ 627.3201, found 627.3197.

Biological testing of compounds modified in position D/the 5" carbon.

Compound 165 is shown as a comparative example.

In certain aspects of the data provided herein, the inventors demonstrate that combined substitutions at both C3' and C5" provides full protection against all relevant isoforms of APH(3'). A novel 5"-deoxy-5"-formamido substitution is described which retains full antibacterial activity when compared to the parent compound. Target specificity for the bacterial versus the human cytosolic decoding site is increased for some modifications.

TABLE 1

(Example 1). Position D: Activity Against Wild Type Isolates ($MIC_{50}$ µg/ml)

| | MRSA | | | | E coli | | | P aeruginosa | | | |
|---|---|---|---|---|---|---|---|---|---|---|---|
| Cmpd | AG38 | AG39 | AG42 | AG44 | AG03 | AG01 | AG55 | AG31 | AG32 | AG33 | AG86 |
| paromomycin | 4 | >256 | >256 | 4-8 | 4 | 2-4 | 2-4 | >128 | >128 | >128 | >128 |
| Lividomycin B | 4 | >128 | >128 | 4-8 | 8-16 | 16 | 16 | 16 | >128 | 128 | 128 |
| Paromomycin derivs | | | | | | | | | | | |
| 137 | 4 | >128 | >128 | 2-4 | 4 | 4 | 4 | 128 | 128 | >128 | >128 |
| 141 | 4-8 | >128 | >128 | 4 | 16 | 16 | 16 | >128 | >128 | >128 | >128 |
| 165 | 16-32 | >128 | >128 | 16 | 32-64 | 64 | 32 | >128 | >128 | >128 | >128 |
| 153 | 4 | >128 | >128 | 4 | 8 | 8-16 | 8-16 | 32-64 | 32 | >32 | nd |

TABLE 2

(Example 1). Position D modified compounds in E coli carrying specific resistance determinants (MIC µg/ml)

| Resistance Det. | AG160 wt | AG173 AAC(3)-IV | AG163/164 APH(3')-Ia | AG166 APH(3')-IIa | AG182 AAC(3)-IV APH(3')-Ia | AG102 | AG103 Arm A | AG006 wt | AG007 ANT(3") AAC(3)-I |
|---|---|---|---|---|---|---|---|---|---|
| paromomycin | 2-4 | 2-4 | >128 | >128 | >128 | 1 | 1-2 | 1-2 | 4 |
| Lividomycin B | 4 | nd | >128 | 4-8 | nd | 2 | 16 | 1-2 | 4 |
| Paromomycin derivs | | | | | | | | | |
| 137 | 2 | nd | 32-64 | >128 | nd | 1 | 8 | 1 | 4 |
| 141 | nd | nd | nd | nd | nd | nd | nd | 1 | nd |
| 165 | nd | nd | nd | nd | nd | nd | nd | 4-8 | nd |
| 153 | 2-4 | nd | 4-8 | 8-16 | nd | 2 | 32 | 2 | 4 |

TABLE 3

(Example 1): Position D:

| | | | MIC (µg/mL) | | | | IC50 (µM) | | |
|---|---|---|---|---|---|---|---|---|---|
| Compound | 3' | 5" | WT | APH(3')-I | APH(3')-II | APH(3')-III | APH(3)-VI | Bac | Mit | Cyt |
| Paromomycin | OH | OH | 1-2 | >64 | >64 | >64 | >64 | 0.04 | 140 | 31 |
| Lividomycin B | H | OH | 2 | >64 | 2 | >64 | 2 | 0.04 | 109 | 53 |
| 137 | OH | Form. | 1-2 | >64 | >64 | >64 | >64 | 0.04 | 144 | 90 |
| 153 | H | Form. | 2 | 2 | 2 | 2 | 2-4 | 0.12 | 144 | 90 |
| DC-194 | OH | Form. | 2 | 8 | 2-4 | 2 | 2 | 0.04 | 275 | 102 |
| DC-194 | OH | Form. | 2 | 8 | 2-4 | 2 | 2 | 0.04 | 275 | 102 |
| Neomycin | OH | OH | 1 | >64 | 64 | >64 | 32-64 | 0.04 | 4.3 | 35 |
| 140 | H | OH | 1 | >32 | 1 | 32 | 1 | 0.04 | 4.6 | 66 |
| Ribostamycin | OH | OH | 2 | >64 | >64 | 32-64 | >64 | 0.09 | 443 | 484 |
| 047 | H | OH | 2-4 | >64 | 2-4 | >64 | 4 | 0.10 | 325 | 293 |
| 048 | OH | NH2 | 2-4 | >64 | >64 | >64 | 64 | 0.09 | 76 | 50 |
| 130 | OH | Form. | 4 | >64 | >64 | >64 | >64 | 0.24 | 364 | 359 |

Example 2: Modification of Ring I in C4' and 5' by a Six-Ring System or by Alkylation in C6' (Position A). Target Specificity for the Bacterial Versus the Human Cytosolic Decoding Site is Increased for Some Modifications The preparation of a series of four analogues of the aminoglycoside antibiotics neomycin and paromomycin is described in which ring I, involved in critical binding interactions with the ribosomal target, is replaced by an apramycin-like dioxabicyclo[4.4.0]octane system. The effect of this modification is to lock the hydroxymethyl side chain of the neomycin or paromomycin ring I, as part of dioxabicyclooctane ring, into either the gauche-gauche or the gauche-trans conformation (respectively axial or equatorial to the bicyclic system). The antiribosomal activity of these compounds was investigated with cell-free translation assays using both wild type bacterial ribosomes and hybrid ribosomes carrying eukaryotic decoding A sites enabling the prediction of selectivity. Compounds substituted with an equatorial hydroxyl or amino group are considerably more active than their axial diastereomers lending strong support to crystallographically-derived models of aminoglycoside-ribosome interactions. One such bicyclic compound carrying an equatorial hydroxyl group has activity equal to that of the parent, yet displays better ribosomal selectivity, predictive of an enhanced therapeutic index. A paromomycin analog lacking the hydroxymethyl ring I side chain is considerably less active than the parent. Antibacterial activity against model Gram negative and Gram positive bacteria is reported, for selected compounds, as is activity against engineered bacteria carrying specific resistance determinants. Analogues with a bicyclic ring I carrying equatorial amino or hydroxyl groups mimicking the bound side chains of neomycin and paromomcyin, respectively, show excellent activity and by virtue of their novel structure retain this activity in strains that are insensitive to the parent compounds.

Synthesis: Experimental and Characterization Data for compounds 109, 125, 139 and 150.

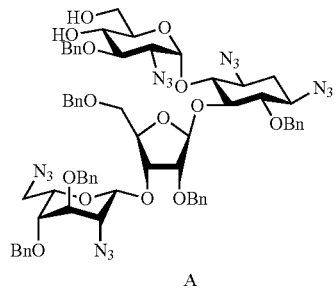

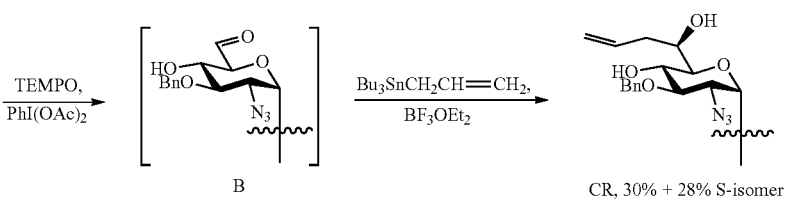

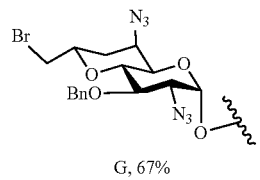

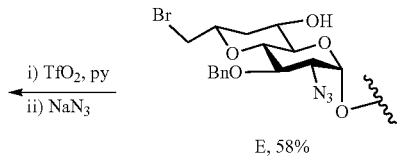

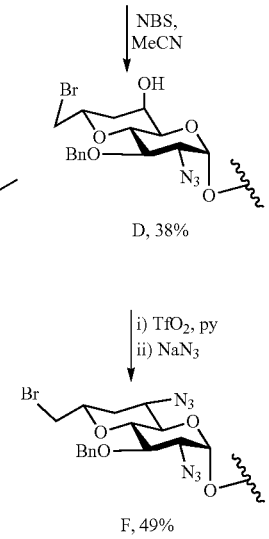

Particular embodiments encompass the compounds A, C, D, E, F and G of the preceding scheme and their use as an intermediate of an aminoglycoside drug derivative.

6'-Allyl-1,3,2',2''',6'''-pentadeamino-1,3,2',2''',6'''-pentaazido-6,3',2'',5'',3''',4'''-hexa-O-benzyl-paromomycin (CR)

To a stirred solution of A (Pathak et al., Helv. Chim. Acta 2008, 91, 1533) (1.0 g, 0.77 mmol) under Ar in anhydrous dichloromethane (20.0 mL) was added bis(acetoxy)iodobenzene (300.0 mg, 0.93 mmol) followed by a catalytic amount of TEMPO (12.0 mg, 0.08 mmol) in one portion at room temperature. The resulting reaction mixture was stirred for 12 h at room temperature and was quenched with saturated aqueous $Na_2S_2O_3$, washed with saturated aqueous $NaHCO_3$, brine, dried over $Na_2SO_4$, and concentrated under reduced pressure to give the crude aldehyde B. To a solution of this aldehyde in anhydrous dichloromethane (10.0 mL) at 0° C. under Ar was added allyltributyltin (1.29 g, 3.89 mmol) followed by boron trifluoride ethyl etherate (133.0 mg, 0.04 mmol). The resulting reaction mixture was stirred at 0° C. for 2 h before it was quenched with saturated aqueous $NaHCO_3$. The combined extracts were washed with brine, dried over $Na_2SO_4$, filtered, and concentrated to a afford gum. The crude product was purified via silica gel column chromatography (eluent: 2%-30% EtOAc in hexane) to give CR (295 mg, 30%, over 2 steps) and its S-isomer (293 mg, 28%, over 2 steps), as yellow foams.

CR: $[\alpha]_D^{26}$=+82.5 (c=0.20, dichloromethane); ESI-HRMS: m/z calculated. for $C_{68}H_{75}N_{15}O_{14}Na$ [M+Na]$^+$ 1348.5516, found: 1348.5491.

4-O-(2'-Azido-3',6'-di-O-benzyl-9'-bromo-4',8'-anhydro-2',7',9'-trideoxy-D-erythro-α-D-gluco-nonapyranosyl)-5-O-[3"-O-(2''',6'''-diazido-3''',4'''-di-O-benzyl-2''',6'''-dideoxy-β-L-idopyranosyl)-2'',5''-di-O-benzyl-β-D-ribofuranosyl]-1,3-diazido-6-O-benzyl-2-deoxystreptamine (D)

A stirred solution of CR (480.0 mg, 0.36 mmol) in anhydrous acetonitrile (5.0 mL) was treated with N-bromosuccinimide (66.4 mg, 0.37 mmol) at 0° C. The resulting reaction mixture was stirred at 0° C. for 12 h, then diluted with ethyl acetate (10.0 mL) and was washed with brine (5.0 mL). The organic layer was concentrated to afford a yellow oil that was purified by chromatography on silica gel (EtOAc/hexane 3% to 30%) to afford D (196.0 mg, 38%) as a white foam. $[\alpha]_D^{26}$=+73.0 (c=0.46, dichloromethane); ESI-HRMS: m/z calculated. for $C_{68}H_{74}N_{15}O_{14}BrNa$ [M+Na]$^+$1428.4600, found: 1428.4596.

4-O-(2'-Azido-3',6'-di-O-benzyl-9'-bromo-4',8'-anhydro-2',7',9'-trideoxy-D-threo-α-D-gluco-nonapyranosyl)-5-O-[3"-O-(2''',6'''-diazido-3''',4'''-di-O-benzyl-2''',6'''-dideoxy-β-L-idopyranosyl)-2'',5''-di-O-benzyl-β-D-ribofuranosyl]-1,3-diazido-6-O-benzyl-2-deoxystreptamine (E)

A solution of D (150.0 mg, 0.11 mmol) in dry dichloromethane (5.0 mL) was treated with Dess-Martin periodinane (90.6 mg, 0.21 mmol) and sodium bicarbonate (18.0 mg, 0.21 mmol), and stirred for 9 h under Ar at room temperature. The reaction mixture was washed with water followed by brine, dried, and concentrated under reduced pressure. The crude ketone (115 mg, 0.08 mmol) was stirred with NaBH$_4$ (6.2 mg, 0.16 mmol) in methanol (4.0 mL) for 30 min. The reaction mixture was neutralized with acetic acid and concentrated under reduced pressure. The crude mixture of diastereomers (3:1 ratio) was separated by silica gel column using 30% EtOAc in hexanes to give the title compound E (66.0 mg, 58%) as a white foam. $[\alpha]_D^{26}$=+67.9 (c=0.19, dichloromethane); ESI-HRMS: m/z calculated. for $C_{68}H_{74}N_{15}O_{14}BrNa$ [M+Na]$^+$1428.4600, found: 1428.4626.

4-O-(2',6'-Diazido-3',6'-di-O-benzyl-9'-bromo-4',8'-anhydro-2',6',7',9'-tetradeoxy-D-threo-α-D-gluco-nonapyranosyl)-5-O-[3"-O-(2''',6'''-diazido-3''',4'''-di-O-benzyl-2''',6'''-dideoxy-β-L-idopyranosyl)-2'',5''-di-O-benzyl-β-D-ribofuranosyl]-1,3-diazido-6-O-benzyl-2-deoxystreptamine (F)

To a stirred solution of D (90.0 mg, 0.06 mmol) in dry dichloromethane (1.0 mL) and pyridine (21.7 mg, 0.27 mmol) at 0° C. under Ar was added triflic anhydride (40 mg, 0.14 mmol). The reaction mixture was stirred at 0° C. for 1 h and was quenched with saturated aqueous NaHCO$_3$. The reaction mixture was washed with brine, dried over Na$_2$SO$_4$, filtered, and concentrated under reduced pressure. The crude product was stirred with sodium azide (20.0 mg, 0.30 mmol) in dry DMF (0.5 mL) at room temperature for 6 h after which the solvent was evaporated under reduced pressure. The residue was dissolved in dichloromethane (2.0 mL) and washed with water, brine, dried over Na$_2$SO$_4$, filtered, and concentrated under reduced pressure. The crude product was purified via silica gel chromatography (eluent: 2% to 20% EtOAc in hexanes) to give F (45.0 mg, 49%) as a colorless oil. $[\alpha]_D^{26}$=+51.0 (c=0.6, dichloromethane); ESI-HRMS: m/z calculated. for $C_{68}H_{73}N_{18}O_{13}BrNa$ [M+Na]$^+$ 1451.4686, found: 1451.4667.

4-O-(2',6'-Diazido-3',6'-di-O-benzyl-9'-bromo-4',8'-anhydro-2',6',7',9'-tetradeoxy-D-erythro-α-D-gluco-nonapyranosyl)-5-O-[3"-O-(2''',6'''-diazido-3''',4'''-di-O-benzyl-2''',6'''-dideoxy-3-L-idopyranosyl)-2'',5''-di-O-benzyl-β-D-ribofuranosyl]-1,3-diazido-6-O-benzyl-2-deoxystreptamine (G)

To a stirred solution of E (70.0 mg, 0.05 mmol) in dry dichloromethane (1.5 mL) and dry pyridine (17.0 mg, 0.22 mmol) at 0° C. under Ar was added triflic anhydride (31.0 mg, 0.11 mmol). The reaction mixture was stirred at 0° C. for 1 h and was quenched with saturated aqueous NaHCO$_3$ and washed with brine, dried, filtered, and concentrated under reduced pressure. The crude product was stirred with sodium azide (32.0 mg, 0.49 mmol) in dry DMF (0.7 mL) at room temperature for 4 h after which the solvent was evaporated under reduced pressure. The residue was dissolved in dichloromethane (3.0 mL) and washed with water, brine, dried over Na$_2$SO$_4$, filtered, and concentrated under reduced pressure. The crude product was purified via silica gel chromatography eluting with 2% to 30% EtOAc in hexanes to give G (61.0 mg, 67%) as an off-white foam. $[\alpha]_D^{26}$=+132.1 (c=0.11, dichloromethane); ESI-HRMS: m/z calculated. for $C_{68}H_{73}N_{18}O_{13}BrNa$ [M+Na]+1451.4686, found: 1451.4679.

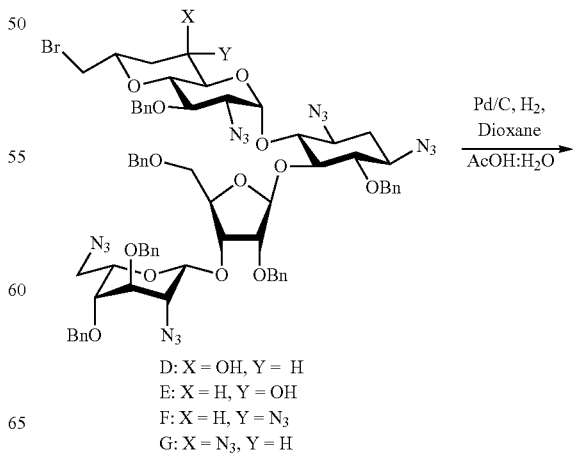

D: X = OH, Y = H
E: X = H, Y = OH
F: X = H, Y = N$_3$
G: X = N$_3$, Y = H

-continued

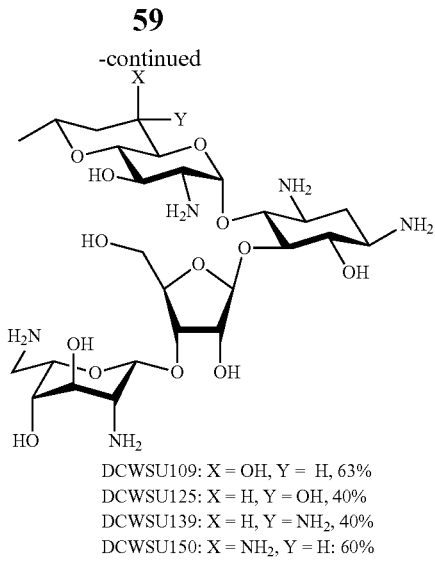

DCWSU109: X = OH, Y = H, 63%
DCWSU125: X = H, Y = OH, 40%
DCWSU139: X = H, Y = NH₂, 40%
DCWSU150: X = NH₂, Y = H: 60%

General procedure A for hydrogenolysis. A stirred solution of substrate (0.02 mmol) in a mixture of 1,4-dioxane (0.5 mL), deionized water H2O (0.2 mL), and glacial acetic acid (20 µL) was treated with Pd/C on carbon (20 wt. %, 100% loading) and stirred for 48 h at room temperature under 40 psi of hydrogen. After completion, the reaction mixture was filtered through Celite® and the filtrate was evaporated under reduced pressure to give the crude product. The residue was dissolved in 0.002 M aqueous AcOH (2.0 mL) and then charged to a Sephadex column (CM Sephadex C-25, 5.0 g). The Sephadex column was eluted with deionized water (50 mL), 0.5% aqueous NH4OH (40 mL), and 1.5% NH4OH (40 mL). The product-containing fractions were combined and evaporated to give the product in the form of the free base, which was taken up in H2O (2 mL) and treated with glacial acetic acid (10 eq). The resulting solution was lyophilized to give the product in the form of the acetate salt.

4-O-(2'-Amino-4',8'-anhydro-2',7',9'-trideoxy-D-erythro-α-D-gluco-nonapyranosyl)-5-O-[3-O-(2,6-diamino-2,6-dideoxy-β-L-idopyranosyl)-β-D-ribofuranosyl]-2-deoxystreptamine.5AcOH (109)

Following general procedure A, compound 109 (12.7 mg, 63%) was obtained from D (28.0 mg, 0.023 mmol), as a white foam. [α]$_D^{26}$=+25.7 (c=0.37, H₂O); ESI-HRMS: m/z calculated. for $C_{26}H_{49}N_5O_{14}Na$ [M+Na]⁺ 678.3174, found: 678.3166.

4-O-(2'-Amino-4',8'-anhydro-2',7',9'-trideoxy-D-threo-α-D-gluco-nonapyranosyl)-5-O-[3-O-(2,6-diamino-2,6-dideoxy-β-L-idopyranosyl)-β-D-ribofuranosyl]-2-deoxystreptamine.5AcOH (125)

Following general procedure A, compound 125 (7.0 mg, 40%) was obtained from E (30.0 mg, 0.02 mmol), as a white foam. [α]$_D^{26}$+30.5 (c=0.20, H₂O); ESI-HRMS: m/z calculated. for $C_{26}H_{50}N_5O_{14}$ [M+H]⁺ 656.3354, found: 656.3371.

4-O-(2',6'-Diamino-4',8'-anhydro-2',6',7',9'-tetradeoxy-D-threo-α-D-gluco-nonapyranosyl)-5-O-(β-paramobiosyl)-2-deoxystreptamine.6AcOH (139)

Following general procedure A, compound 139 (6.2 mg, 40%) was obtained from F (22.0 mg, 0.015 mmol), as a white foam. [α]$D^{26}$=+33.8 (c=0.13, H2O); ESI-HRMS: m/z calculated. for $C_{26}H_{51}N_6O_{13}$ [M+H]⁺ 655.3514, found: 655.3505.

4-O-(2',6'-Diamino-4',8'-anhydro-2',6',7',9'-tetradeoxy-D-erythro-α-D-gluco-nonapyranosyl)-5-O-(β-paramobiosyl)-2-deoxystreptamine.6AcOH (150): A solution of G (20.0 mg, 0.014 mmol) in a mixture of 1,4dioxane (0.5 mL), deionized water H2O (0.2 mL), and 0.1 N NaOH (0.1 mL) was treated with Pd/C on carbon (20 mg, 20 wt. %) and stirred for 8 h at room temperature under 40 psi of hydrogen. 10% Aqueous AcOH (0.2 mL) was then added and the mixture was stirred for 20 h at room temperature under 40 psi of hydrogen. After completion, the reaction mixture was filtered through Celite, evaporated under reduced pressure, and the residue was dissolved in AcOH (1 mL) and then charged to a Sephadex column. The Sephadex column was eluted with deionized water H2O (50 mL), 0.5% aqueous NH4OH (40 mL), and 1.5% NH4OH (40 mL) to give 150 (8.5 mg, 60%) as a white form. [α]$D^{26}$=+41.8 (c=0.17, H2O); ESI-HRMS: m/z calculated. for $C_{26}H_{51}N_6O_{13}$ [M+H]⁺ 655.3514, found: 655.3508.

Synthesis of Compound 155:

1,3,2',2''',6'''-Pentaazido-6,3',2'',5'',3''',4'''-hexa-O-benzyl-1,3,2',2''',6'''-pentadeaminoparomomycin-6'-carboxylic Acid (H)

A solution of A¹ (3.60 g, 2.80 mmol) in acetonitrile (16.5 mL) and water (16.5 mL) was stirred with TEMPO (87.5 mg, 0.56 mmol) and iodobenzene diacetate (1.98 g, 6.16 mmol) for 3.5 h at room temperature then concentrated under vacuum and the resulting residue was dissolved EtOAc, and washed with 20% aqueous Na₂S₂O₃, 1N HCl, and brine. The organic layer was dried with Na₂SO₄, filtered, and concentrated. The residue was dissolved in toluene and purified by silica gel column chromatography (eluent: 70% EtOAc and 1% AcOH in hexane) to afford H (3.60 g, 2.77 mmol, 99%) as an orange foam. ESI-HRMS: m/z calc for $C_{69}H_{69}N_{15}O_{15}Na$ [M+Na]⁺1322.4995, found 1322.5044.

1,3,2',2''',6'''-Pentaazido-6,3',2'',5'',3''',4'''-hexa-O-benzyl-1,3,2',2''',6'''-pentadeaminoparomomycin-6'-(N-methoxy-N-methyl)carboxamide (I)

A stirred solution of H (4.64 g, 3.57 mmol), DMAP (91.1 mg, 0.72 mmol), and N,O-dimethylhydroxylamine hydrochloride (0.52 g, 5.4 mmol) in DCM (30 mL) was treated dropwise at room temperature with a solution of DCC (1.11 g, 5.4 mmol) in DCM (5.7 mL). After stirring for 2 h, further DCC (0.37 g, 1.79 mmol) in DCM (1 mL) was added and stirring continued for 2 h before the reaction mixture was concentrated under vacuum. The residue was dissolved in EtOAc and washed with 1N HCl and brine, dried with Na₂SO₄, filtered, and concentrated. The residue was dissolved in toluene and purified by silica gel chromatography (eluent: 40% EtOAc in hexane) to give I (3.22 g, 2.40 mmol, 67%) as a white foam. ESI-HRMS: m/z calc for $C_{67}H_{74}N_{16}O_{15}Na$ [M+Na]⁺1365.5417, found 1365.5453.

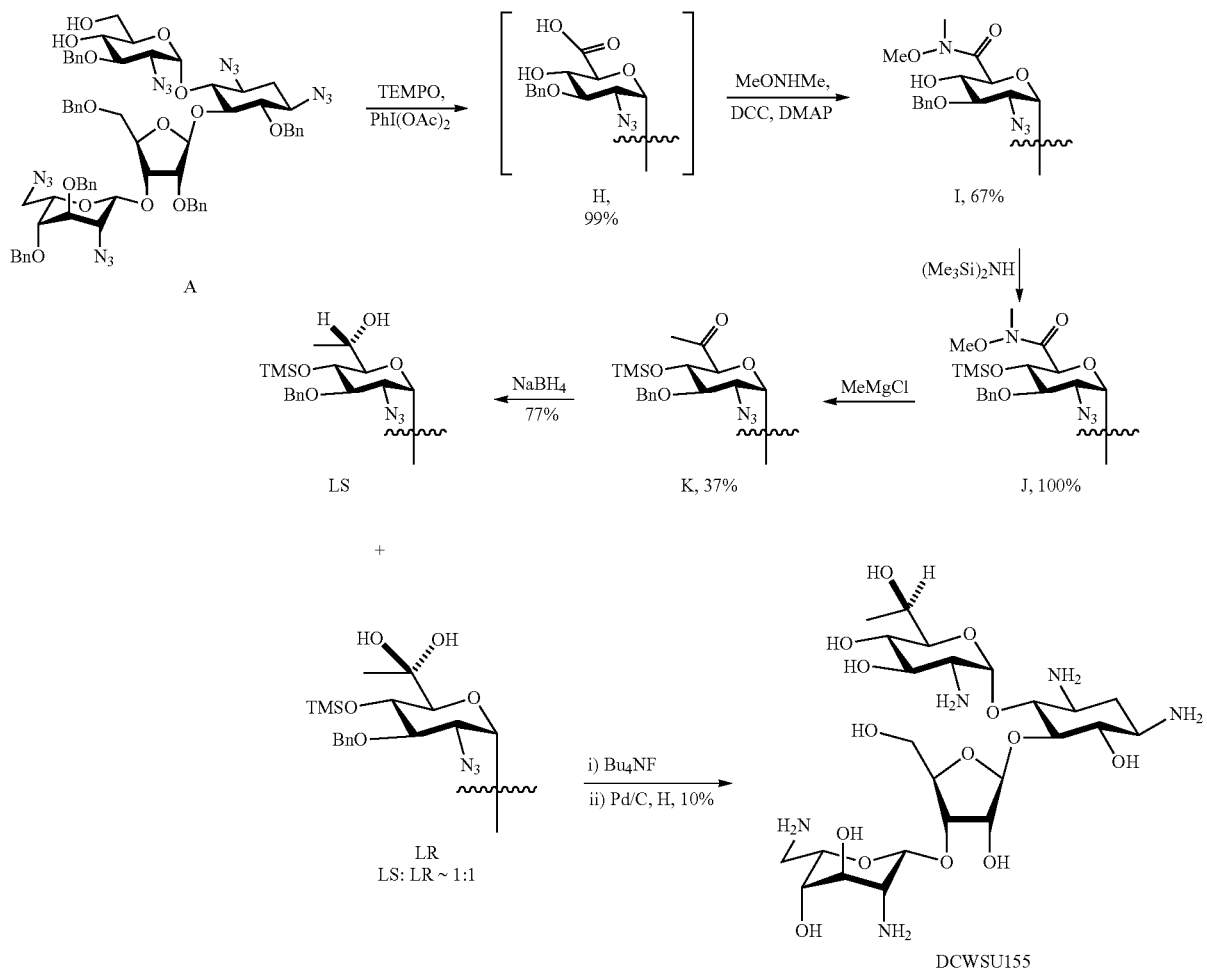

Particular embodiments encompass the compounds H, I, J, K and L (both stereoisomers) of the preceding scheme and their use as an intermediate of an aminoglycoside drug derivative.

1,3,2',2''',6'''-Pentaazido-6,3',2'',5'',3''',4'''-hexa-O-benzyl-4'-O-trimethylsilyl-1,3,2',2''',6'''-pentadeaminoparomomycin-6'-(N-methoxy-N-methyl)carboxamide (J)

A solution of compound I (0.90 g, 0.67 mmol) in MeCN (6.7 mL) was stirred at room temperature with hexamethyldisilamine (0.43 mL, 2.1 mmol) for 3 h, after which concentration to dryness under vacuum gave J as a white foam that was used without further purification. ESI-HRMS: m/z calc for $C_{70}H_{82}N_{16}O_{15}SiNa$ [M+Na]$^+$ 1437.5813, found 1437.5868.

1,3,2',2''',6'''-Pentaazido-6,3',2'',5'',3''',4'''-hexa-O-benzyl-6'-C-methyl-6'-oxo-4'-O-trimethylsilyl-1,3,2',2''',6'''-pentadeaminoparomomycin (K)

A stirred solution of compound J (0.41 g, 0.29 mmol) in THF (2.85 mL) was cooled to −78° C. and treated dropwise with methylmagnesium chloride in THF (3 M, 2.9 mL). After stirring for 5 min the flask was transferred to an ice bath and stirred for another 10 mins, before the reaction mixture was quenched with aqueous NH4Cl (1 mL) and the THF was removed under vacuum. The crude residue was dissolved in Et2O and washed with aqueous NH$_4$Cl and brine. The organic layer was dried with Na$_2$SO$_4$, filtered, and concentrated, and the residue purified by silica gel column chromatography, eluting first with 16% EtOAc in hexanes and then by 20% EtOAc in hexanes, to afford ketone K (0.14 g, 0.10 mmol, 37%) of as a white foam. $C_{69}H_{79}N_{15}O_{14}SiNa$ [M+Na]$^+$ 1392.5598, found 1392.5637.

6'(R)-1,3,2',2''',6'''-Pentaazido-6,3',2'',5'',3''',4'''-hexa-O-benzyl-6'-C-methyl-4'-O-(trimethylsilyl)-1,3,2', 2''',6'''-pentadeaminoparomomycin LR and 6'(S)-1,3,2',2''',6'''-Pentaazido-6,3',2'',5'',3''',4'''-hexa-O-benzyl-6'-C-methyl-4'-O-(trimethylsilyl)-1,3,2',2''', 6'''-pentadeaminoparomomycin LS A solution of K (0.32 g, 0.24 mmol) in THF (1.18 mL) and MeOH (1.18 mL) was stirred with NaBH4 (0.018 g, 0.47 mmol) for 20 mins, then concentrated under vacuum and the residue taken up in EtOAc, and washed with water and brine. The organic layer was dried with Na2SO4, filtered, and concentrated, and purified by silica gel column chromatography, eluting first with 16%, then 18%, and finally 20% EtOAc in hexane to give first the 6'-(S) isomer LS (118 mg, 0.086 mmol, 37%) as a white foam and then the 6'-(R)

isomer LR (123 mg, 0.086 mmol, 37%) also as a white foam with ESIMS $C_{69}H_{81}N_{15}O_{14}SiNa$ $[M+Na]^+$ 1394.5754, found 1394.5784.

6'(R)-6'-C-Methylparomomycin (155)

A 1M solution of TBAF in THF (0.05 mL) was added dropwise at room temperature to a stirred solution of compound LR (26.7 mg, 0.017 mmol) in THF (1.65 mL). After completion the reaction mixture was diluted with $Et_2O$ and washed with aqueous $NaHCO_3$ and brine, dried with $Na_2SO_4$, filtered, and concentrated to give a residue that was taken up in a mixture of dioxane (0.2 mL) and 10% AcOH in water (0.2 mL), treated with Pd/C (58 mg) and stirred under hydrogen (50 psi) for 18 h. The reaction mixture was diluted with water and filtered through Celite and concentrated to dryness. The residue was dissolved in DI water (2 mL), loaded onto a CM Sephadex C-25 column that was eluted with DI water and then with $NH_4OH$ in water starting (0.1% to 0.8%). A few drops of glacial AcOH (10 µL) followed by lyophylization to give 155 penta acetate salt as a white solid (1.8 mg, 10%). ESIMS: $C_{24}H_{47}N_5O_{14}$ $[M+H]^+$ 630.3198, found 630.3212. A general scheme for preparing compound 159 is shown below:

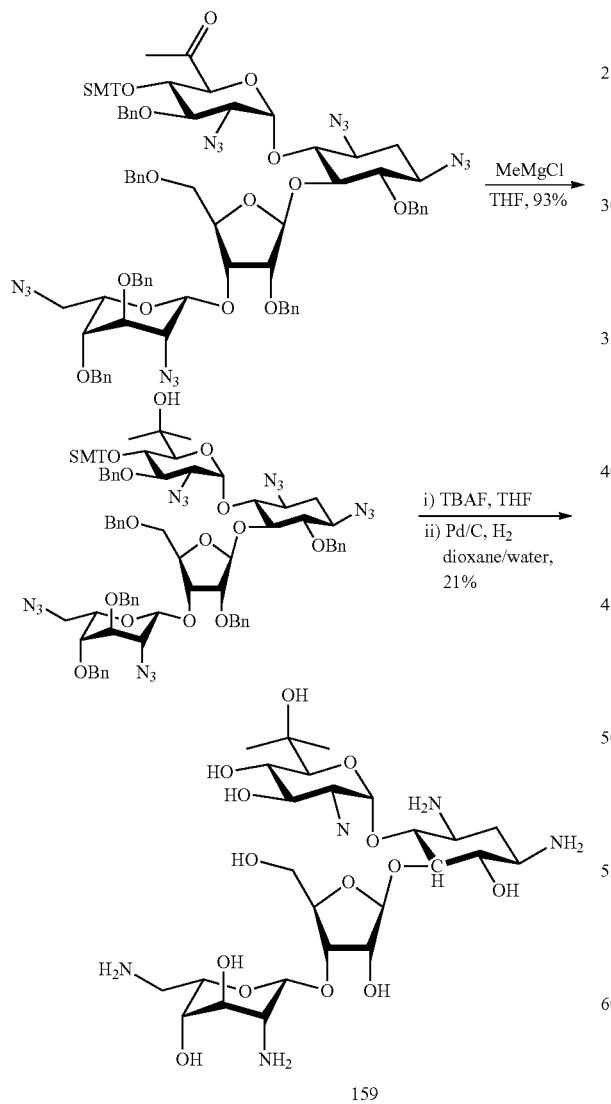

159

6'-Dimethylparomomycin DCWSU159

A general scheme for preparing compound 166 is shown below:

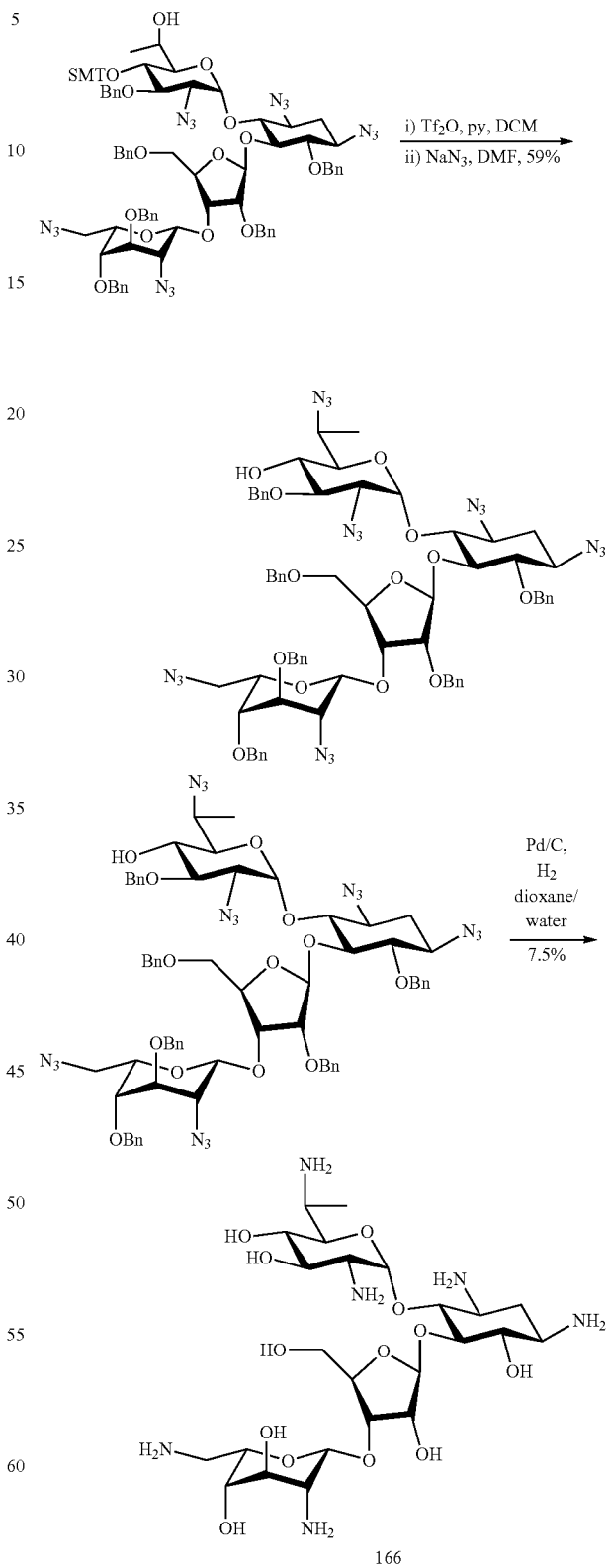

166

6'-C-Methyl neomycin 166

65 66
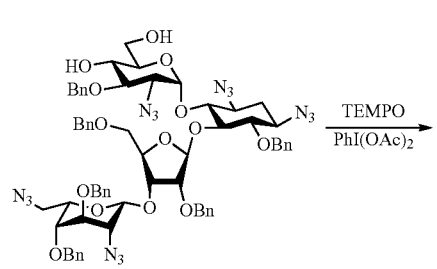 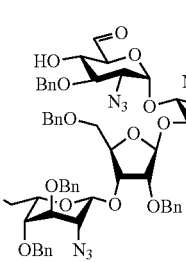 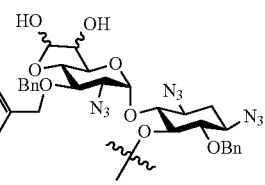
as in expt for IND 17-1396
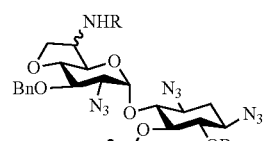 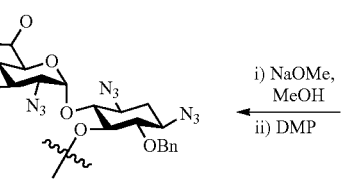
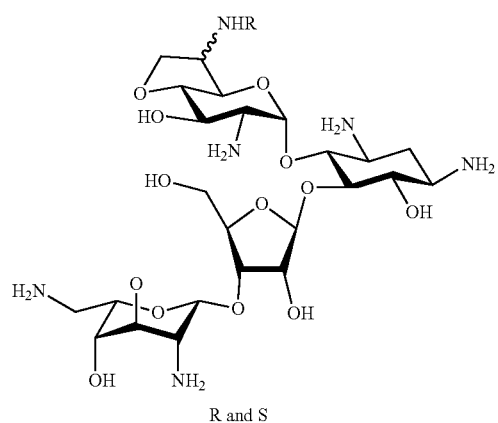
R and S
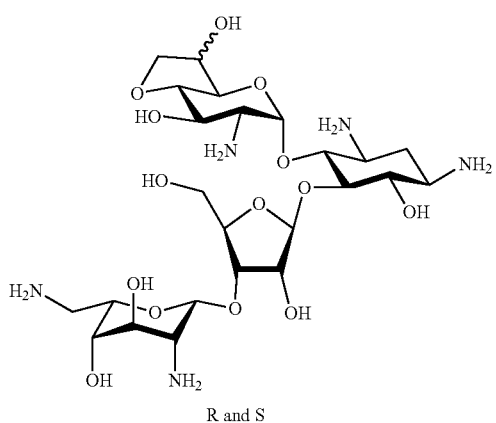
R and S
6,5-Fused Bicyclic Ring I 4,5 Aminoglycoside Analogues
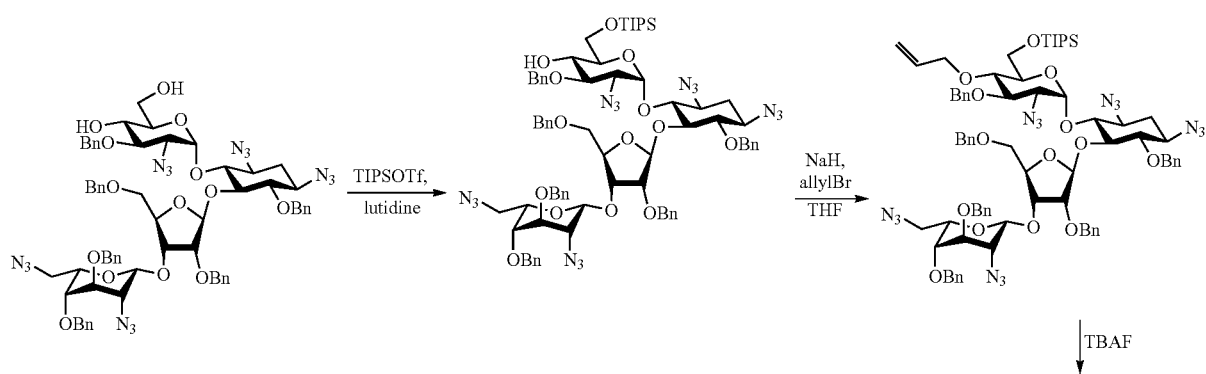

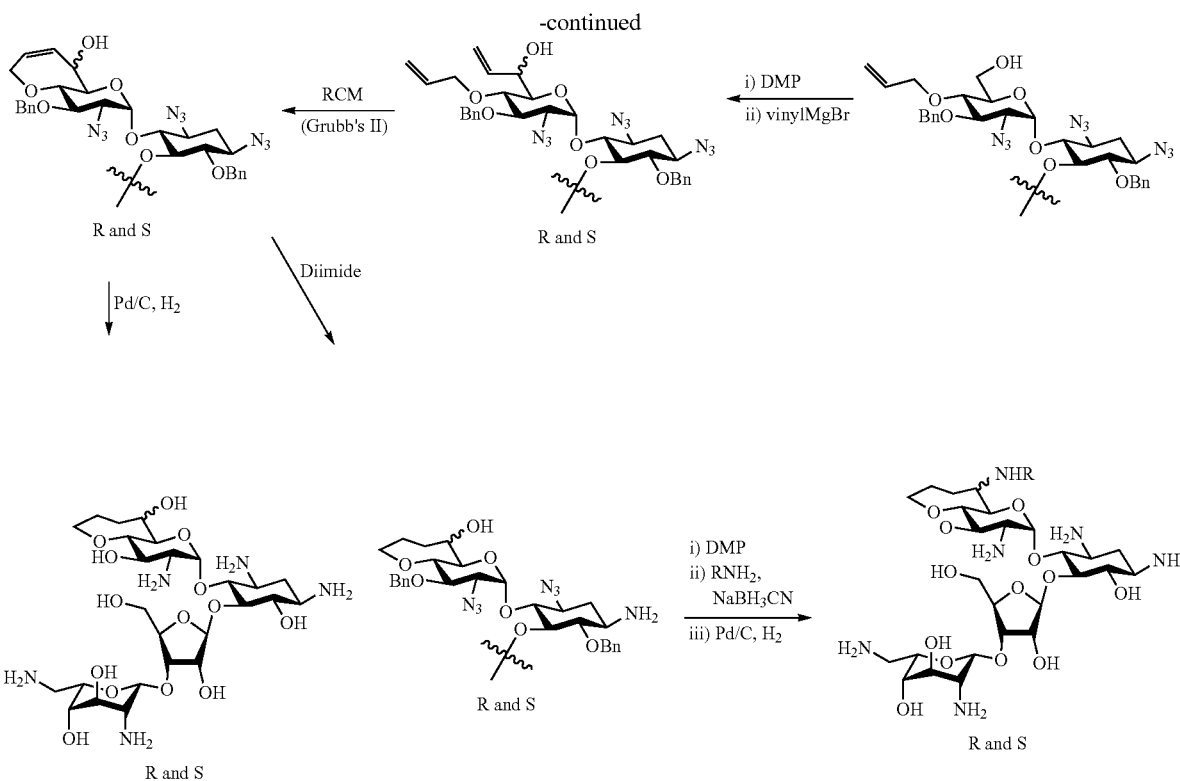
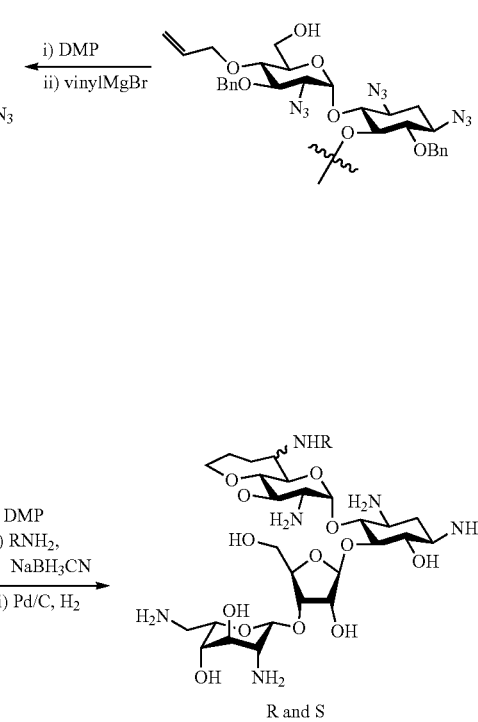
6,7-Fused Bicyclic Ring I Analogues
Synthesis of an Intermediate for Preparation of Five,six-fused derivatives DCWSU203 and DCWSU204, and for that of the six,six-fused derivatives DCWSU210 and DCWSU 211
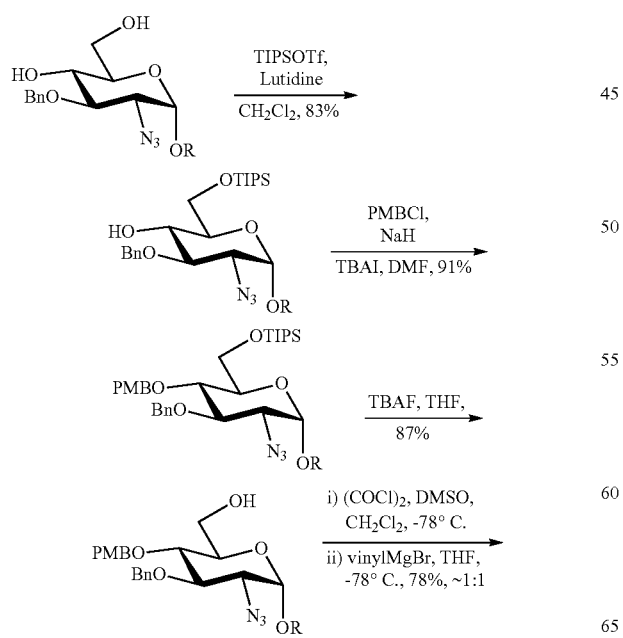

Synthesis of Five,six-fused derivatives DCWSU203 and DCWSU204
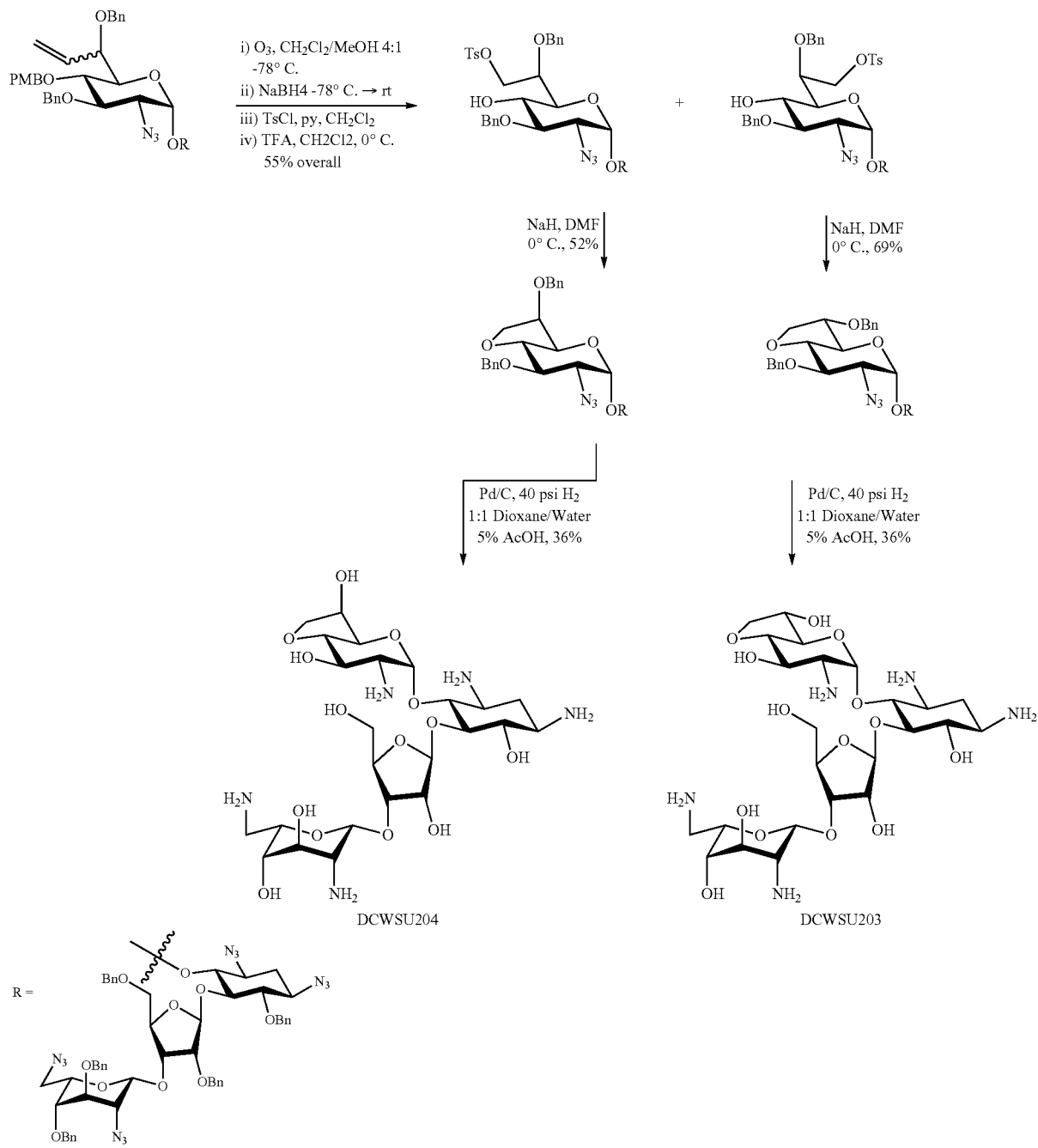
Synthesis of Six,six-fused derivatives DCWSU210 and DCWSU21
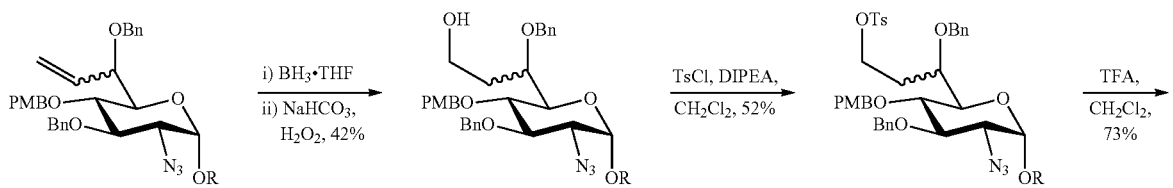

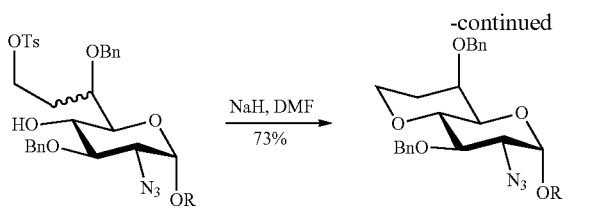
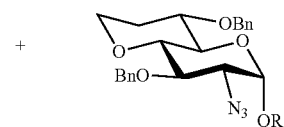
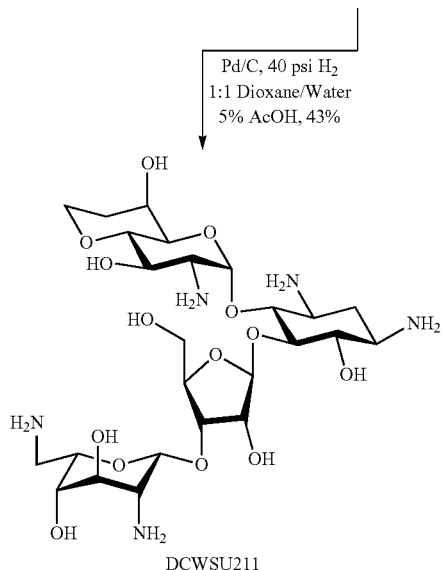
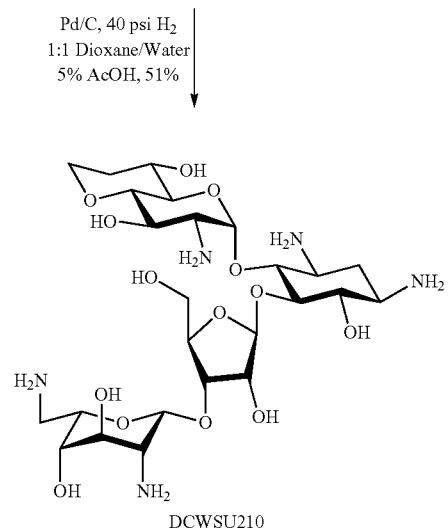
Synthesis of Seven,six-fused derivatives DCWSU196 and DCWSU199
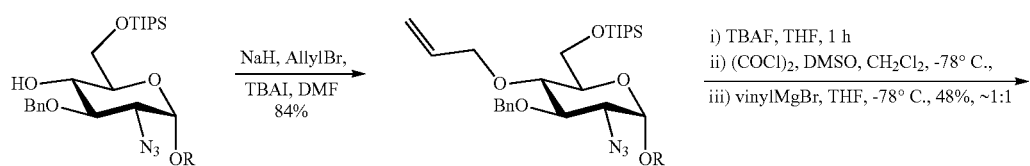
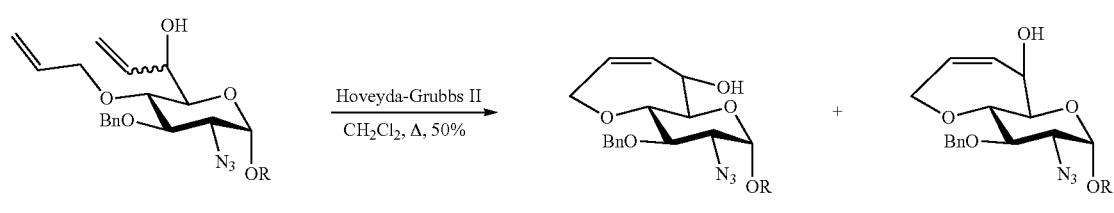

73
74
-continued
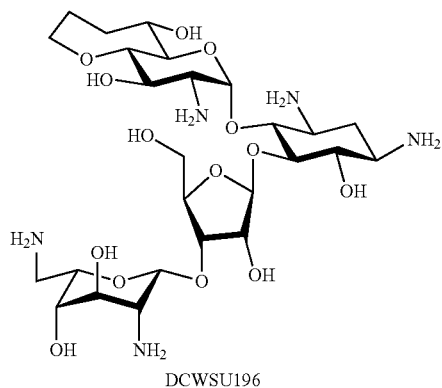
DCWSU196
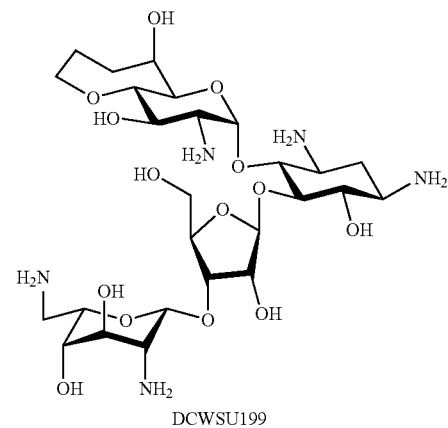
DCWSU199
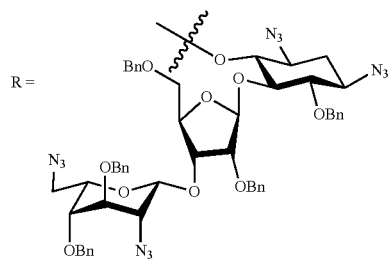
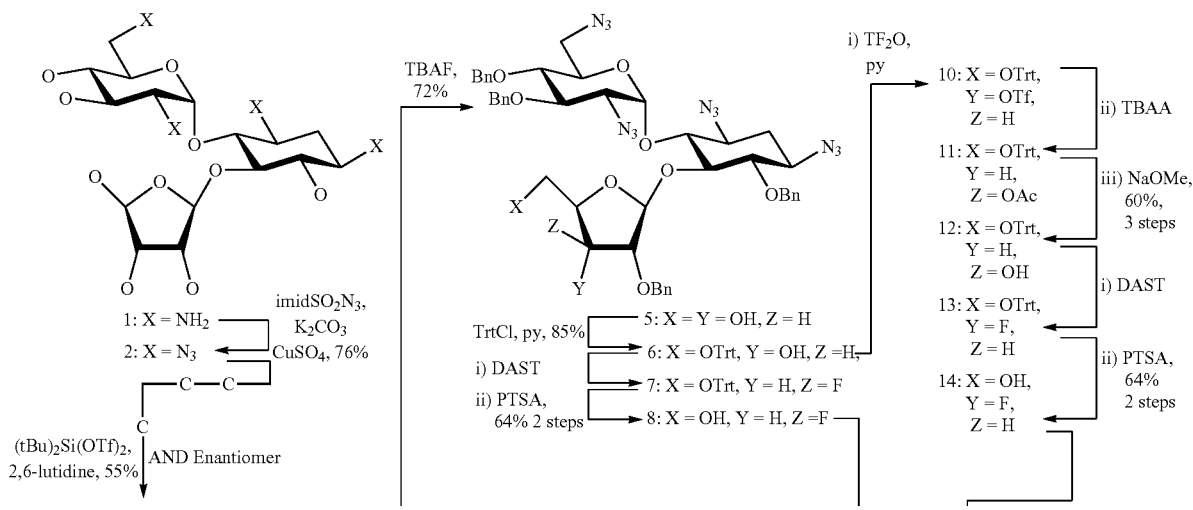

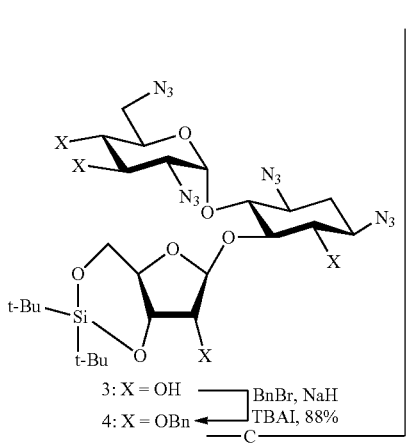
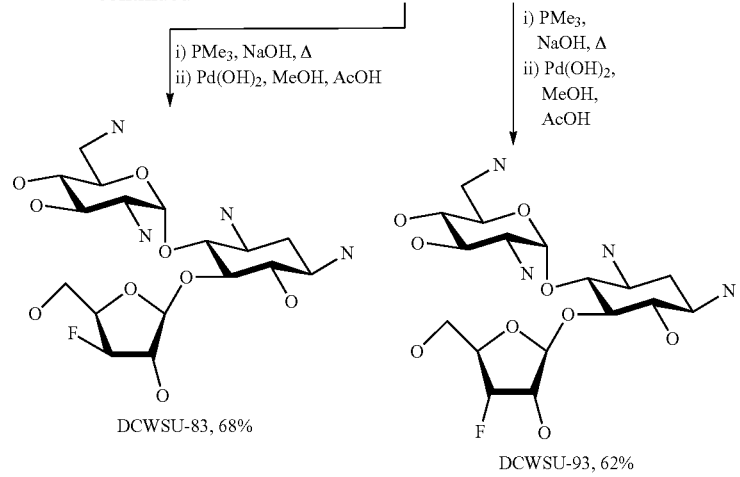

3″-Deoxy-3″-fluoroxylostacin (DCWSU83) and 3″-Deoxy-3″-fluororibostamycin (DCWSU93)

Antimicrobial activity for compounds modified in position A.

The inventors have found that modifications at C4' and C6', forming a novel bicyclic motif in ring 1, result in full protection against AAC(6'), ANT(4'), and partial protection against APH(3') isoforms II and VI. Compounds substituted with an equatorial hydroxyl or amino group are considerably more active than their axial diastereomers. The antibacterial activity of an equatorial hydroxyl group is equivalent to that of the parent, yet displays increased target specificity for bacterial versus human rRNA, a surrogate for increased drug safety.

TABLE 1

(Example 2). Activity Against Wild Type Isolates (MIC$_{50}$ µg/ml)

| Compd | MRSA | | | | E coli | | | P aeruginosa | | | |
|---|---|---|---|---|---|---|---|---|---|---|---|
| | AG38 | AG39 | AG42 | AG44 | AG03 | AG01 | AG55 | AG31 | AG32 | AG33 | AG86 |
| paromomycin | 4 | >256 | >256 | 4-8 | 4 | 2-4 | 2-4 | >128 | >128 | >128 | >128 |
| neomycin | 1-2 | 128 | 128 | 0.5-1 | 1 | 2 | 1-2 | 32 | 32-64 | >128 | >128 |
| 109 | 32 | 32-64 | 16-32 | 32 | 64-128 | 128 | 64-128 | >128 | >128 | >128 | >128 |
| 125 | 8-16 | 8 | 8 | 4 | 8 | 8 | 8 | 32 | 16-32 | >128 | >128 |
| 139 | 4 | 4 | 2 | 2 | 2 | 2 | 2 | 32 | 32 | 128 | 128 |
| 150 | 128 | 128 | 128 | 128 | >128 | >128 | >128 | >128 | >128 | >128 | >128 |
| 142 | 4 | >128 | >128 | 2 | 8 | 8 | 8 | >128 | >128 | >128 | >128 |
| 143 | 32-64 | >64 | >64 | 16 | 32 | 32 | 32 | >64 | >64 | >64 | >64 |
| 155 | 8 | >64 | >64 | 4 | 8-16 | 8-16 | 8-16 | nd | nd | nd | nd |
| 156 | 4-8 | >128 | >128 | 2-4 | 4-8 | 4 | 4 | nd | nd | nd | nd |
| 159 | 8-16 | >128 | >128 | 4-8 | 8 | 8 | 8 | >128 | >128 | >128 | >128 |
| 166 | 2 | >128 | >128 | 1 | 2 | 2 | 2 | ≥128 | 128 | ≥128 | 16 |
| 189 | 4-8 | nd | nd | nd | nd | nd | nd | nd | nd | nd | nd |

TABLE 2A (Example 2). Engineered E coli with specific resistance determinants (MIC$_{50}$ µg/ml)

| compd | BM13 (AG06) wt | AG07 AAC(3) | AG105 AAC(2') | AG09 AAC(6') | AG036 ANT(4',4") | AG037 APH(3',5") | AG103 ArmA |
|---|---|---|---|---|---|---|---|
| paromomycin | 2-4 | 4-8 | 2-4 | 8-16 | 256 | >256 | 4 |
| neomycin | 1 | 4 | 2 | 8 | 32 | >256 | 0.5 |
| 109 | 16-32 | nd | nd | nd | nd | nd | nd |
| 125 | 2 | 8 | 2-4 | 4 | 2-4 | 32-64 | 4 |
| 139 | 1-2 | 4 | 2-4 | 2 | 2 | 32-64 | 2 |
| 150 | 64-128 | nd | nd | nd | nd | nd | nd |
| 142 | 1 | nd | nd | nd | nd | nd | nd |
| 143 | 4 | nd | nd | nd | nd | nd | nd |
| 155 | 2 | nd | nd | nd | nd | nd | nd |

TABLE 2A-continued (Example 2). Engineered E coli with specific resistance determinants (MIC$_{50}$ µg/ml)

| compd | BM13 (AG06) wt | AG07 AAC(3) | AG105 AAC(2') | AG09 AAC(6') | AG036 ANT(4',4") | AG037 APH(3',5") | AG103 ArmA |
|---|---|---|---|---|---|---|---|
| 156 | 1 | nd | nd | nd | nd | nd | nd |
| 159 | 4 | nd | nd | nd | nd | nd | nd |
| 166 | 0.5-1 | nd | nd | 0.5 | 16 | >64 | nd |
| 189 | nd | nd | nd | nd | nd | nd | nd |

TABLE 2B (Example 2). Engineered E coli with specific resistance determinants (MIC$_{50}$ µg/ml)

| | pH430 WT | pH414 AAC(6')-I | pH415 AAC(6')-II | pH421 APH(3')-I | pH422 APH(3')-II | AG037 APH(3')-III | pH423 APH(3)-VI | AG036 ANT(4',4") | pH432 ANT(4') | AG103 armA |
|---|---|---|---|---|---|---|---|---|---|---|
| PAR | 1-2 | 2 | 2-4 | >128 | >128 | >128 | >128 | 32-64 | 1-2 | 2 |
| NEO | 1 | 2 | 4 | >128 | 64 | >64 | 32-64 | 4-8 | 1 | 0.25-0.5 |
| Bicyclic | | | | | | | | | | |
| 125 | 1-2 | 1 | 1-2 | >32 | 4 | 16 | 2 | 0.5 | 1-2 | 1-2 |
| 109 | 16-32 | | | | | | | | | |
| 139 | 0.5-1 | 1 | 1 | >32 | 8 | 8-16 | 1-2 | 0.25 | 1 | 0.5 |
| 150 | 64-128 | | | | | | | | | |
| 6'-mod. | | | | | | | | | | |
| 159 | 1-2 | | | >64 | >64 | >64 | 8 | 16-32 | 2 | 4-8 |
| 142 | 1 | 1 | 1 | >32 | >32 | >32 | >32 | 32-64 | 1 | 1 |
| 156 | 1 | 1 | 1 | >32 | >32 | >32 | >32 | 32-64 | 1 | 1 |
| 155 | 1-2 | 2 | 2 | >32 | >32 | >32 | >32 | >32 | 2 | 8 |
| 143 | 4 | | | >128 | >128 | >128 | 32-64 | 64 | 4 | 16-32 |
| 166 | 0.5 | 0.5 | 1-2 | >32 | >32 | >64 | >32 | 16 | 0.5 | 1 |

TABLE 3

(Example 2)
The following table shows the results of another experiment determining the activity and selectivity of exemplary compounds modified in ring 1:

| | | | | | MIC (µg/mL) | | | | IC50 (µM) | | |
|---|---|---|---|---|---|---|---|---|---|---|---|
| | | | | | AAC | ANT | APH | APH | | | |
| cmpd | 4' | 6' | conf | WT | (6') | (4') | (3')-II | (3')-VI | Bac | Mit | Cyt |
| PAR | OH | OH | lab | 1-2 | 2-4 | 32-64 | >64 | >64 | 0.04 | 140 | 31 |
| 109 | bicyc | OH | ax | 16-32 | | | | | 0.47 | 193 | 169 |
| 125 | bicyc | OH | eq | 1-2 | 1-2 | 0.5 | 4 | 2 | 0.04 | 312 | 30 |
| DC-196 | bicycl. | OH | equatorial | 4 | 4 | 2 | 16 | 16 | | 0.14 | 200 |
| DC-204 | bicycl. | OH | axial | 8 | 16 | 4-8 | 16-32 | 16 | | 0.20 | 131 |
| DC-210 | bicycl. | OH | equatorial | 2-4 | 4 | 2 | 4 | 4-8 | 0.04 | 329 | 50 |
| NEO | OH | NH2 | lab | 1 | 4 | 4-8 | 64 | 32-64 | 0.04 | 4.3 | 35 |
| 150 | bicyc | NH2 | ax | 64-128 | | | | | 0.48 | 4.1 | 12 |
| 139 | bicyc | NH2 | eq | 0.5-1 | 1 | 0.25 | 8 | 1-2 | 0.12 | 2.3 | 19 |

Compd: compound; conf: configuration in 6'; bicyc: bicyclic; ax: axial, eq: equatorial; lab: labile Compounds substituted with an equatorial hydroxyl or amino group are considerably more active than their axial diastereomers. The antibacterial activity of an equatorial hydroxyl group displays increased target specificity for bacterial versus human rRNA, a surrogate for increased drug safety.

Example 3: Compounds Modified in the 2' C of Ring I (Position B)

Synthesis of 2' C modified compounds.
2'-N-Alkyl Paromomycin Derivatives.
For a general synthetic scheme see FIG. 3.

Particular embodiments encompass the compound S of FIG. 3 and its use as an intermediate of an aminoglycoside drug derivative.

1,3,2''',6'''-Tetra-N-acetyl-2'-N-benzyl-2'-N-methyl-paromomycin (S)

To a stirred solution of 1,3,2''',6'''-tetra-N-acetyl-paromomycin R (Cassinell et al. Antibiotics 1978, 31, 378) (500 mg, 0.42 mmol) in methanol (10 mL) was added benzaldehyde (64 µL, 0.63 mmol) at RT. After stirring for 0.5 h at RT glacial acetic acid (48 µL, 1.07 mmol) and sodium cyanoborohydride (68 mg, 1.07 mmol) were added and stirring was continued for 18 h after which 4A-MS (2 g) were added followed by 37% formaldehyde solution (103 μL, 1.26 mmol), glacial acetic acid (48 μL, 1.07 mmol) and sodium cyanoborohydride (68 mg, 1.07 mmol) at RT and stirring was continued for 2 h. The reaction was quenched with aq NaHCO$_3$ (10 mL) at RT. After stirring for 0.5 h the reaction mixture was concentrated to dryness under reduced pressure, dissolved in methanol (50 mL), and the precipitate was filtered off. The filtrate was concentrated under reduced pressure and the residue was purified by column chromatography on silica gel eluting with CHCl3/MeOH/NH4OH (6:3:1) to give S (156 mg, 42%). [α]RTD+36.3 (c 0.27, MeOH). ESIHRMS calculated for C$_{39}$H$_{62}$N$_5$O$_{18}$ [M+H]$^+$, 888.4090; found, 888.4103.

2'-N-Methyl-paromomycin acetate salt (115)

To a stirred suspension of Pd(OH)$_2$/C (70 mg) in MeOH (0.5 mL) was added a solution of S (70 mg, 0.08 mmol) in MeOH (2.0 mL) at RT. The reaction mixture was stirred under a hydrogen atmosphere (1 atm) for 1 h, filtered and concentrated under reduced pressure. The residue was dissolved in 2.5 M NaOH (2 mL) and heated to reflux for 15 h. The reaction mixture was acidified with 10% AcOH and then purified by Sephadex C-25 column chromatography (0.4% NH$_4$OH). The product-containing fractions were concentrated under reduced pressure and the residue was dissolved in 10% AcOH and freeze dried to give 115 in the form of its acetate salt (20 mg, 27%). [α]$^{RT}_D$+39.1 (c 0.67, H$_2$O). ESIHRMS calculated for C$_{24}$H$_{48}$N$_5$O$_{14}$ [M+H]$^+$, 630.3198; found, 630.3180.

1,3,2''',6'''-Tetra-N-acetyl-2'-N-propyl-paromomycin (T)

To a stirred solution of 1,3,2''',6'''-tetra-N-acetyl-paromomycin R$^1$ (150 mg, 0.19 mmol) in methanol (5 mL) was added a 1 M solution of propionaldehyde in DCM (0.3 mL, 0.3 mmol) at RT. After stirring for 0.5 h at RT glacial acetic acid (33 μL, 0.57 mmol) and sodium cyanoborohydride (36 mg, 0.57 mmol) were added to the reaction mixture and stirring was continued for 3 h. The reaction was quenched with aq NaHCO$_3$ (1 mL) at RT. After stirring for 0.5 h the reaction mixture was concentrated to dryness under reduced pressure, and the residue was purified by column chromatography on silica gel eluting with CHCl$_3$/MeOH/NH4OH (6:3:1) to give T (110 mg, 70%). [α]$^{RT}_D$+38.6 (c 0.65, MeOH). ESIHRMS calculated for C$_{34}$H$_{60}$N$_5$O$_{18}$ [M+H]$^+$, 826.3933; found, 826.3929.

2'-N-Propyl-paromomycin acetate salt (128)

Compound T (110 mg, 0.13 mmol) was dissolved in 2.5 M NaOH (2.5 mL) and heated to reflux for 15 h. The reaction mixture was acidified with 10% AcOH and then purified by Sephadex C-25 column chromatography (0.6% NH$_4$OH). The product-containing fractions were concentrated under reduced pressure, and the residue was dissolved in 10% AcOH and freeze dried to give 128 in the form of its acetate salt (63 mg, 49%). [α]$^{RT}_D$+54.3 (c 0.6, H$_2$O). ESIHRMS calculated for C$_{26}$H$_{52}$N$_5$O$_{14}$ [M+H]$^+$, 658.3511; found, 658.3502.

Preparation of 2'-Deamino-2'-Hydroxyparomomycin

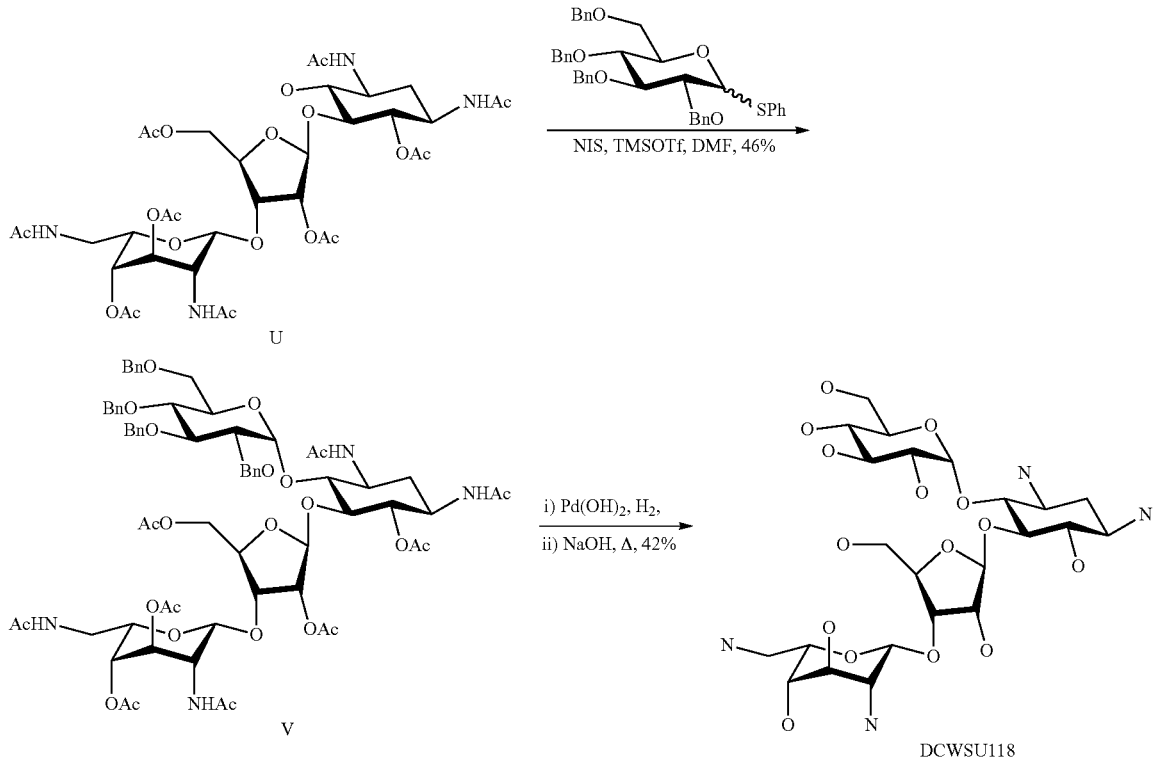

Particular embodiments encompass the compound V of the preceding scheme and its use as an intermediate of an aminoglycoside drug derivative.

1,3,2''',6'''-Tetra-N-acetyl-2'-deamino-2'-benzyloxy-3',4',6'-tri-O-benzyl-6,2'',5'',3''',4'''-penta-O-acetyl-paromomycin (V)

A mixture of phenyl 2,3,4,6-tetra-O-benzyl-D-thioglucopyranoside (Ferrier et al., N. Carbohydr. Res. 1973, 27, 55) (213 mg, 0.24 mmol) and freshly activated molecular sieves (AW300, 600 mg) was suspended in DCM (5 mL). Then DMF (111 µL, 1.44 mmol) was added and the resulting mixture was stirred for 0.25 h at RT before it was cooled to 0° C. and stirred for 0.25 h before NIS (83 mg, 0.36 mmol) and TMSOTf (65 µL, 0.36 mmol) were added. After stirring for additional 0.5 h at 0° C. a solution of U (Cassinelli et al. Antibiotics 1978, 31, 382) (200 mg, 0.24 mmol) in DCM (2.5 mL) was added to the reaction mixture and the reaction mixture was slowly allowed to warm to RT and stirring was continued for 18 h. Then the reaction was quenched with aq $Na_2S_2O_3$ (2 mL) and concentrated to dryness under reduced pressure. The residue was dissolved in MeOH (20 mL), precipitate was filtered off, and the filtrate was concentrated under reduced pressure. The residue was purified by column chromatography on silica gel eluting with $CHCl_3$/MeOH (19:1) to give the desired product 11 (150 mg, 46%). $[\alpha]^{RT}_D$+134.5 (c 0.47, MeOH). ESIHRMS calculated for $C_{69}H_{86}N_4O_{24}Na$ [M+Na]$^+$, 1377.5530; found, 1377.5514.

2'-Deamino-2'-hydroxy-paromomycin acetate salt (118)

To a stirred suspension of Pd(OH)$_2$/C (150 mg) in MeOH (0.5 mL) was added a solution of V (150 mg, 0.11 mmol) in MeOH (3.5 mL) at RT. The reaction mixture was stirred under a hydrogen atmosphere (1 atm) for 4 h, filtered and concentrated under reduced pressure. The residue was dissolved in 2.5 M NaOH (3 mL) and heated to reflux for 8 h. The reaction mixture was acidified with 10% AcOH and then purified by Sephadex C-25 column chromatography (0.6% NH$_4$OH). The product-containing fractions were concentrated under reduced pressure. The residue was dissolved in 10% AcOH and freeze dried to give 118 in the form of its acetate salt (40 mg, 42%). $[\alpha]^{RT}_D$+35.3 (c 0.73, H$_2$O). ESIHRMS calculated for $C_{23}H_{45}N_4O_{15}$ [M+H]$^+$, 617.2881; found, 617.2891.

2'-N-Alkyl Neomycin and 2'-N-Acyl Neomycin Derivatives

For a general synthetic scheme see FIG. 4.

Particular embodiments encompass the compounds AB and AC of FIG. 4 and their use as an intermediate of an aminoglycoside drug derivative.

1,3,6',2''',6'''-Penta-N-acetyl-neomycin (AA)

A stirred solution of neomycin sulfate (10 g, 14.04 mmol) in water (100 mL) was treated with conc aqueous NH$_4$OH (50 mL) then concentrated under vacuum to yield neomycin free base as an off white solid. The solid was taken up in a mixture of water and methanol (3:1, 120 mL) and treated with 1 N HCl (14 mL) at RT before acetic anhydride (150 mL) was added dropwise over a period of 6 h followed by stirring for 24 h. At this stage LCMS analysis of the reaction mixture showed the incomplete reaction consequently the reaction mixture was concentrated under reduced pressure and the residue was re-subjected to the identical sequence of reaction conditions, after which LCMS analysis of the reaction mixture showed penta acetylated neomycin as a major product. Finally, the reaction mixture was concentrated to dryness under reduced pressure and the residue was purified by column chromatography on silica gel eluting with $CHCl_3$/MeOH/NH$_4$OH (5:4:1) to give AA (4.5 g, 39%). $[\alpha]^{RT}_D$+43.9 (c 1.33, MeOH). ESIHRMS calculated for $C_{33}H_{57}N_6O_{18}$ [M+H]$^+$, 825.3729; found, 825.3737.

1,3,6',2''',6'''-Penta-N-acetyl-2'-N-benzyl-2'-N-methyl-6,3',4',2'',5'',3''',4'''-hepta-O-acetyl-neomycin (AB)

To a stirred solution of AA (400 mg, 0.485 mmol) in methanol (8 mL) was added benzaldehyde (74 µL, 0.73 mmol) at RT. After stirring for 0.5 h at RT glacial acetic acid (83 µL, 1.45 mmol) and sodium cyanoborohydride (92 mg, 1.45 mmol) were added and stirring was continued for 5 h after which 4A-MS (1.2 g) were added followed by 37% formaldehyde solution (0.2 mL), glacial acetic acid (83 µL, 1.45 mmol) and sodium cyanoborohydride (92 mg, 1.45 mmol) at RT and stirring was continued for 2 h. The reaction was quenched with aq NaHCO$_3$ (10 mL) at RT. After stirring for 0.5 h the reaction mixture was concentrated to dryness under reduced pressure, dissolved in methanol (50 mL), and the precipitate was filtered off. The filtrate was concentrated under reduced pressure. The residue was dissolved in pyridine (8 mL) and treated with acetic anhydride (8 mL) at RT. The resulting mixture was stirred for 18 h before it was concentrated to dryness under reduced pressure and the residue was purified by column chromatography on silica gel eluting with $CHCl_3$/MeOH (9:1) to give AB (370 mg, 62%). $[\alpha]^{RT}_D$+59.3 (c 1.43, MeOH). ESIHRMS calculated for $C_{55}H_7N_6O_{25}Na$ [M+Na]$^+$, 1245.4914; found, 1245.4906.

2'-N-Methyl-neomycin acetate salt (171)

To a stirred suspension of Pd/C (70 mg) in 10% AcOH (1.5 mL) was added a solution of AB (130 mg, 0.11 mmol) in MeOH (3 mL) at RT. The reaction mixture was stirred under a hydrogen atmosphere (1 atm) for 2 h, filtered and concentrated under reduced pressure. The residue was dissolved in aq Ba(OH)$_2$ (3 mL) and heated to reflux for 72 h. The reaction mixture was acidified with 10% AcOH and then purified by Sephadex C-25 column chromatography (1.2% NH$_4$OH). The product-containing fractions were concentrated under reduced pressure and the residue was dissolved in 10% AcOH and freeze dried to give the desired product 171 in the form of its acetate salt (30 mg, 29%). $[\alpha]^{RT}_D$+41.4 (c 0.29, H$_2$O). ESIHRMS calculated for $C_{24}H_{49}N_6O_{13}$ [M+H], 629.3358; found, 629.3331.

1,3,6',2''',6'''-Penta-N-acetyl-2'-N-ethyl-neomycin (AC)

To a stirred solution of AA (150 mg, 0.18 mmol) in methanol (5 mL) was added a 1M solution of acetaldehyde in DCM (0.3 mL, 0.3 mmol) at RT. After stirring for 0.5 h at RT glacial acetic acid (31 µL, 0.55 mmol) and sodium cyanoborohydride (34 mg, 0.55 mmol) were added to the reaction mixture and stirring was continued for 2 h. The reaction was quenched with aq NaHCO$_3$ (1 mL) at RT. After stirring for 0.5 h the reaction mixture was concentrated to dryness under reduced pressure and the residue was purified by column chromatography on silica gel eluting with $CHCl_3$/MeOH/$NH_4OH$ (6:3:1) to give AC (90 mg, 58%). $[\alpha]^{RT}_D$+58.1 (c 0.94, MeOH). ESIHRMS calculated for $C_{35}H_{61}N_6O_{18}$ $[M+H]^+$, 853.4042; found, 853.4028.

2'-N-Ethyl-neomycin acetate salt (172)

Compound AC (75 mg, 0.09 mmol) was dissolved in aq $Ba(OH)_2$ (2 mL) and heated to reflux for 24 h. The reaction mixture was acidified with 10% AcOH and then purified by Sephadex C-25 column chromatography (0.8% $NH_4OH$). The product-containing fractions were concentrated under reduced pressure and the residue was dissolved in 10% —AcOH and freeze dried to give 172 in the form of its acetate salt (22 mg, 25%). $[\alpha]^{RT}_D$+32.3 (c 0.7, $H_2O$). ESIHRMS calculated for $C_{25}H_{51}N_6O_{13}$ $[M+H]^+$, 643.3514; found, 643.3512.

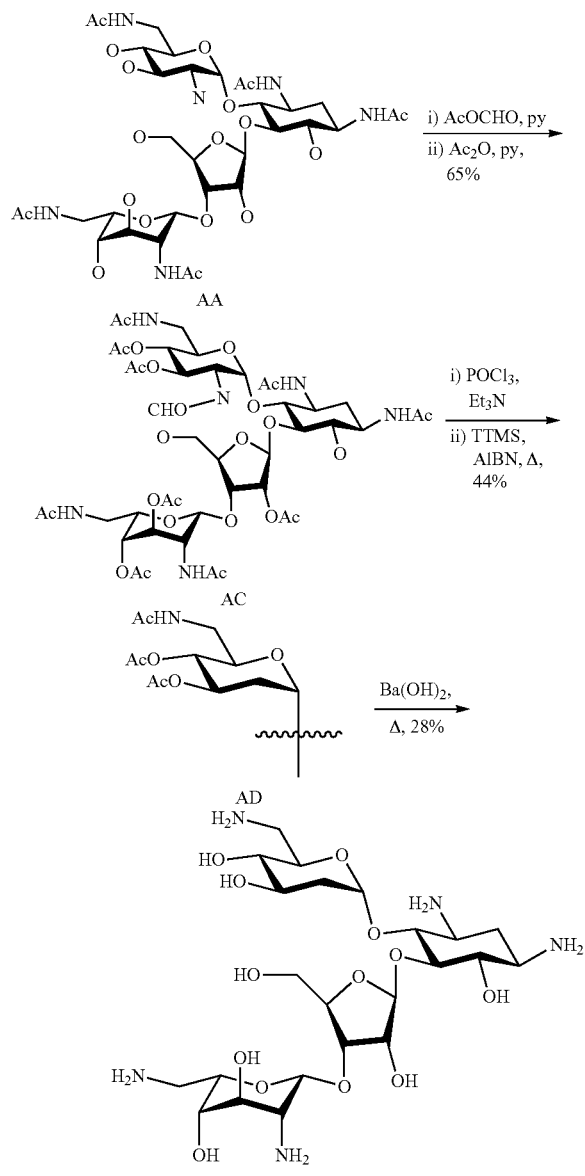

1,3,6',2''',6'''-Penta-N-acetyl-2'-N-formyl-6,3',4',2'', 5'',3''',4'''-hepta-O-acetyl-neomycin (AC)

A stirred solution of AA (500 mg, 0.61 mmol) in DMF (10 mL) was treated with pyridine (0.15 mL) at RT and cooled to 0° C. before acetic formic anhydride (72 µL, 0.91 mmol) was added. The reaction mixture was stirred for 4 h at 0° C. before it was quenched with excess of MeOH (10 mL). Then the reaction mixture was concentrated to dryness under reduced pressure and the residue was dissolved in pyridine (5 mL) and treated with acetic anhydride (5 mL) at RT. The resulting mixture was stirred for 18 h before it was concentrated to dryness under reduced pressure and the residue was purified by column chromatography on silica gel eluting with $CHCl_3$/MeOH (9:1) to give AC (450 mg, 65%). $[\alpha]^{RT}_D$+37.6 (c 1.33, MeOH). ESIHRMS calculated for $C_{43}H_{70}N_6O_{26}Na$ $[M+Na]^+$, 1169.4237; found, 1169.4248.

2'-Deamino-neomycin acetate salt (173)

A stirred solution of AC (400 mg, 0.35 mmol) in DCM (8 mL) was treated with $Et_3N$ (2 mL) at RT before $POCl_3$ was added dropwise. The reaction mixture was stirred for 4 h at RT before it was quenched with aq $NaHCO_3$ (5 mL). Then it was concentrated to dryness under reduced pressure and the residue was dissolved in acetone (50 mL). The precipitate was filtered off and the filtrate was concentrated under reduced pressure. The residue was dissolved in a mixture of toluene and MeCN (2:1, 16 mL) and the solution was degassed by sparging with argon before tris(trimethylsilyl) silane (1 mL, 3.5 mmol) was added at RT. Then the reaction temperature was raised to 90° C. and to this heated solution was added a solution of AIBN (12 mg, 0.07 mmol) in MeCN (1 mL) dropwise. The resulting mixture was stirred for 2 h at 90° C. before it was concentrated to dryness under reduced pressure and the residue was purified by column chromatography on silica gel eluting with $CHCl_3$/MeOH (9:1) to give crude AD (170 mg, 44%) that was used for next reaction without further purification and characterization. Compound AD (100 mg, 0.09 mmol) was dissolved in aq $Ba(OH)_2$ (2 mL) and heated to reflux for 24 h. The reaction mixture was acidified with 10% AcOH and then purified by Sephadex C-25 column chromatography (0.8% —$NH_4OH$). The product-containing fractions were concentrated under reduced pressure and the residue was dissolved in 10% AcOH and freeze dried to give 173 in the form of its acetate salt (22 mg, 28%). $[\alpha]^{RT}_D$+23.2 (c 0.43, $H_2O$). ESIHRMS calculated for $C_{23}H_{46}N_5O_{13}$ $[M+H]^+$, 600.3092; found, 600.3076.

For a general synthetic scheme see FIG. 5.

Particular embodiments encompass the compounds AE, AF, AG and AH of FIG. 5 and their use as an intermediate of an aminoglycoside drug derivative.

1,3,6',2''',6'''-Penta-N-acetyl-1,3,6',2''',6'''-penta-N-tert-butoxycarbonyl-2'-azido-6,3',4',2'',5'',3''',4'''-hepta-O-acetyl-2'-deamino-neomycin (AE)

A stirred solution of neomycin sulfate (10 g, 14.04 mmol) in water (100 mL) was treated with conc aqueous $NH_4OH$ (50 mL) then concentrated under vacuum to yield neomycin free base as an off white solid. This solid was taken up in a mixture of water and methanol (3:1, 120 mL) and treated with 1 N HCl (14 mL) at RT before acetic anhydride (150 mL) was added dropwise over a period of 6 h and stirring was continued for additional 24 h. At this stage LCMS analysis of the reaction mixture showed incomplete reaction, consequently the reaction mixture was concentrated under reduced pressure and the residue was re-subjected to the same sequence of reaction conditions after which LCMS analysis of the reaction mixture showed penta-acetyl neomycin as a major product. The reaction mixture was concentrated to dryness under reduced pressure and the residue was dissolved in MeOH (200 mL), the precipitate was filtered off and the filtrate was concentrated under reduced pressure. The residue was dissolved in a mixture methanol and water (2:3, 120 mL), treated with potassium carbonate (5.8 g, 42.1 mmol) at RT and cooled to 0° C. before imidazole-1-sulfonyl azide hydrochloride (4.4 g, 21.0 mmol) and copper (II) sulfate (224 mg, 1.4 mmol) were added. The reaction mixture was allowed to warm to RT and stirring was continued for 18 h after which it was concentrated to dryness under reduced pressure, dissolved in methanol (200 mL), the precipitate was filtered off and the filtrate concentrated under reduced pressure. The residue was dissolved in THF (100 mL) and (Boc)$_2$O (45.9 g, 210.6 mmol) and DMAP (8.6 g, 70.2 mmol) were added followed by heating to reflux for 48 h. The reaction mixture was concentrated to dryness under reduced pressure and the residue was dissolved in pyridine (50 mL) and treated with acetic anhydride (50 mL) at RT. The resulting mixture was stirred for 18 h before it was concentrated to dryness under reduced pressure. The residue was dissolved in ethyl acetate (500 mL) and washed with water (2×250 mL) and brine (2×250 mL). The organic layer was dried over Na$_2$SO$_4$, concentrated under reduced pressure, and the residue was purified by column chromatography on silica gel eluting with ethyl acetate/hexane (1:1) to give AE (3 g, 13%). $[\alpha]^{RT}_D$+56.2 (c 0.4, MeOH). ESIHRMS calculated for C$_{72}$H$_{108}$N$_8$O$_{35}$Na [M+Na]$^+$, 1667.6815; found, 1667.6802.

1,3,6',2''',6'''-Penta-N-tert-butoxycarbonyl-neomycin (AF)

To a stirred solution of AE (1.1 g, 0.67 mmol) in MeOH (11 mL) was added NaOMe (867 mg, 16.1 mmol) at RT. After stirring for 3 h the reaction mixture was neutralized with Amberlyst (H-form), filtered, and concentrated under reduced pressure. Then the residue was dissolved in a mixture of THF and water (2:1, 15 mL) and trimethylphosphine (1M in THF, 1.3 mL) was added at RT. After stirring for 3 h at 60° C. the reaction mixture was concentrated to dryness under reduced pressure and the residue was purified by column chromatography on silica gel eluting with CHCl$_3$/MeOH (7:1) to give AF (400 mg, 53%). $[\alpha]^{RT}_D$+30.0 (c 0.48, MeOH). ESIHRMS calculated for C$_{48}$H$_{87}$N$_6$O$_{23}$ [M+H]$^+$, 1115.5823; found, 1115.5814.

1,3,6',2''',6'''-Penta-N-tert-butoxycarbonyl-2'-N-(2-azidoacetyl)-neomycin (AG)

To a stirred solution of AF (150 mg, 0.13 mmol) and 2-azidoacetic acid (27 mg, 0.27 mmol) in THF (1.5 mL) was added EDC.HCl (51 mg, 0.27 mmol), HOBt (36 mg, 0.27 mmol), and DIPEA (116 μL, 0.67 mmol) at RT. After stirring for 2 h at RT the reaction mixture was quenched with aq HCl (30 mL) and extracted with DCM (3×30 mL). The combined DCM layer was dried over Na$_2$SO$_4$ and concentrated under reduced pressure and the residue was purified by column chromatography on silica gel eluting with CHCl$_3$/MeOH (9:1) to give AG (110 mg, 68%). $[\alpha]^{RT}_D$+32.3 (c 1.16, MeOH). ESIHRMS calculated for C$_{50}$H$_{87}$N$_9$O$_{24}$Na [M+Na]$^+$, 1220.5762; found, 1220.5723.

2'-N-(2-Aminoacetyl)-neomycin acetate salt (175)

To a stirred suspension of Pd(OH)$_2$/C (50 mg) in 10% AcOH (1 mL) was added a solution of AG (100 mg, 0.08 mmol) in dioxane (2 mL) at RT. The reaction mixture was stirred under a hydrogen atmosphere (1 atm) for 2 h, filtered and concentrated under reduced pressure. The residue was dissolved in a mixture of TFA/Water/Anisole (90:7:3, 2 mL) and stirred for 1 h at RT before it was concentrated to dryness under reduced pressure. The residue was purified by Sephadex C-25 column chromatography (0.8% NH$_4$OH). The product-containing fractions were concentrated under reduced pressure and the residue was dissolved in 10% AcOH and freeze dried to give the desired product 175 in the form of its acetate salt (40 mg, 47%). $[\alpha]^{RT}_D$+34.7 (c 0.96, H$_2$O). ESIHRMS calculated for C$_{25}$H$_{50}$N$_7$O$_{14}$ [M+H]$^+$, 672.3416; found, 672.3400.

1,3,6',2''',6'''-Penta-(t-butyloxycarbonyl)-2'-N-formamido-neomycin (AH)

To a cooled solution of AF (75 mg, 67.3 μmol) in CH$_2$Cl$_2$ (2 mL) and pyridie (54 μL, 673.0 μmol), acetic formic anhydride (16 μL, 101 μmol) was added dropwise. The reaction mixture was stirred in ice bath for 1 h. The reaction mixture was diluted with methanol (3 mL), and saturated solution of NaHCO$_3$ and stirred at RT. After 1 h, the reaction mixture was diluted with ethyl acetate and washed with brine. The organic layer was dried on Na$_2$SO$_4$, concentrated and purified by column chromatography on silica gel (16:1 ethyl acetate/methanol) to give AH as a white solid (60 mg, 78%). ESIHRMS calculated for C$_{49}$H$_{86}$N$_6$O$_{24}$ [M+Na]$^+$, 1165.5591; found, 1165.5598. $[\alpha]^{21}_D$+30.97 (c 1.75, MeOH).

2'-N-Formamido-neomycin (182)

Compound AH (50 mg, 77.8 μmol) was treated with a solution of trifluoroacetic acid:anisole:water (4 mL, 100:3:7) at RT for 45 min. After stirring for 45 min, the reaction mixture was concentrated to dryness under reduced pressure and the residue was purified by Sephadex C-25 column chromatography (0.5% ammonium hydroxide). The product was dissolved in 10% aq. AcOH and freeze dried and to give 182 as the penta-acetate salt (18 mg, 44%). ESIHRMS calculated for C$_{25}$H$_{48}$N$_6$O$_{14}$ [M+Na]$^+$, 679.3126; found, 679.3156. $[\alpha]^{21}_D$+30.3 (c 0.75, H$_2$O). In the $^1$H-NMR spectrum the formamide is a mixture of two rotamers in the ratio of 1:0.4. Biological testing of 2' C modified compounds (position B).

Modifications at C2' result in enhanced potency against Mycobacteria, as well as full protection against acquired AAC(2') antimicrobial resistance in gram-negatives. Furthermore, various modifications at the 2' position are demonstrated to retain the full antibacterial potency of the parent compound while increasing target specificity for bacterial versus human rRNA, a surrogate for increased drug safety.

The following tables show results from different experiments aimed at determining activity and selectivity, where applicable, of the exemplary compounds:

TABLE 1

(Example 3). Selected MICs (μg/ml) against clinical isolates
(Institute of Medical Microbiology, Zurich)

| Compound | MRSA | | | | E coli | | |
|---|---|---|---|---|---|---|---|
| | AG038 | AG039 | AG042 | AG044 | AG001 | AG055 | AG003 |
| Paromomycin | 4 | >256 | >256 | 4-8 | 16-32 | 8 | 8-16 |
| 2'-NHMe (115) | 8 | >128 | >128 | 4 | 16 | 16 | 16 |
| 2'-NHEt (127) | 8 | >128 | >128 | 4-8 | 16 | 16 | 16 |
| 2'-NHPr (128) | 8-16 | >128 | >128 | 4 | 16 | 16 | 16 |
| Neomycin B | 0.25 | 128 | 128 | 0.5-1 | 4 | 1 | 1 |
| 2'-H (173) | 1 | 32 | 32 | nd | 2 | 2 | 1-2 |
| 2'-OH (119) | 2 | >128 | >128 | 2 | 2-4 | 2-4 | 2-4 |
| 2'-NHMe (171) | 0.25-0.5 | >32 | >32 | nd | 1 | 1 | 1 |
| 2'-NHEt (172) | 0.5 | >32 | >32 | nd | 1-2 | 1 | 1 |
| 2'-NHCHO (182) | 2-4 | >32 | >32 | nd | 4-8 | 2 | 4-8 |
| 2'-NHAc (183) | >32 | >32 | >32 | nd | >32 | >32 | >32 |
| 2'-NHCOCH$_2$NH$_2$ (175) | 4 | >32 | >32 | nd | 16 | 16 | 32 |

TABLE 2

(Example 3). Selected MICs (μg/ml) against wild type and
resistant strains of E coli carrying the AAC(2') resistance determinant

| Strain | AG006 | AG104 | AG106 |
|---|---|---|---|
| Resistance Mechanism | Wild type | Wild type | AAC(2') |
| Paromomycin | 2 | 2 | >64s |
| 2'-NHMe (115) | nd | 2-4 | 4-8 |
| Neomycin B | 0.25-0.5 | 0.5-1 | 8 |
| 2'-H (173) | 1 | 0.5-1 | 1 |
| 2'-OH (119) | 0.5 | 1 | 1 |
| 2'-NHMe (171) | 0.25 | 0.5 | 0.5 |
| 2'-NHEt (172) | 0.5 | 0.5 | 0.5 |
| 2'-NHCHO (182) | 2 | 2-4 | 2 |
| 2'-NHAc (183) | 64 | 128 | 128 |
| 2'-NHCOCH$_2$NH$_2$ (175) | 8 | 16 | 16-32 |

TABLE 3

(Example 3) Selectivity for Binding to the Bacterial
Ribosome over the Mitochondrial, Mutant
Mitochondrial, and Cytosolic Ribosomes

| Compound | Mitochondrial | Mutant Mitochondrial | Cytosolic |
|---|---|---|---|
| Paromomycin | 2506 | 267 | 471 |
| 2'-NHMe (115) | 3151 | 1134 | 1264 |
| 2'-NHEt (127) | 4715 | 1804 | 918 |
| 2'-NHPr (128) | 3066 | 763 | 425 |
| Neomycin B | 123 | 9.1 | 1045 |
| 2'-H (173) | 831 | 31 | 3188 |
| 2'-OH (119) | 1222 | 94 | 3667 |
| 2'-NHMe (171) | 483 | 117 | 4000 |
| 2'-NHEt (172) | 850 | 111 | 3111 |
| 2'-NHCHO (182) | 463 | 108 | 1093 |
| 2'-NHAc (183) | 18 | 5.2 | 28 |
| 2'-NHCOCH$_2$NH$_2$ (175) | 67 | 153 | 155 |

TABLE 4

(Example 3)

| | | | MIC (μg/mL) | | | | | | |
|---|---|---|---|---|---|---|---|---|---|
| | | | E. coli | | | M. abscessus | | IC50 (μM) | |
| | | | | AAC(2') | AAC(2') | | Clin. | | | |
| cmpd | 6' | 2' | WT | AG106 | pH434 | ATCC | Isol. | Bac | Mit | Cyt |
| PAR | OH | NH2 | 1-2 | >64 | >64 | 8 | 32 | 0.04 | 140 | 31 |
| 115 | OH | N-met | 2-4 | 4 | 8 | 16 | 32 | 0.03 | 95 | 38 |
| 127 | OH | N-et | 2 | 2 | 4 | 32 | 64 | 0.03 | 141 | 28 |
| 128 | OH | N-prop | 2 | 2 | 4 | 32 | 64 | 0.05 | 153 | 21 |
| NEO | NH2 | NH2 | 1 | 8 | >64 | 16 | 16 | 0.04 | 4.3 | 35 |
| 173 | NH2 | H | 1 | 1 | 8 | 4 | 8 | 0.03 | 22 | 85 |
| 119 | NH2 | OH | 0.5-1 | 1 | 4 | 2 | 4 | 0.03 | 36 | 108 |
| 171 | NH2 | N-met | 0.5 | 0.5 | 4 | 0.25 | 0.5 | 0.01 | 4.7 | 37 |
| 172 | NH2 | N-et | 0.5-1 | 0.5 | 1 | 0.25 | 0.5 | 0.01 | 11 | 43 |
| 182 | NH2 | N-formyl | 2 | 2 | 8-16 | 16 | 32 | 0.12 | 54 | 127 |

Modifications at C2' result in enhanced potency against Mycobacteria, as well as full protection against acquired AAC(2') antimicrobial resistance in gram-negatives. Furthermore, various modifications at the 2' position are demonstrated to retain the full antibacterial potency of the parent compound while increasing target specificity for bacterial versus human rRNA, a surrogate for increased drug safety.

TABLE 5

(Example 3) antibacterial activity of 2'-modified compounds against E. coli strains with acquired AAC(2') resistance and Mycobacteria with intrinsic AAC(2') resistance (MIC in µg/ml)

|  | E. coli WT | E. coli AG106 AAC(2')-Ia | E. coli pH434 AAC(2')-Ib | E. coli pGB2armA armA | M. smegmatis SZ380 WT | M. abscessus ATCC 19977 WT | M. abscessus engineered Δeis2 | M. abscessus clinical isolate |
|---|---|---|---|---|---|---|---|---|
| PAR | 1-2 | >64 | >64 | 2 | 1 | 8 | 4 | 32 |
| 118 | 32 |  |  |  | >128 |  |  |  |
| 115 | 2-4 | 4 | 8 | 4-8 | 4-8 | 16 | 0.5 | 32 |
| 127 | 2 |  | 4 | 4-8 | 4 | 32 | 0.5 | 64 |
| 128 | 2 |  | 4 | 4-8 | 2 | 32 | 1 | 64 |
| NEO | 0.5-1 | 8 | >64 | 0.25-0.5 | 0.5 | 16 | 4 | 16 |
| 173 | 1 | 1 | 8 | 1 | 0.25 | 4 | 0.125 | 8 |
| 119 | 0.5-1 | 1 | 4 | 1 | 0.5 | 2 | 0.125 | 4 |
| 171 | 0.5 | 0.5 | 4 | 1 | <0.063 | 0.25 | 0.063 | 0.5 |
| 172 | 0.5-1 | 0.5 | 1 | 1 | <0.063 | 0.25 | 0.063 | 0.5 |
| 182 | 2 | 2 | 8-16 | 8 | 1 | 16 | 0.5 | 32 |
| 175 | 8-16 | 16-32 |  | 16 | 0.25 |  |  |  |
| 183 | 128 | 128 |  | 128-256 | 8 |  |  |  |
| RIB | 2 | 128 | >128 | 2 | 8 | 128 | 32 | 128 |
| 034 | 128 |  |  |  | >256 |  |  |  |
| 062 | 64-128 |  |  |  | >128 |  |  |  |
| 064 | >128 |  |  |  | >128 |  |  |  |
| 100 | 8 |  | >128 | 32 | 32-64 | 32 | 8 | 64 |
| 037 | 16-32 |  | 32 | 64-128 | 64 | 128 | 32 | >128 |
| GEN | 0.5 | 2-4 |  | >128 | 1 | 2-4 | 2 |  |
| PLZ | 0.5-1 | 8-16 | 8 | >128 | 0.25 | 1 | 1 | 4 |
| AMK | 2 | 2 | 2 | >128 | 0.5 | 1 | 0.125-0.25 | 2 |

PAR, paromomycin; NEO, neomycin B; RIB, ribostamycin; GEN, gentamicin, for comparison only; PLZ, plazomicin, for comparison only Example 4

Further experiments to characterize exemplary compounds have rendered the following data:

TABLE 1

(Example 4)

|  | MIC (µg/mL) | | | | | | Disk diffusion |
|---|---|---|---|---|---|---|---|
|  | AG212 E. coli | AG215 K. pneumon | AG220 P. aerugin | AG225 A. baumannii | AG290 E. cloacae | SZ380 M. smegmatis | 25 nmol N. gonorrhoeae |
| PAR | 2-4 | 1 | >64 | 2 | 2 | 1 | 9 mm |
| LIV | 4 | 2 | 4 | 4 | 2 | 0.5 | — |
| NEO | 0.5-1 | 0.5 | 32 | 1-2 | 1 | 0.5 | <8 mm |
| RIB | 4 | 2 | >128 | 4 | 4 | 8 | — |
| Bicyclic | | | | | | | |
| 125 | 2 | 2 | 8 | 4 | 2 | 0.5 | 9 mm |
| 109 | — | — | — | — | — | 16 | — |
| 139 | 1 | 0.5-1 | 16-32 | 4 | 1 | 1-2 | — |
| 150 | — | — | — | — | — | 16-32 | — |
| 196 | 4 | 2 | >32 | 4 | 2-4 |  |  |
| 199 | >32 | 32 | >32 | >32 | >32 |  |  |
| 203 | 32 |  |  |  |  |  |  |
| 204 | 16 |  |  |  |  |  |  |
| 210 | 4 |  |  |  |  |  |  |
| 211 | 32-64 |  |  |  |  |  |  |

TABLE 1-continued (Example 4)

| | MIC (µg/mL) | | | | | | Disk diffusion |
|---|---|---|---|---|---|---|---|
| | AG212 E. coli | AG215 K. pneumon | AG220 P. aerugin | AG225 A. baumannii | AG290 E. cloacae | SZ380 M. smegmatis | 25 nmol N. gonorrhoeae |
| 6'-modif. | | | | | | | |
| 159 | 4 | 1-2 | >64 | 4 | 2 | 2 | — |
| 142 | 2 | 1 | >32 | 2 | 1 | 0.5 | — |
| 156 | 2 | 1 | >32 | 2 | 1 | 0.5 | 10 mm |
| 155 | 4 | 2 | >32 | 4 | 2-4 | 4 | 8 mm |
| 143 | 8 | 4 | >128 | 4-8 | 4-8 | 16 | — |
| 166 | 1 | 0.25-0.5 | >32 | 1 | 0.5 | 0.125-0.25 | 12 mm |
| 189 | 8 | 2 | >64 | 4-8 | 2-4 | — | — |
| 192 | 4 | 2 | >64 | 8 | 2-4 | | |
| 2'-modif. | | | | | | | |
| 115 | 4 | 2 | >64 | 4 | 2 | 4-8 | — |
| 127 | 4 | 2 | >64 | 4 | 2-4 | 4 | 9 mm |
| 128 | 4 | 2 | >64 | 4 | 2 | 2 | 11 mm |
| 173 | 1 | 0.5 | >64 | 1 | 1 | 0.25 | 10 mm |
| 119 | 1 | 0.5 | >64 | 1 | 1 | 0.5 | — |
| 171 | 1 | 0.5 | >64 | 1 | 0.5-1 | <0.0625 | 9 mm |
| 172 | 1 | 0.5 | >32 | 1 | 0.5-1 | <0.0625 | 9 mm |
| 182 | 4 | 1-2 | >64 | 2 | 2 | 1 | — |
| 175 | 16 | 8 | >32 | 8-16 | — | 0.25 | — |
| 183 | >32 | >32 | >32 | >32 | | 8 | — |
| 100 | 32 | 16 | >128 | 64 | 32 | 32-64 | — |
| 37 | 64 | 64 | >128 | >64 | 64-128 | 64 | — |
| 5"-modif. | | | | | | | |
| 137 | 2 | 1 | >64 | 2 | 1-2 | 1 | 11 mm |
| 141 | 4 | 2 | >64 | 4 | 2-4 | 2 | — |
| 165 | 16 | 8 | >64 | 8-16 | 8 | 32 | — |
| 153 | 4 | 1-2 | 8 | 4 | 2 | 1 | 13 mm |
| 4'-modif. | | | | | | | |
| 073 | 8 | 4 | >128 | 8 | 4 | 8 | |
| 079 | 1 | 0.5 | 4 | 1-2 | 0.5 | 0.5 | 16 mm |
| 116 | 2 | 1 | 4 | 2 | 1 | 1 | |
| 187 | 2 | 0.5 | 2-4 | 2 | 0.5-1 | | 11 mm |
| 190 | 16 | 32 | >64 | >64 | 16-32 | | |
| 193 | 4 | 2 | >64 | 32 | 2 | | |
| 194 | 2 | 0.5 | 8-16 | 2 | 1 | | |
| 195 | 8 | 2-4 | 64 | 8 | 4 | | |
| 197 | 2-4 | 1 | 32 | 2 | 1-2 | | |
| 198 | 8 | 2-4 | 16 | 8 | 4 | | |
| 206 | 8 | | | | | | |
| 3"-modif. | | | | | | | |
| 042 | 1 | 0.5 | >32 | 1-2 | 1-2 | 2-4 | |
| 043 | 2 | 1 | >64 | 2 | 1 | 4 | |
| 083 | 2 | 1 | >64 | 16 | 2 | 16-32 | |
| 093 | 2 | 1-2 | >64 | 16 | 2 | 8. | |

ATCC25922; AG215, *Klebsiella pneumonia*; AG220, *Pseudomonas aeruginosa* ATCC27853; AG225, *Acinetobacter baumannii pittii*; AG290, *Enterobacter cloacae*; SZ380, *Mycobacterium smegmatis*.

TABLE 2

(Example 4) Antibacterial activity of 3', 4', and 5"-modified compounds against *E. coli* strains with defined resistance determinants (MIC in µg/ml)

| | Engineered strains | | | | | Clinical isolates | | |
|---|---|---|---|---|---|---|---|---|
| | pH430 E. coli WT | pH421 E. coli APH(3')-I | pH422 E. coli APH(3')-II | AG037 E. coli APH(3')-III | pH423 E. coli APH(3')-VI | AG160 E. coli WT | AG163 E. coli APH(3')-I | AG166 E. coli APH(3')-II |
| PAR | 1-2 | >128 | >128 | >128 | >128 | 2-4 | >128 | >128 |
| LIV | 2 | >64 | 2 | >128 | 2 | 4 | >128 | 4-8 |
| 137 | 1-2 | >64 | >64 | 128 | >64 | 2 | 64 | >128 |

TABLE 2-continued (Example 4) Antibacterial activity of 3', 4', and 5''-modified compounds against *E. coli* strains with defined resistance determinants (MIC in μg/ml)

|     | Engineered strains | | | | | Clinical isolates | | |
| --- | --- | --- | --- | --- | --- | --- | --- | --- |
|  | pH430 *E. coli* WT | pH421 *E. coli* APH(3')-I | pH422 *E. coli* APH(3')-II | AG037 *E. coli* APH(3')-III | pH423 *E. coli* APH(3')-VI | AG160 *E. coli* WT | AG163 *E. coli* APH(3')-I | AG166 *E. coli* APH(3')-II |
| 141 | 2-4 | >64 | >64 | >128 | >64 | 4 | | |
| 165 | 8-16 | >64 | >64 | >64 | >64 | 8 | | |
| 153 | 2 | 2 | 4 | 2 | 2-4 | 2-4 | 4-8 | 8-16 |
| 079 | 0.5 | >32 | 4 | >64 | 1 | 1 | >64 | 1-2 |
| 116 | 0.5 | >32 | 0.5 | >64 | 1 | 1 | >64 | 2-4 |
| 187 | 0.5-1 | 4-8 | 0.5-1 | 8 | 1 | 2 | 2 | 2 |
| 194 | 1 | 64-128 | 2 | 2 | 2 | 2 | 4-8 | 2-4 |
| NEO | 1 | >128 | 64 | >64 | 32-64 | 1 | >64 | 64 |
| 140 | 1 | >32 | 1 | 32 | 1 | 1 | 64 | 1 |
| RIB | 2 | >128 | 128-256 | 32-64 | >128 | 4 | >128 | >128 |
| 129 | 32 | | | >64 | | 64 | | |
| 130 | 4 | >64 | >64 | >128 | >64 | 16 | >128 | >128 |

PAR, paromomycin LIV, lividomycin B; NEO, neomycin B; RIB, ribostamycin

TABLE 3

(Example 4) Antibacterial activity against clinical isolates (MIC in μg/ml)

|  | AG001 *E. coli* WT | AG055 *E. coli* WT | AG003 *E. coli* AAC(3)-II | AG038 MRSA | AG044 MRSA | AG039 MRSA AAC(6')-I ANT(4')-I | AG042 MRSA AAC(6')-I ANT(4')-I APH(2') | AG031 *P. aer.* APH(3')-II | AG032 *P. aer.* APH(3')-II |
| --- | --- | --- | --- | --- | --- | --- | --- | --- | --- |
| PAR | 2 | 2 | 2-4 | 4 | 4-8 | >256 | >256 | >128 | >128 |
| LIV | 4 | 2 | 4 | 4 | 4-8 | >128 | >128 | 16 | >128 |
| NEO | 1 | 1 | 1 | 0.25 | | 128 | 128 | 8 | 8 |
| RIB | 4 | 2 | 4 | 4 | 8 | >128 | >128 | >128 | >128 |
| Bicyclic | | | | | | | | | |
| DC125 | 8 | 8 | 8 | 8-16 | 4 | 8 | 8 | 32 | 16-32 |
| DC109 | 128-256 | 64-128 | 64-128 | 32 | 32 | 32-64 | 16-32 | >128 | >128 |
| DC139 | 2 | 2 | 2 | 4 | | 4 | 2 | 32 | 32 |
| DC150 | >128 | >128 | >128 | 128 | 128 | 128 | 128 | >128 | >128 |
| DC196 | 4 | | | 2 | | | | >32 | |
| DC199 | >32 | | | 32 | | | | >32 | |
| DC203 | 32 | | | 16-32 | | | | | |
| DC204 | 16 | | | 8 | | | | | |
| DC210 | 4 | | | 4 | | | | 64 | |
| DC211 | 64 | | | 32 | | | | >64 | |
| 6'-mod. | | | | | | | | | |
| DC159 | 8 | 8 | 8 | 8-16 | 4-8 | >128 | >128 | >128 | >128 |
| DC142 | 8 | 8 | 8 | 4 | 2 | >128 | >128 | >128 | >128 |
| DC156 | 4-8 | 4 | 4 | 4-8 | 2-4 | >128 | >128 | >32 | >32 |
| DC155 | 8-16 | 8-16 | 8-16 | 8 | 4 | >64 | >64 | >32 | >32 |
| DC143 | 32 | 32 | 32 | 32-64 | 16 | >64 | >64 | >64 | >64 |
| DC166 | 2 | 2 | 2 | 2 | 1 | >128 | >128 | 128-256 | 128 |
| DC189 | 8-16 | 8 | 8 | 4-8 | | >32 | >32 | >32 | >32 |
| DC192 | 8 | | | 4 | | | | >64 | |
| 2'-modif. | | | | | | | | | |
| DC118 | >128 | >128 | >128 | 64-128 | 64-128 | >128 | >128 | >128 | >128 |
| DC115 | 16 | 16 | 16 | 8 | 4 | >128 | >128 | >128 | >128 |
| DC127 | 16 | 16 | 16 | 8 | 4-8 | >128 | >128 | >128 | >128 |
| DC128 | 16 | 16 | 16 | 8-16 | 4 | >128 | >128 | >128 | >128 |
| DC-173 | 2 | 2 | 1-2 | 1 | 2 | 32 | 32-64 | 32 | 64 |
| DC-119 | 2-4 | 2-4 | 2-4 | 2 | 2 | >128 | >128 | 128 | 128 |
| DC-171 | 1 | 1 | 1 | 0.5 | 0.5 | >32 | >32 | 64 | 64 |
| DC-172 | 1-2 | 1 | 1 | 0.5 | 1 | >32 | >32 | >64 | >64 |
| DC-182 | 4-8 | 2 | 4-8 | 2-4 | | >32 | >32 | >32 | >32 |
| DC-175 | 16 | 16 | 32 | 4 | | >32 | >32 | >32 | >32 |
| DC-183 | >32 | >32 | >32 | >32 | | >32 | >32 | >32 | >32 |
| DC-034 | | | | 256-512 | >256 | | | | |
| DC-062 | >128 | | >128 | >128 | >128 | | >128 | >128 | |

TABLE 3-continued (Example 4) Antibacterial activity against clinical isolates (MIC in μg/ml)

| | AG001 E. coli WT | AG055 E. coli WT | AG003 E. coli AAC(3)-II | AG038 MRSA | AG044 MRSA | AG039 MRSA AAC(6')-I ANT(4')-I | AG042 MRSA AAC(6')-I ANT(4')-I APH(2') | AG031 P. aer. APH(3')-II | AG032 P. aer. APH(3')-II |
|---|---|---|---|---|---|---|---|---|---|
| DC-064 | >128 | | >128 | >128 | >128 | >128 | >128 | | |
| DC-100 | 64-128 | 64-128 | 64 | 64-128 | 128 | >128 | >128 | >128 | >128 |
| DC-037 5"-modif. | 128 | | 128 | >128 | >128 | | >128 | | |
| DC047 | 8-16 | 8-16 | 8 | 8 | 8-16 | >128 | >128 | 4 | 4 |
| DC048 | 32-64 | 32 | 16 | 8 | 8-16 | >64 | >128 | | |
| DC137 | 4 | 2-4 | 2-4 | 4 | 2-4 | >128 | >128 | ≥128 | 128 |
| DC141 | 8 | 4 | 4 | 4-8 | 4 | >128 | >128 | >128 | >128 |
| DC165 | 16 | 16 | 16 | 16-32 | 16 | >128 | >128 | >128 | >128 |
| DC153 | 4 | 2-4 | 4 | 4 | 4 | >128 | >128 | 32-64 | 32 |
| DC129 | >64 | >64 | >64 | >128 | >128 | >128 | >128 | >128 | >128 |
| DC130 4'-modif. | 32 | 32 | 32 | 64 | 128 | >128 | >128 | >128 | >128 |
| DC094 | 8 | 8-16 | 8 | 4 | 16 | >128 | >128 | >128 | >128 |
| DC073 | 16-32 | 16-32 | 16-32 | 32 | 32-64 | 32-64 | 64 | | |
| DC079 | 4 | 4 | 2-4 | 2 | 2 | 2 | 2 | 8 | 8 |
| DC116 | 4-8 | 4-8 | 4-8 | 2 | 1 | 2 | 2 | 32 | 32 |
| DC187 | 2 | 2 | 1 | 1-2 | | 1 | 2 | 8-16 | 8 |
| DC190 | 32 | | | 16 | | | | >64 | |
| DC193 | 4 | | | 4 | | | | >64 | |
| DC194 | 2-4 | | | 1-2 | | | | 16-32 | |
| DC195 | 8 | | | 4 | | | | | |
| DC197 | 2-4 | | | 1 | | | | 16 | |
| DC198 | 16 | | | 4 | | | | 32 | |
| DC206 | 8 | | | 8 | | | | 64-128 | |

PAR, paromomycin; LIV, lividomycin B; NEO, neomycin B; RIB, ribostamycin; MRSA, methicillin resistant *Staphylococcus aureus*; *P. aer.*, *Pseudomonas aeruginosa*

TABLE 4

(Example 4). Inhibition of ribosomal in-vitro translation and relative target specificity bacterial vs. human drug targets

| | IC50 (μM) | | | | | Target specificity bacterial vs. | |
|---|---|---|---|---|---|---|---|
| | Bacterial | Mitoch. | Cytosolic | Rabbit | Mitoch. A1555G | Mitochondrial | Cytosolic |
| PAR | 0.04 | 140 | 31 | 21 | 15 | +++++ | ++ |
| LIV | 0.04 | 109 | 53 | 25 | 25 | +++++ | ++++ |
| NEO | 0.04 | 4.3 | 35 | 49 | 0.4 | low | +++ |
| RIB | 0.09 | 443 | 484 | 172 | 68 | +++++ | +++++ |
| Bicyclic | | | | | | | |
| DC125 | 0.04 | 312 | 30 | 56 | 18 | +++++ | ++ |
| DC109 | 0.47 | 193 | 169 | 54 | | (+) | (+) |
| DC139 | 0.12 | 2.3 | 19 | 41 | 0.3 | low | low |
| DC150 | 0.48 | 4.1 | 12 | 13 | 2.3 | low | low |
| DC196 | 0.14 | 200 | 88 | 43 | 96 | ++++ | ++ |
| DC199 | 2.0 | 554 | 557 | 229 | 602 | low | low |
| DC203 | 0.09 | 170 | 38 | | 6 | ++++ | + |
| DC204 | 0.20 | 131 | 276 | | 117 | ++ | ++++ |
| DC210 | 0.04 | 329 | 50 | | 44 | +++++ | ++++ |
| DC211 6'-modif. | 1.2 | 51 | 58 | | 121 | low | low |
| DC159 | 0.04 | 211 | 30 | 15 | 87 | +++++ | ++ |
| DC142 | 0.04 | 107 | 34 | 12 | 20 | +++++ | +++ |
| DC156 | 0.02 | 185 | 2.6 | 5.4 | 8.4 | +++++ | low |
| DC155 | 0.04 | 118 | 44 | 18 | 88 | +++++ | +++ |
| DC143 | 0.16 | 328 | 259 | 66 | 93 | +++++ | ++++ |
| DC166 | 0.01 | 9.0 | 26 | 48 | 1 | +++ | +++++ |
| DC189 | 0.19 | 841 | 482 | 78 | 220 | +++++ | +++++ |
| DC192 | 0.11 | 359 | 236 | 78 | 169 | +++++ | +++++ |

TABLE 4-continued (Example 4). Inhibition of ribosomal in-vitro translation and relative target specificity bacterial vs. human drug targets

| | IC50 (μM) | | | | | Target specificity bacterial vs. | |
|---|---|---|---|---|---|---|---|
| | Bacterial | Mitoch. | Cytosolic | Rabbit | Mitoch. A1555G | Mitochondrial | Cytosolic |
| 2'-modif. | | | | | | | |
| DC118 | 1.36 | 408 | 275 | 98 | 193 | (+) | low |
| DC115 | 0.03 | 95 | 38 | 19 | 34 | +++++ | ++++ |
| DC127 | 0.03 | 141 | 28 | 15 | 54 | +++++ | +++ |
| DC128 | 0.05 | 153 | 21 | 6 | 38 | +++++ | + |
| DC-173 | 0.03 | 22 | 85 | 74 | 0.9 | ++ | +++++ |
| DC-119 | 0.03 | 36 | 108 | 88 | 2.7 | ++++ | +++++ |
| DC-171 | 0.01 | 4.7 | 37 | 38 | 1.1 | + | +++++ |
| DC-172 | 0.01 | 11 | 43 | 45 | 1.6 | +++ | +++++ |
| DC-182 | 0.12 | 54 | 127 | 110 | 13 | + | +++ |
| DC-175 | 0.16 | 11 | 25 | 48 | 1.2 | low | low |
| DC-183 | 5.3 | 93 | 147 | 103 | 28 | low | low |
| DC-034 | 4.4 | >500 | >500 | >500 | >500 | | |
| DC-062 | 1.2 | >500 | >500 | >500 | >500 | | |
| DC-064 | >10 | 149 | 154 | 68 | 176 | low | low |
| DC-100 | 0.52 | 457 | 372 | 90 | 224 | +++ | ++ |
| DC-037 | 0.93 | >500 | >500 | >500 | >500 | | |
| 5''-modif. | | | | | | | |
| DC047 | 0.10 | 325 | 293 | 157 | 119 | +++++ | +++++ |
| DC048 | 0.09 | 76 | 50 | 50 | 34 | ++ | ++ |
| DC137 | 0.04 | 144 | 90 | 29 | 30 | +++++ | +++++ |
| DC141 | 0.03 | 70 | 89 | 29 | 28 | +++++ | +++++ |
| DC165 | 0.30 | 195 | 39 | 22 | 13 | ++ | low |
| DC153 | 0.12 | 144 | 132 | 57 | 39 | ++++ | +++ |
| DC129 | 1.2 | 298 | 307 | 169 | 376 | low | low |
| DC130 | 0.24 | 364 | 359 | 152 | 190 | ++++ | ++++ |
| 4'-modif. | | | | | | | |
| DC079 | 0.03 | 160 | 69 | 36 | 46 | +++++ | +++++ |
| DC116 | 0.06 | 70 | 94 | 40 | 30 | ++++ | ++++ |
| DC187 | 0.08 | 155 | 44 | 34 | 34 | +++++ | + |
| DC190 | 0.78 | 1056 | 630 | 197 | 449 | ++++ | ++ |
| DC193 | 0.42 | 91 | 64 | 48 | 59 | low | low |
| DC194 | 0.04 | 275 | 102 | 45 | 48 | +++++ | +++++ |
| DC195 | 0.32 | 981 | 917 | 1302 | 759 | +++++ | +++++ |
| DC197 | 0.05 | 48 | 79 | 31 | 39 | +++ | ++++ |
| DC198 | 0.15 | 48 | 88 | 50 | 49 | (+) | ++ |
| DC206 | 0.10 | 290 | 178 | | 206 | +++++ | ++++ |

PAR, paromomycin; LIV, lividomycin B; NEO, neomycin B; RIB, ribostamycin; Bacterial, *Mycobacterium smegmatis* ribosomes; Mitochondrial/Cytosolic, ribosomes with a human mitochondrial/cytosolic decoding site, respectively [Ref]; Rabbit, mammalian cytosolic ribosomes with a decoding site identical to human cytosolic ribosomes; A1555G, human mitochondrial decoding site with a single point mutation causing hypersusceptibility to aminoglycoside antibiotics.

TABLE 5

(Example 4) Antibacterial activity of bicyclic and 6'-modified compounds against *E. coli* strains with defined resistance determinants (MIC in μg/ml)

| | pH430 WT | pH414 AAC(6')-I | pH415 AAC(6')-II | pH421 APH(3')-I | pH422 APH(3')-II | AG037 APH(3')-III | pH423 APH(3')-VI | AG036 ANT(4',4'') | pH432 ANT(4') | AG103 armA |
|---|---|---|---|---|---|---|---|---|---|---|
| PAR | 1-2 | 2 | 2-4 | >128 | >128 | >128 | >128 | 32-64 | 1-2 | 2 |
| NEO | 1 | 2 | 4 | >128 | 64 | >64 | 32-64 | 4-8 | 1 | 0.25-0.5 |
| Bicyclic | | | | | | | | | | |
| DC125 | 1-2 | 1 | 1-2 | >32 | 4 | 16 | 2 | 0.5 | 1-2 | 1-2 |
| DC109 | 16-32 | | | | | | | | | |
| DC139 | 0.5-1 | 1 | 1 | >32 | 8 | 8-16 | 1-2 | 0.25 | 1 | 0.5 |
| DC150 | 64-128 | | | | | | | | | |
| DC196 | 4 | | | >128 | 64 | >128 | 16 | 2 | | |
| DC210 | 2-4 | | | >128 | 32 | >128 | 4 | 2 | | |

TABLE 5-continued (Example 4) Antibacterial activity of bicyclic and 6'-modified compounds against *E. coli* strains with defined resistance determinants (MIC in μg/ml)

| | pH430 WT | pH414 AAC(6')-I | pH415 AAC(6')-II | pH421 APH(3')-I | pH422 APH(3')-II | AG037 APH(3')-III | pH423 APH(3')-VI | AG036 ANT(4',4") | pH432 ANT(4') | AG103 armA |
|---|---|---|---|---|---|---|---|---|---|---|
| 6'-modif. | | | | | | | | | | |
| DC159 | 1-2 | | | >64 | >64 | >64 | 8 | 16-32 | 2 | 4-8 |
| DC142 | 1 | 1 | 1 | >32 | >32 | >32 | >32 | 32-64 | 1 | 1 |
| DC156 | 1 | 1 | 1 | >32 | >32 | >32 | >32 | 32-64 | 1 | 1 |
| DC155 | 1-2 | 2 | 2 | >32 | >32 | >32 | >32 | >32 | 2 | 8 |
| DC143 | 4 | | | >128 | >128 | >128 | 32-64 | 64 | 4 | 16-32 |
| DC166 | 0.5 | 0.5 | 1-2 | >32 | >32 | >64 | >32 | 16 | 0.5 | 1 |
| DC189 | | | | | | | | | | 8 |

PAR, paromomycin; NEO, neomycin B.

As will be understood by one of ordinary skill in the art, each embodiment disclosed herein can comprise, consist essentially of, or consist of its particular stated element, step, ingredient or component. Thus, the terms "include" or "including" should be interpreted to recite: "comprise, consist of, or consist essentially of." As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically significant reduction in the antibacterial activity of the compounds disclosed herein.

Unless otherwise indicated, all numbers used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; 19% of the stated value; ±18% of the stated value; 17% of the stated value; 16% of the stated value; 15% of the stated value; 14% of the stated value; 13% of the stated value; ±12% of the stated value; 11% of the stated value; ±10% of the stated value; 9% of the stated value; 8% of the stated value; 7% of the stated value; ±6% of the stated value; 5% of the stated value; 4% of the stated value; 3% of the stated value; ±2% of the stated value; or 1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The particulars shown herein are by way of example and for purposes of illustrative discussion of the preferred embodiments of the present invention only and are presented in the cause of providing what is believed to be the most useful and readily understood description of the principles and conceptual aspects of particular embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. A compound characterized by a general formula (100)

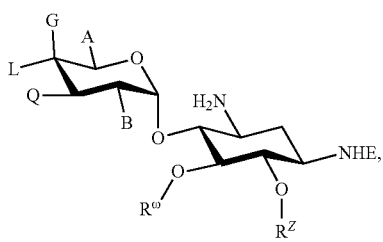
(100)

wherein
i. A is
  CH$_2$OH, wherein
    G is H and L is R$^{A'}$, with R$^{A'}$ being unsubstituted C$_1$ to C$_4$ alkyl, and wherein
a. R$^z$ is H or 2-aminoethyl, and R$^\omega$ is characterized by a general formula (200) or (201)

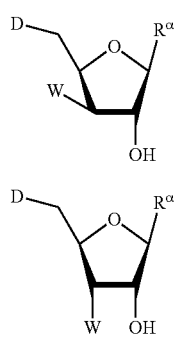

(200)

(201)

wherein R$^\alpha$ designates the bond linking the moiety to moiety (100);

D is selected from NH$_2$, OH, H, and NHR$^4$, wherein R$^4$ is selected from CHO, CONH$_2$, CONHOH, and amino- and/or hydroxy-substituted C$_1$ to C$_6$ alkyl, and W is a moiety characterized by formula (300) or (301)

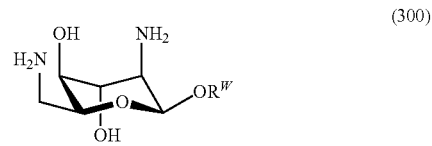
(300)

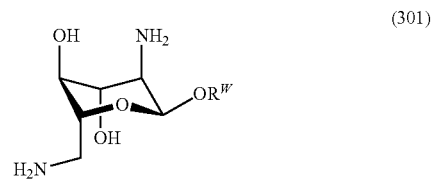
(301)

wherein R$^W$ designates the bond linking the moiety to moiety (200) or (201) with the proviso for, that the molecule is not described by the following combination of parameters:
  A is CH$_2$OH, B is NH$_2$, R$^z$ is H and R$^\omega$ is (201), and D is OH, and wherein
B is NHD$_2$
Q is OH
E is selected from H, CO—R$^3$, CONHR$^3$ and CON(OH)R$^3$, wherein R$^3$ is H or a C$_1$ to C$_6$ substituted or unsubstituted alkyl.

2. The compound according to claim 1, wherein the compound is characterized by the general formula (110)

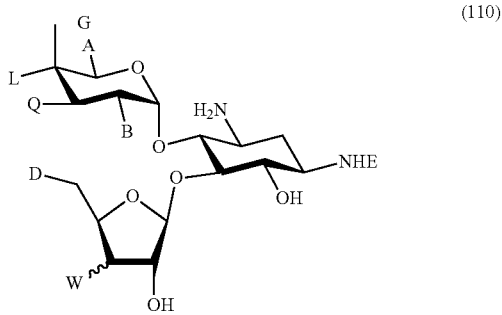
(110)

wherein A, B, D, E, G, L, Q and W have the same meanings as indicated above.

3. The compound according to claim 1, wherein the compound is characterized by the general formula (120),

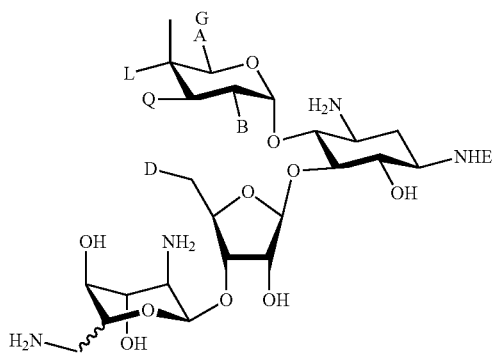

(120)

wherein A, B, D, E, G, L and Q have the same meaning as indicated above.

4. The compound according to claim 1, wherein D is selected from NHCHO (formamide), NHCONH$_2$ (ureide), —NHCONHOH and NHR$^4$, wherein R$^4$ is selected from C$_1$ to C$_4$ unsubstituted alkyl and C$_1$ to C$_4$ aminosubstituted alkyl.

5. The compound according to claim 1, wherein the compound is
   a. 5"-deoxy-5"-formamidoparomomycin (137)
   b. 5"-deoxy-5"-ureidoparomomycin (141), or
   c. 3',5"-dideoxy-5"-formamidoparomomycin (153).

6. The compound according to claim 1, wherein E is H.

7. The compound according to claim 1, wherein D is NHR$^4$ and R$^4$ is selected from CHO, CONH$_2$, CONHOH, COCH$_2$NH$_2$; COCH(NH$_2$)(CH$_2$)$_4$NH$_2$, or COCH(NH$_2$)(CH$_2$)$_3$NHC(NH)NH$_2$, and amino-substituted or hydroxy-substituted methyl, ethyl, n- or iso-propyl.

8. The compound according to claim 1, wherein D is NHCHO or NHCONH$_2$.

9. The compound according to claim 1, wherein E is selected from (S)-4-amino-2-hydroxybutyryl, (S)-3-amino-2-hydroxypropionyl, —CON(OH)(CH$_2$)$_2$NH$_2$, (2R,4S)-2-hydroxy-4,5-diamino-pentanoyl, and (2S,4R)-2,5-dihydroxy-4-aminopentanoyl.

10. The compound according to claim 1, wherein the compound is characterized by the general formula (111)

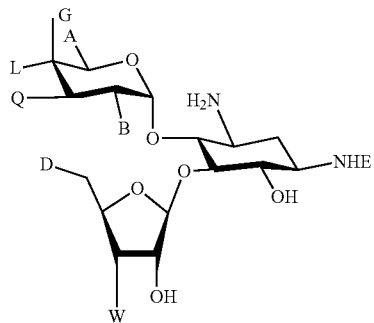

(111)

wherein A, B, D, E, G, L, Q and W have the same meanings as indicated above.

11. The compound according to claim 1, wherein the compound is characterized by the general formula (121

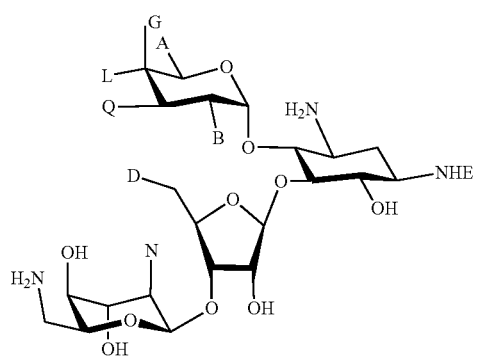

(121)

wherein A, B, D, E, G, L and Q have the same meanings as indicated above.

12. A method for treatment of a bacterial infection, comprising administering to a patient in need thereof, by systemic administration, a compound according to claim 1.

13. The method of claim 12, wherein the infection is caused by a pathogen selected from the genera *klebsellia, Escherichia, Mycobacterium, Pseudomonas, Acinetobacter, Enterobacter,* and *Neisseria*.

14. The method of claim 12, wherein the infection is caused by a pathogen comprising a resistance determinant selected from AAC(6') aminoglycoside N-acetyltransferase, AAC(2') aminoglycoside N-acetyltransferase, APH(3') aminoglycoside O-phosphotransferase and ANT(4') aminoglycoside O-nucleotidyltransferase.

15. The method of claim 12, wherein the infection is caused by a pathogen selected from the genus *Mycobacterium*.

16. The method of claim 12, wherein the infection is caused by a pathogen comprising an AAC(2') aminoglycoside N-acetyltransferase resistance determinant.

17. The method of claim 12, wherein the infection is caused by a pathogen selected from *K. pneumoniae, E. coli, P. aeroginosa, A. baumannii, E. cloacae,* and *N. gonorrhoeae*.

18. A method for treatment of a bacterial infection, comprising administering to a patient in need thereof, by systemic administration, a compound according to claim 1, wherein the patient carries a mutation in the A-site of the mitochondrial ribosomal RNA selected from A1555G and C1494U.

\* \* \* \* \*